(12) United States Patent
Burgess et al.

(10) Patent No.: US 10,688,272 B2
(45) Date of Patent: Jun. 23, 2020

(54) DETERMINISTICALLY CONTROLLED HUMIDIFICATION SYSTEM

(71) Applicant: Fisher & Paykel Healthcare Limited, Auckland (NZ)

(72) Inventors: Russel William Burgess, Auckland (NZ); Dean Antony Barker, Auckland (NZ); Laith Adeeb Hermez, Auckland (NZ); Joel Michael Lawson, Pasadena, CA (US); Robert Stuart Kirton, Auckland (NZ); Kevin Peter O'Donnell, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 413 days.

(21) Appl. No.: 15/507,692

(22) PCT Filed: Sep. 3, 2015

(86) PCT No.: PCT/NZ2015/050128
§ 371 (c)(1),
(2) Date: Feb. 28, 2017

(87) PCT Pub. No.: WO2016/036260
PCT Pub. Date: Mar. 10, 2016

(65) Prior Publication Data
US 2018/0250490 A1    Sep. 6, 2018

Related U.S. Application Data

(60) Provisional application No. 62/045,358, filed on Sep. 3, 2014, provisional application No. 62/213,534, filed on Sep. 2, 2015.

(51) Int. Cl.
*A61M 16/16* (2006.01)
*A61M 16/14* (2006.01)
(Continued)

(52) U.S. Cl.
CPC ........ *A61M 16/161* (2014.02); *A61M 16/024* (2017.08); *A61M 16/109* (2014.02);
(Continued)

(58) Field of Classification Search
CPC .. A61M 16/16; A61M 16/161; A61M 16/109; A61M 2205/33
See application file for complete search history.

(56) References Cited

U.S. PATENT DOCUMENTS 4,430,994 A    2/1984 Clawson et al.
5,031,612 A *  7/1991 Clementi ........... A61M 16/1075
                                                128/204.14
(Continued)

FOREIGN PATENT DOCUMENTS

AU    2008 202 098 A1    2/2009
AU    2008202098         2/2009
(Continued)

OTHER PUBLICATIONS

MR850 Respiratory Humidifier. Technical Manual Revision J [online]. Fisher & Paykel Healthcare, 2005 [retrieved on Apr. 16, 2019]. Retrieved from Internet: <http://www.nbngroup.com/manuals/machine/V-MR850TechManual.pdf> (Year: 2005).*
(Continued)

*Primary Examiner* — Bradley H Philips
*Assistant Examiner* — Savannah L Gabriel
(74) *Attorney, Agent, or Firm* — Knobbe Martens Olson & Bear LLP

(57) ABSTRACT

A respiratory humidification system for providing humidification to gases that pass through a gas passage way before being provided to an airway of a patient is disclosed. The respiratory humidification system may include a liquid flow controller providing a controlled flow of liquid, a heating system including a heating surface configured to be located
(Continued)

US 10,688,272 B2
Page 2 in a gases passage way and provide humidification to gases passing through the passage way, wherein the heating system receives the controlled flow of liquid, and one or more hardware processors providing deterministic control of a humidity level of gases passing through the gas passage way by instructing the liquid flow controller to adjust the controlled flow of liquid received at the heating system.

20 Claims, 23 Drawing Sheets

(51) Int. Cl.
*A61M 16/10* (2006.01)
*A61M 16/00* (2006.01)
*A61M 39/24* (2006.01)
*A61M 16/20* (2006.01)

(52) U.S. Cl.
CPC .......... *A61M 16/147* (2014.02); *A61M 16/16* (2013.01); *A61M 39/24* (2013.01); *A61M 16/106* (2014.02); *A61M 16/208* (2013.01); *A61M 2016/0033* (2013.01); *A61M 2205/3331* (2013.01); *A61M 2205/3334* (2013.01); *A61M 2205/3368* (2013.01); *A61M 2205/3653* (2013.01); *A61M 2205/7518* (2013.01)

(56) References Cited

U.S. PATENT DOCUMENTS

| | | | |
|---|---|---|---|
| 6,095,505 A | 8/2000 | Miller | |
| 6,102,037 A * | 8/2000 | Koch | A61M 16/16 128/201.13 |
| 8,206,337 B2 * | 6/2012 | Blackhurst | A61B 1/00154 604/26 |
| 8,640,696 B2 * | 2/2014 | Pujol | A61M 16/202 128/203.14 |
| 2001/0050080 A1 * | 12/2001 | Seakins | A61M 16/08 128/203.16 |
| 2002/0039487 A1 * | 4/2002 | Wang | F24F 6/10 392/395 |
| 2004/0254524 A1 | 12/2004 | Spearman et al. | |
| 2007/0137646 A1 | 6/2007 | Weinstein et al. | |
| 2009/0223514 A1 | 9/2009 | Smith et al. | |
| 2011/0023874 A1 | 2/2011 | Bath et al. | |
| 2012/0125334 A1 | 5/2012 | Korneff et al. | |
| 2013/0081625 A1 | 4/2013 | Rustad et al. | |
| 2013/0263851 A1 * | 10/2013 | Arcilla | A61M 16/1075 128/203.14 |
| 2015/0125334 A1 | 5/2015 | Uetani et al. | |

FOREIGN PATENT DOCUMENTS

| | | |
|---|---|---|
| CN | 103328031 A | 9/2013 |
| DE | 10 2009 014746 A1 | 10/2010 |
| DE | 102012223445 | 6/2014 |
| EP | 1514570 A2 | 3/2005 |
| GB | 1520836 | 8/1978 |
| WO | WO 1998/002199 | 1/1998 |
| WO | WO 1998/026826 | 6/1998 |
| WO | WO 2008/095245 | 8/2008 |
| WO | WO 2009/049909 A2 | 4/2009 |
| WO | WO 2012/077052 A1 | 6/2012 |
| WO | WO 2012/080923 | 6/2012 |
| WO | WO 2012/080941 | 6/2012 |
| WO | WO 2012/080941 A1 | 6/2012 |
| WO | WO 2012/100291 | 8/2012 |
| WO | WO 2012/100291 A1 | 8/2012 |
| WO | WO 2012/171072 | 12/2012 |
| WO | WO 2014/006574 | 1/2014 |

OTHER PUBLICATIONS

International Search Report and Written Opinion for PCT/NZ2015/050128 dated Dec. 24, 2015, in 23 pages.
Extended European Search Report for Application No. EP 15 83 8898 dated Mar. 21, 2018.
Taiwanese Office Action/Examination Notification for Taiwan Patent Application No. 104129233. Search completed on Jan. 10, 2019.

\* cited by examiner

DETERMINISTICALLY CONTROLLED HUMIDIFICATION SYSTEM

INCORPORATION BY REFERENCE TO ANY PRIORITY APPLICATIONS

The present application is a national phase of PCT Application No. PCT/NZ2015/050128, filed Sep. 3, 2015, which claims priority from U.S. Provisional Application No. 62/045,358, filed Sep. 3, 2014, and U.S. Provisional Application No. 62/213,534, filed Sep. 2, 2015, the contents of each of which are incorporated by reference in its entirety. Any and all applications for which a foreign or domestic priority claim are identified in the Application Data Sheet filed with the present application are hereby incorporated by reference under 37 CFR 1.57.

BACKGROUND

The present disclosure generally relates to humidified gases therapy. More particularly, the present disclosure relates to humidification systems for use in humidified gases therapy.

A patient dealing with respiratory illness, for example chronic obstructive pulmonary disease (COPD), can have difficulty engaging in effective respiration. This difficulty may be the result of a variety of causes, including a breakdown of lung tissue, dysfunctions of the small airways, excessive accumulation of sputum, infection, genetic disorders, or cardiac insufficiency. With some respiratory illnesses, it is useful to provide a therapy that can improve the ventilation of the patient. In some situations, the patient can be provided with a respiratory therapy system that includes a gases source, an interface that may be used to transmit gases to an airway of a patient, and a conduit extending between the gases source and the interface. Gases delivered to the airway of the patient from the gases source can help to promote adequate ventilation. The gases source may include, for example, a container of air and/or another gas suitable for inspiration, e.g., oxygen or nitric oxide, a mechanical blower capable of propelling gases through the conduit to the interface, or some combination of both. The respiratory therapy system can include a gases humidifier that can humidify and heat gases passing through the respiratory therapy system to improve patient comfort and/or improve the prognosis of the patient's respiratory illness. The gases humidifier can include a water reservoir and a heating element for heating the water in the reservoir. As the water heats up, water vapor is formed that can join the stream of gases passing through the gases humidifier.

Conventional gases humidifiers are useful in ameliorating the discomfort of cold and dry gases therapies, but are typically configured in such a way that all of the water in the reservoir, or an excess of water, must be heated before the generation of vapor rises to an acceptable level for providing adequately humidified gases. In some cases it can take up to half an hour from turning the humidifier on to begin generating sufficient water vapor. Additionally, conventional gases humidifiers may not be able to respond appropriately to changing input conditions, or may have an impaired response in part due to the high thermal inertia of the water in the reservoir.

SUMMARY

The present disclosure provides a water vaporization system that does not require a reservoir of water, or an excess of water, to be heated. Disclosed are embodiments which allow a desired amount of water to be quickly vaporized, thus improving response time to system or environmental changes and greatly reducing warm-up periods.

According to a first aspect of the present disclosure, a respiratory humidification system for providing humidification to gases that pass through a gas passage way before being provided to an airway of a patient, can include a liquid flow controller for providing a controlled flow of liquid; a heating system including a heating surface configured to be located in a gases passage way and provide humidification to gases passing through the passage way, wherein the heating system receives the controlled flow of liquid, the heating system configured to maintain the heating surface at a predetermined temperature of between approximately 30 degrees Celsius (° C.) and approximately 99.9° C.; and one or more hardware processors providing deterministic control of a humidity level of gases passing through the gas passage way by instructing the liquid flow controller to adjust the controlled flow of liquid received at the heating system.

The heating system may be configured to maintain the heating surface at a predetermined temperature of between approximately 35° C. and approximately 90° C., between approximately 40° C. and approximately 80° C., between approximately 45° C. and approximately 70° C., between approximately 45° C. and approximately 60° C., between approximately 50° C. and approximately 60° C., or at a predetermined temperature at approximately 50° C.

The liquid may be water. The liquid flow controller may include a metering system. The liquid flow controller may be a pump. The pump may be a positive displacement pump. The positive displacement pump may be a piezoelectric, diaphragm pump, or peristaltic pump. The liquid flow controller may be a pressure feed, such as a gravity feed, and a control valve. The liquid flow controller may include a non-return valve configured to keep the liquid flow controller primed and/or protect the system from contamination. The liquid flow controller may be configured to use a wicking or capillary action. The respiratory humidification system may include a safety valve to prevent flow of liquids if the liquid controller fails. The respiratory humidification system may include a liquid reservoir. The respiratory humidification system may include a flow restriction device positioned between the liquid reservoir and the liquid flow controller and configured to prevent gravity driven flow from influencing a delivered flow of liquid. The flow restriction device may be an elastic protrusion that restricts the flow path. The liquid flow controller may be a pump in an open loop configuration. The liquid flow controller may be a pump or flow actuator in series with a flow sensor in a closed loop configuration. The liquid flow controller may provide a continuous flow of water in the range of 0 mL/min to approximately 10 mL/min. The liquid flow controller may provide a continuous flow of liquid in the range of 0 mL/min to approximately 7 mL/min. The liquid flow controller may provide a continuous flow of liquid in the range of 0 mL/min to approximately 5 mL/min. The liquid flow controller may provide a continuous flow of liquid in the range of approximately 40 µL/min to approximately 4 mL/min, or the range of approximately 70 µL/min to approximately 2.5 mL/min. The liquid flow controller may provide a controlled flow of liquid with an accuracy of approximately ±15% of a desired liquid flow rate, an accuracy of approximately ±10% of a desired liquid flow rate, an accuracy of approximately ±6.5% of a desired liquid flow rate, or an accuracy of approximately ±5% of a desired liquid flow rate.

The respiratory humidification system may include a flow sensor. The flow sensor may be a thermal mass meter. The flow sensor may be drip feed counter. The flow sensor may be a differential pressure flow sensor.

The one or more hardware processors may provide deterministic control of the humidity level based on a flow rate of the gases. The one or more hardware processors may provide deterministic control of the humidity level based on the evaporation rate of water from the heating surface. The one or more hardware processors may provide deterministic control of the humidity level based on the temperature of the heating surface wherein the temperature of the heating surface is maintained at a constant temperature. The one or more hardware processors may provide deterministic control of the humidity level based on the temperature of the heating surface wherein the temperature of the heater surface is controlled. The one or more hardware processors may provide deterministic control of the humidity level based on the absolute or barometric pressure of gases at the inlet. The one or more hardware processors may provide deterministic control of the humidity level based on the dew point temperature of the gases at the inlet. The one or more hardware processors may provide deterministic control of the humidity level based on enthalpy provided by the heating surface. The one or more hardware processors may provide deterministic control of the humidity level based on the temperature of the gases prior to interaction with the heating system. The one or more hardware processors may provide deterministic control of the humidity level based on the relative humidity of the gases prior to interaction with the heating system. The one or more hardware processors may provide deterministic control of the humidity level based on the effective heating area of the heating surface. The one or more hardware processors may provide deterministic control of the humidity level based on the pressure of the gases. The one or more hardware processors may provide deterministic control of the humidity level based on a function of gas velocity. The one or more hardware processors may provide deterministic control of the humidity level based on temperature of the liquid in the controlled flow of liquid. The respiratory humidification system may include a water temperature sensor. The respiratory humidification system may include a gas flow rate sensor. The respiratory humidification system may include a gas flow rate sensor at an inlet of the gases passage way. The respiratory humidification system may include a liquid flow rate determined by a model. The respiratory humidification system may include a gases flow rate determined by a model. The respiratory humidification system may include an ambient pressure sensor. The respiratory humidification system may include a pressure sensor positioned at or near the heater surface. The respiratory humidification system may include a heating surface temperature sensor. The respiratory humidification system may include an ambient dew point temperature sensor or ambient humidity sensor positioned upstream of a humidification region. The respiratory humidification system may include an ambient dew point temperature sensor positioned upstream from a gases pre-heater. The respiratory humidification system may include an ambient dew point temperature sensor positioned downstream from a gases pre-heater. The respiratory humidification system may include an ambient dew point temperature sensor positioned downstream from a gases pre-heater and a temperature sensor at a gases passage way inlet. The respiratory humidification system may include at least one temperature sensor forming part of the heating system. The at least one temperature sensor may be utilized to determine a proportion of the heater that is saturated with a liquid. The respiratory humidification system may include a gases pre-heater. A temperature of the gases at a gases passage way inlet may be controlled in an open loop fashion via control of a power to the pre-heater. The respiratory humidification system may include a liquid pre-heater. The heating surface may include a wicking surface. Heat may be supplied to the heating surface by a PCB with resistive traces or tracking. Heat may be supplied to the heating surface by etched foil or one or more flexible PCBs. Heat may be supplied by a heating wire. Heat may be supplied by a PTC ceramic. Heat may be supplied by a Peltier or thermoelectric device. The heating surface may be over-molded and micro-channels may be included in the over-mold configured to wick water onto the heater. A surface temperature of the heating surface may be at least partially determined by using a resistance or other characterization of the heating system. The resistance may indicate an average heater system temperature. In some configurations, the heating system is arranged such that a higher density of heat is provided in a specified region of the heater such that those regions have a higher power density. The higher density of heat may be near an outlet of a water supply. The higher density of heat may be provided in a water pre-heating area. The respiratory humidification system may include a temperature sensor at an outlet of the gases passage way.

According to another aspect of the present disclosure, a high efficiency respiratory humidification system for providing heated and humidified respiratory gases to a patient is described. The respiratory humidification system may include a respiratory gas passage way having an inlet and an outlet, where gases flow from the inlet to the outlet during operation; a pre-heater configured to heat a gas flow; and a heating surface separate from the pre-heater and located downstream from the pre-heater, the heating surface including wicking features configured to wick a liquid across a face of the heating surface, the heating surface further configured to heat the liquid during and/or after wicking. The respiratory humidification system may include a gas flow generator. The pre-heater may be a gas heating element. The gas heating element may be one of a PCB including resistive elements (e.g., traces or tracking), an etched foil film, a heating coil, or a PTC element, among others. The respiratory humidification system may include a temperature sensor positioned downstream from the pre-heater. Power provided to the gas heating element may be controlled according to a measurement obtained from the downstream temperature sensor. The respiratory humidification system may include a temperature sensor positioned upstream from the pre-heater. Power provided to the gas heating element may be controlled according to a gas flow rate and a measurement obtained from the upstream temperature sensor. A characterization of the gas heating element may be used as a temperature sensor. A desired downstream temperature may be set according to an evaporation rate of liquid from the heating surface. The desired downstream temperature may be set in order to ensure substantially all sensible heat is supplied to the gas flow by the pre-heater. The desired downstream temperature may be set between 0° C. and approximately 5° C. above an output dew point temperature. The desired downstream temperature may be set to obtain a predetermined output absolute humidity. The desired downstream temperature may be set to obtain a given output absolute humidity. The desired downstream temperature may be set to approximately 25° C. to approximately 43° C., or approximately 31° C. to approximately 43° C., or approximately 31° C. to approximately 41° C., or approximately 31° C. to approximately 37° C., or approximately 37° C. The respiratory humidification system may include a liquid flow generator. The respiratory humidification system may include an apparatus for pre-heating the liquid flow. The apparatus for pre-heating the liquid flow may be incorporated into the heater-surface structure by increasing a number of resistive tracks where the water is introduced. The apparatus for pre-heating the liquid flow may be in a water supply line. The wicking features may be one or more of an absorptive fabric or paper, micro-channels, hydrophilic coated surface, capillary or contact wicks, or thin porous media, among others. The wicking features may include a coupling configured to distribute the liquid onto the heating surface. The coupling may be a length of wicking media bonded or brought into contact with the heating surface or wicking features. The coupling may be a second surface forming an acute angle with the wicking features. The coupling may be a cavity in contact with the heating surface or wicking features. The coupling may be one or more of a line source, a point source, a radial source, or multiple line, point and radial sources, or any combination thereof. The heating surface may be maintained at a temperature of between approximately 30° C. and approximately 99.9° C., between approximately 35° C. and approximately 90° C., between approximately 40° C. and approximately 80° C., between approximately 45° C. and approximately 70° C., between approximately 45° C. and approximately 60° C., between approximately 50° C. and approximately 60° C., or at approximately 50° C. The wicking features may be mechanically configured to be positioned within a liquid delivery tube. The respiratory humidification system may be configured to be within, or as part of, an inspiratory tube for delivering gas to a patient. The respiratory humidification system may include a filter. The filter may be in a liquid delivery line. The filter may be positioned downstream from a pump. The filter may be positioned at an inlet to the heating surface. The filter may be a biologic filter. The respiratory humidification system may include a UV source for sterility.

According to another aspect of the present disclosure, a respiratory humidification system for providing heated and humidified respiratory gases to a patient may include a liquid flow controller providing a controlled flow of liquid; a heating system including a heating surface configured to receive the controlled flow of liquid and provide humidification to gases passing through the humidification system; one or more temperature sensors measuring a surface temperature of the heating surface; one or more hardware processors providing deterministic control of a humidity level of gases passing through the respiratory system by instructing the liquid flow controller to adjust the controlled flow of liquid received at the heating system and instructing the heating system to adjust the surface temperature of the heating surface, wherein adjusting the surface temperature of the heating surface provides control to produce a known evaporative area; and one or more liquid sensors configured to detect whether the heating surface is wetted in at least one region. The one or more liquid sensors may be at least two liquid sensors configured to detect whether the heating surface is wetted at two or more regions of the heating surface. The at least two liquid sensors may be two temperature sensors. The one or more liquid sensors may be located at, on, adjacent, or proximal the heating surface. The liquid may be water.

The liquid flow controller may be a metering system. The liquid flow controller may include a pump. The pump may be a positive displacement pump. The positive displacement pump may be a piezoelectric diaphragm pump or peristaltic pump. The liquid flow controller may be a pressure feed, such as gravity feed, and a control valve. The liquid flow controller may include a non-return valve configured to keep the liquid flow controller primed and/or reduce the opportunity for flow reversal. The liquid flow controller may be configured to use a wicking or capillary action. The respiratory humidification system may include a safety valve to prevent flow of liquids if the liquid controller fails. The respiratory humidification system may include a liquid reservoir. The respiratory humidification system may include a flow restriction device positioned between the liquid reservoir and the liquid flow controller and configured to prevent gravity driven flow from influencing a delivered flow of liquid. The flow restriction device may be an elastic protrusion that restricts the flow path. The liquid flow controller may be a pump in an open loop configuration. The liquid flow controller may be a pump or flow actuator in series with a flow sensor in a closed loop configuration. The pump may be piezoelectric pump. The flow sensor may be a thermal mass meter. The liquid flow controller may provide a continuous flow of water in the range of 0 mL/min to 10 mL/min. The liquid flow controller may provide a continuous flow of water in the range of 0 mL/min to 7 mL/min. The liquid flow controller may provide a continuous flow of water in the range of 0 mL/min to 5 mL/min. The liquid flow controller may provide a continuous flow of water in the range of 40 µL/min to 4 mL/min, or the range of 70 µL/min to 2.5 mL/min. The flow controller may provide a controlled flow of liquid with an accuracy of approximately ±15% of a desired liquid flow rate, an accuracy of approximately ±10% of a desired liquid flow rate, an accuracy of approximately ±6.5% of a desired liquid flow rate, or an accuracy of approximately ±5% of a desired liquid flow rate.

The one or more hardware processors may provide deterministic control of the humidity level based on a flow rate of the gases. The one or more hardware processors may provide deterministic control of the humidity level based on evaporation rate of liquid from the heating surface. The one or more hardware processors may provide deterministic control of the humidity level based on the temperature of the heating surface wherein the temperature of the heater surface is maintained at a constant temperature. The one or more hardware processors may provide deterministic control of the humidity level based on the temperature of the heating surface wherein the temperature of the heater surface is controlled. The one or more hardware processors may provide deterministic control of the humidity level based on the absolute or barometric pressure of gases at the inlet. The one or more hardware processors may provide deterministic control of the humidity level based on the dew point temperature of the gases at an inlet. The one or more hardware processors may provide deterministic control of the humidity level based on enthalpy provided by the heating surface. The one or more hardware processors may provide deterministic control of the humidity level based on the temperature of the gases prior to interaction with the heating system. The one or more hardware processors may provide deterministic control of the humidity level based on the relative humidity of the gases prior to interaction with the heating system. The one or more hardware processors may provide deterministic control of the humidity level based on the effective heating area of the heating surface. The one or more hardware processors may provide deterministic control of the humidity level based on the pressure of the gases. The one or more hardware processors may provide deterministic control of the humidity level based on a function of gas velocity. The one or more hardware processors may provide deterministic control of the humidity level based on a temperature of the liquid in the controlled flow of liquid. The respiratory humidification system may include a water temperature sensor. The respiratory humidification system may include a gas flow rate sensor. The respiratory humidification system may include a gas flow rate sensor at an inlet of the gases passage way. The respiratory humidification system may include a liquid flow rate determined by a model. The respiratory humidification system may include a gases flow rate determined by a model. The respiratory humidification system may include an ambient pressure sensor. The respiratory humidification system may include an ambient dew point temperature sensor or ambient humidity sensor positioned upstream of a humidification region. The respiratory humidification system may include an ambient dew point temperature sensor positioned upstream from a gases pre-heater. The respiratory humidification system may include an ambient dew point temperature sensor positioned downstream from a gases pre-heater. The respiratory humidification system may include an ambient dew point temperature sensor positioned downstream from a gases pre-heater and a temperature sensor at a gases passage way inlet. The respiratory humidification system may include at least one temperature sensor forming part of the heating system. The at least one temperature sensor may be utilized to determine a proportion of the heater that is saturated with a liquid. The respiratory humidification system may include a gases pre-heater. A temperature of the gases at a gases passage way inlet may be controlled in an open loop fashion via control of a power to the pre-heater. The respiratory humidification system may include a liquid pre-heater. The one or more liquid sensors may be used to prevent overflow of liquid onto the heating surface. The one or more liquid sensors may be used by the one or more hardware processors to adjust the deterministic control of the humidity level of gases passing through the respiratory system. The one or more liquid sensors may be used by the one or more hardware processors to adjust the evaporative area of the heating surface. The one or more liquid sensors may be temperature sensors. The one or more liquid sensors may be resistive or capacitive sensors.

According to another aspect of the present disclosure, a heater plate for a respiratory humidification system includes a printed circuit board (PCB) or etched foil over-molded with a surface comprising micro-channels. The surface may have micro-channels that extend in only a single direction. The micro-channels may include a first set of distribution channels connected to a second set of main channels. The number of distribution channels may be less than the number of main channels. The micro-channels may be distributed radially from a single point. The heating system may be used with any of the respiratory humidification systems described herein.

According to another aspect of the present disclosure, a respiratory humidification system for providing humidification to gases that pass through a gas passage way before being provided to an airway of a patient, the respiratory humidification system includes a liquid flow controller providing a controlled flow of liquid; a heating system including a heating surface configured to receive the controlled flow of liquid and provide humidification to gases passing through the humidification system, wherein the heating surface is configured to wick liquid across the surface thereof; and a gas pre-heater arranged in the gas passage way upstream of the heating system. The respiratory humidification system may include a coupling configured to receive the controlled flow of liquid from the liquid control and distribute the liquid onto the heating surface. The respiratory humidification system may be configured to be in-line with an inspiratory tube for delivering gases to a patient. The respiratory humidification system may be configured to be within an inspiratory tube for delivering gases to a patient. The liquid may be water. The respiratory humidification system may include a filter. The filter may be in a liquid delivery line. The filter may be positioned downstream from a pump. The filter may be positioned at an inlet to the heating surface. The filter may be a biologic filter. The respiratory humidification system may include a UV source for sterility.

The liquid flow controller may include a metering system. The liquid flow controller may be a pump. The pump may be a positive displacement pump. The positive displacement pump may be a piezoelectric, diaphragm pump, or peristaltic pump. The liquid flow controller may comprise a pressure feed, such as a gravity feed, and a control valve. The liquid flow controller may include a non-return valve configured to keep the liquid flow controller primed. The liquid flow controller may be configured to use a wicking or capillary action. The respiratory humidification system may further include a safety valve to prevent flow of liquids if the liquid controller fails. The respiratory humidification system may further include a liquid reservoir. The respiratory humidification system may further include a flow restriction device positioned between the liquid reservoir and the liquid flow controller and configured to prevent gravity driven flow from influencing a delivered flow of liquid. The flow restriction device may be an elastic protrusion that restricts the flow path. The liquid flow controller may be a pump in an open loop configuration. The liquid flow controller may be a pump or flow actuator in series with a flow sensor in a closed loop configuration. The liquid flow controller may provide a continuous flow of liquid in the range of 0 mL/min to approximately 10 mL/min. The liquid flow controller may provide a continuous flow of liquid in the range of 0 mL/min to approximately 7 mL/min. The liquid flow controller may provide a continuous flow of liquid in the range of 0 mL/min to approximately 5 mL/min. The liquid flow controller may provide a continuous flow of liquid in the range of 40 µL/min to approximately 4 mL/min, or in the range of approximately 70 µL/min to approximately 2.5 mL/min. The liquid flow controller may provide a controlled flow of liquid with an accuracy of approximately ±15% of a desired liquid flow rate, an accuracy of approximately ±10% of a desired liquid flow rate, an accuracy of approximately ±6.5% of a desired liquid flow rate, or an accuracy of approximately ±5% of a desired liquid flow rate.

The heating system may include a heater plate comprising a printed circuit board (PCB) or etched foil over-molded with a surface comprising micro-channels. The surface may have micro-channels that extend in only a single direction. The micro-channels may include a first set of distribution channels connected to a second set of main channels. The number of distribution channels may be less than the number of main channels. The micro-channels may be distributed radially from a single point. The coupling may be a fibrous, porous or sintered polymer. The heating surface may be immersed in the gas flow. The heating surface may include modular zones.

According to another aspect of the present disclosure, a respiratory humidification system includes a liquid flow controller providing a controlled flow of liquid; a heating system including a heating surface configured to be located in a gases passage way and provide humidification to gases passing through the passage way, wherein the heating system receives the controlled flow of liquid, the heating system configured to maintain the heating surface at a predetermined temperature of between approximately 30° C. and approximately 99.9° C.; and heating surface may be configured to be maintained at a temperature of between approximately 30° C. and approximately 99.9° C., and wherein approximately 80%-99.9% of the power output of the system is transferred into heat in the liquid. The heating surface maybe configured to be maintained at a temperature of between approximately 35° C. and approximately 90° C., between approximately 45° C. and approximately 70° C., between approximately 45° C. and approximately 60° C., between approximately 50° C. and approximately 60° C., or at a temperature of approximately 50° C. In some configurations, approximately 85%-99.99% of the power output of the system is transferred into heat in the liquid, approximately 90%-99.99% of the power output of the system is transferred into heat in the liquid, approximately 95%-99.99% of the power output of the system is transferred into heat in the liquid, or approximately 98% of the power output of the system is transferred into heat in the liquid. The liquid may be water. The respiratory humidification system may be configured as any of the respiratory humidification systems described herein.

According to another aspect of the present disclosure, a respiratory humidification system for providing humidification to gases that pass through a gas passage way before being provided to an airway of a patient includes an apparatus for heating a gas flow and positioned upstream of a humidification region; a liquid flow generator; and a heating system including a heating surface configured to be located in a gases passage way and provide humidification to gases passing through the passage way, wherein the heating system is configured to maintain a heating surface at a predetermined temperature of between approximately 30° C. and approximately 99.9° C. The heating system may be configured to maintain the heating surface at a predetermined temperature of between approximately 35° C. and approximately 90° C. The heating system may be configured to maintain the heating surface at a predetermined temperature of between approximately 40° C. and approximately 80° C. The heating system may be configured to maintain the heating surface at a predetermined temperature of between approximately 45° C. and approximately 70° C. The heating system may be configured to maintain the heating surface at a predetermined temperature of between approximately 45° C. and approximately 60° C. The heating system may be configured to maintain the heating surface at a predetermined temperature of between approximately 50° C. and approximately 60° C. The heating system may be configured to maintain the heating surface at a predetermined temperature at approximately 50° C. The apparatus may be a pre-heater. The pre-heater may include a gas heating element. The gas heating element may be one of a PCB including resistive elements, an etched foil film, a heating coil, or a PTC element, among others. The respiratory humidification system may include a temperature sensor positioned downstream from the pre-heater. Power provided to the gas heating element may be controlled according to a measurement obtained from the downstream temperature sensor. The respiratory humidification system may include a temperature sensor positioned upstream from the pre-heater. Power provided to the gas heating element may be controlled according to an airflow rate and a measurement obtained from the upstream temperature sensor. A characterization of the gas heating element may be used as a temperature sensor. A desired downstream temperature after the pre-heater may be set according to an evaporation rate of the heating surface. The desired downstream temperature may be set in order to ensure substantially all sensible heat is supplied by the pre-heater. The desired downstream temperature may be set between 0° C. and approximately 5° C. above an output temperature. The desired downstream temperature may be set to obtain a given output relative humidity. The desired downstream temperature may be set to obtain a given output absolute humidity. The desired downstream temperature may be set to approximately 25° C. to approximately 43° C., or approximately 31° C. to approximately 43° C., or approximately 31° C. to approximately 41° C., or approximately 31° C. to approximately 37° C., or approximately 37° C. The respiratory humidification system may include an apparatus for pre-heating the liquid flow. The apparatus for pre-heating the liquid flow may be incorporated into the heating structure by increasing a number of resistive heating tracks where the liquid is introduced. The apparatus for pre-heating the liquid flow may be in a liquid supply line.

According to another aspect of the present disclosure, deterministic control, in a respiratory humidification system, of humidity by control of water flow to a heating source is described. Deterministic control of the humidity level may be based on a flow rate of the gases. Deterministic control of the humidity level may be based on evaporation rate of water from the heating surface. Deterministic control of the humidity level may be based on the temperature of the heating surface wherein the temperature of the heater surface is maintained at a constant temperature. Deterministic control of the humidity level may be based on the temperature of the heating surface wherein the temperature of the heater surface is controlled. Deterministic control of the humidity level may be based on the absolute or barometric pressure of gases at the inlet. Deterministic control of the humidity level may be based on the dew point temperature of the gases at the inlet. Deterministic control of the humidity level may be based on enthalpy provided by the heating surface. Deterministic control of the humidity level may be based on the temperature of the gases prior to interaction with the heating system. Deterministic control of the humidity level may be based on the relative humidity of the gases prior to interaction with the heating system. Deterministic control of the humidity level may be based on the effective heating area of the heating surface. Deterministic control of the humidity level may be based on the pressure of the gases. Deterministic control of the humidity level may be based on a function of gas velocity. Deterministic control of the humidity level may be based on a temperature of the liquid in the controlled flow of liquid. Deterministic control may be based on a combination of two or more of the aforementioned inputs, and all combinations of the above inputs are within the scope of this disclosure. Deterministic control may be based on a combination of control of water flow to a heating source and a flow rate of the gases. Deterministic control may be based on a combination of control of water flow to a heating source, a flow rate of the gases, and the dew point temperature of the gases at the inlet. Deterministic control may be based on a combination of control of water flow to a heating source, a flow rate of the gases, and the absolute or barometric pressure of the gases at the inlet. Deterministic control may be based on a combination of control of water flow to a heating source, a flow rate of the gases, the absolute or barometric pressure of the gases at the inlet, and the dew point temperature of the gases at the inlet. The respiratory humidification system may include a water temperature sensor. The respiratory humidification system may include a gas flow rate sensor. The respiratory humidification system may include a gas flow rate sensor at an inlet of the gases passage way. The respiratory humidification system may include a liquid flow rate determined by a model. The respiratory humidification system may include a gases flow rate determined by model. The respiratory humidification system may include an ambient pressure sensor. The respiratory humidification system may include a pressure sensor positioned at or near the heater surface. The respiratory humidification system may include a heating surface temperature sensor. The respiratory humidification system may include an ambient dew point temperature sensor or ambient humidity sensor positioned upstream of a humidification region. The respiratory humidification system may include an ambient dew point temperature sensor positioned upstream from a gases pre-heater. The respiratory humidification system may include an ambient dew point temperature sensor positioned downstream from a gases pre-heater. The respiratory humidification system may include an ambient dew point temperature sensor positioned downstream from a gases pre-heater and a temperature sensor at a gases passage way inlet. The respiratory humidification system may include at least one temperature sensor forming part of the heating system. The at least one temperature sensor may be utilized to determine a proportion of the heater surface area that is saturated (or covered) with a liquid. The respiratory humidification system may include a gases pre-heater. A temperature of the gases at a gases passage way inlet may be controlled in an open loop fashion via control of a power to the pre-heater. The respiratory humidification system may include a liquid pre-heater. The heating surface may include a wicking surface. Heat may be supplied to the heating surface by a PCB with resistive traces or tracking. Heat may be supplied to the heating surface by etched foil or flexible PCBs. Heat may supplied by a heating wire. Heat may be supplied by a PTC ceramic. Heat may be supplied by a Peltier or thermoelectric device. The heating surface may be an over-mold including micro-channels in the over-mold configured to conduct liquid, such as water. A surface temperature of the heating surface may be at least partially determined by using a resistance or other characterization of the heating system. The resistance may indicate an average heater system temperature. In some configurations, the heating system is arranged such that a higher density of heat is provided in a specified region of the heater such that those regions have a higher power density. The higher density of heat may be near an outlet of a water supply. The higher density of heat may be provided in a water pre-heating area. The respiratory humidification system of may include a temperature sensor at an outlet of the gases passage way.

According to another aspect of the present disclosure, a respiratory humidification system is provided that provides in-line humidification. In-line humidification allows humidification to occur in the gas flow path, such that the humidification system may be positioned within, partially within, or at the end of, an inspiratory tube, for instance.

According to another aspect of the present disclosure, there is provided a respiratory humidification system including a gases channel through which gases may flow, the gases channel extending between an inlet location and an outlet location, the gases channel including a humidification location between the inlet and outlet locations; a heating surface in fluid communication with the gases channel, the heating surface configured to be maintained within a temperature range; and a water flow controller configured to control a flow of water to the heating surface; where in use, a humidity level of the gases at the outlet location is deterministically controlled by control of a water flow rate to the heating surface.

The water flow controller can include a metering arrangement. The metering arrangement can further include a pump. The pump can be a positive displacement pump, such as, for example, a piezoelectric diaphragm pump, a peristaltic pump, a micro-pump, or a progressive cavity pump. The pump can also be a pressure feed in series with a control valve. The pressure source may be gravity. The respiratory humidification system may have a conduit in fluid communication with the metering arrangement, the conduit configured to carry water to the metering arrangement. The conduit can have a non-return valve configured to keep the metering arrangement primed. The conduit can also have a non-return valve configured to keep the pump primed. The metering arrangement can include a wicking structure that employs capillary action to controllably meter the water to the wicking element and/or to the heating surface. The conduit can also have a safety valve, such as a pressure relief valve, in the conduit leading to the metering arrangement. The respiratory humidification system can have a reservoir configured to hold water. The respiratory humidification system can also have a flow restriction device positioned between the reservoir and the metering arrangement to prevent gravity-driven flow from influencing the water flow path. The flow restriction device can be an elastic protrusion that squeezes or otherwise restricts the flow path. The water flow controller may be a pump in an open-loop configuration. The water flow controller may be a pump or a flow actuator in series with a flow sensor in a closed-loop configuration. The water flow controller may provide a continuous flow of water in the range of 0 mL/min to approximately 5 mL/min. The water flow controller may provide a continuous flow of water in the range of 0 mL/min to approximately 7 mL/min. The water flow controller may provide a continuous flow of water in the range of 0 mL/min to approximately 5 mL/min. The water flow controller may provide a continuous flow of water in the range of approximately 40 µL/min to approximately 4 mL/min, or in the range of approximately 70 µL/min to approximately 2.5 mL/min. The water flow controller may provide a continuous flow of water in the range of approximately 40 µL/min to approximately 4 mL/min. The water flow controller may provide a continuous flow of water in the range of approximately 70 µL/min to approximately 2.5 mL/min. The water flow controller may provide a flow rate of water at an accuracy of approximately ±15%. The water flow controller may provide a flow rate of water at an accuracy of approximately ±10%. The water flow controller may provide a flow rate of water at an accuracy of approximately ±6.5%. The water flow controller may provide a flow rate of water at an accuracy of approximately ±5%.

The heating surface may have a flow sensor. The flow sensor may be a thermal mass meter. The flow sensor may be a drip feed counter. The flow sensor may be a differential pressure flow sensor.

Control of the water flow rate to the heating surface may be based on a flow rate of the gases in the gases channel. Control of the water flow rate to the heating surface may be based on an evaporation rate of the water from the heating surface. Control of the water flow rate to the heating surface may be based on a temperature of the heating surface wherein the temperature of the heating surface is maintained at a constant temperature. Control of the water flow rate to the heating surface may be based on a temperature of the heating surface wherein the temperature of the heating surface is controlled. Control of the water flow rate to the heating surface may be based on an absolute or barometric pressure of the gases at or near the inlet location. Control of the water flow rate to the heating surface may be based on a dew point temperature of the gases at the inlet location. Control of the water flow rate to the heating surface may be based on an enthalpy provided by the heating surface. Control of the water flow rate to the heating surface may be based on a power level provided by the heating surface. Control of the water flow rate to the heating surface may be based on a temperature of the gases at the inlet location. The dew point temperature of the gases at the inlet location may be derived by processing information provided by a temperature sensor and a humidity sensor. Control of the water flow rate to the heating surface may be based on the dew point temperature of the gases at the inlet location. Control of the water flow rate to the heating surface may be based on a relative humidity level of the gases at the inlet location. Control of the water flow rate to the heating surface may be based on an effective heating area of the heating surface. Control of the water flow rate to the heating surface may be based on a pressure level of the gases in the gases channel. Control of the water flow rate to the heating surface may be based on a velocity of the gases flowing in the gases channel. Control of the water flow rate to the heating surface may be based on a temperature of the water flow. The respiratory humidification system may include a water temperature sensor. The respiratory humidification system may include a gases flow rate sensor. The respiratory humidification system may determine the water flow rate based on a model. The respiratory humidification system may determine the gases flow rate based on a model. The respiratory humidification system may include an ambient pressure sensor. The pressure sensor may be positioned at or near the heater surface. The respiratory humidification system may include a temperature sensor configured to measure a temperature of the heating surface. The respiratory humidification system may include an ambient dew point temperature sensor positioned within the gases channel upstream of the humidification location. The respiratory humidification system may include an ambient humidity sensor positioned within the gases channel upstream of the humidification location. The respiratory humidification system may include a gases pre-heater. The gases pre-heater may be disposed within the gases channel between the inlet and the humidification locations. The ambient dew point sensor may be positioned within the gases channel upstream of the gases pre-heater. The ambient humidity sensor may be positioned within the gases channel upstream of the gases pre-heater. The ambient dew point temperature sensor may be positioned within the gases channel downstream of the gases pre-heater. The ambient humidity sensor may be positioned within the gases channel downstream of the gases pre-heater. The ambient dew point temperature sensor may be positioned within the gases channel downstream of the gases pre-heater in combination with a temperature sensor positioned at the inlet location of the gases channel. The respiratory humidification system may include at least one temperature sensor configured to measure at least one temperature of the heating surface. The at least one temperature sensor may be configured to determine a proportion of the heating surface that is saturated with water. The respiratory humidification system may control a gases temperature at the inlet location of the gases channel by controlling a power level to the gases pre-heater in an open loop manner. The respiratory humidification system may include a water pre-heater.

The heating surface can be configured to be maintained at a temperature range. The temperature range may be between approximately 30° C. and approximately 99.9° C. The temperature range may be between approximately 35° C. and approximately 90° C. The temperature range may be between approximately 40° C. and approximately 80° C. The temperature range may be between approximately 45° C. and approximately 70° C. The temperature range may be between approximately 45° C. and approximately 60° C. The temperature range may be between approximately 50° C. and approximately 60° C. The heating surface may be configured to maintain a temperature of approximately 50° C. The heating surface may include a wicking surface. The heating surface may include a heating element configured to provide heat to the heating surface. The heating element may be a circuit board. The circuit board may be a printed circuit board. The circuit board may be a flexible circuit board. The flexible circuit board may be made of polymer, the polymer may be silicone, polyester, or polyimide. The circuit board may have a plurality of resistive tracks (tracking or traces). The resistive tracks may be copper. The heating element may be an etched foil. The heating element may be a heating wire. The heating wire may be nichrome. The heating element may be a positive thermal coefficient of resistance (PTC) ceramic. The PTC ceramic may be barium titanate. The heating element may be a thermoelectric device. The thermoelectric device may be a Peltier device. The wicking surface may be provided by an over-molding on the circuit board, the over-molding having micro-channels. The heating surface temperature may be measured, at least in part, by determining a resistance level or other characteristic of the heating element. The resistance level of the heating element may be used to indicate an average temperature of the heating surface. The heating element may be arranged to deliver a higher power density in a specified region of the heating element as compared to a power density delivered to other regions of the heating element. The specified higher density region of the heating element may be located at an outlet of a water supply to the heating surface. The specified higher density region of the heating element may be located at a water pre-heating area on the heating surface. The respiratory humidification system may include a temperature sensor at the outlet location of the gases channel.

According to another aspect of the present disclosure, there is provided a respiratory humidification system comprising a gases channel through which gases may flow, the gases channel extending between an inlet location and an outlet location, the gases channel including a humidification location between the inlet and outlet locations; a gases pre-heater disposed within the gases channel between the inlet and the humidification locations; and a heating surface in fluid communication with the gases channel at the humidification location, the heating surface having a wicking element configured to distribute water to the heating surface.

The respiratory humidification system may have a gases flow generator adapted to propel, drive, or otherwise cause gases to move in a general direction from the inlet location to the outlet location of the gases channel. The gases pre-heater may include a gases heating element. The gases heating element may be a printed circuit board. The printed circuit board may have resistive elements. The gases heating element may be an etched foil film. The gases heating element may be a heating coil. The gases heating element may be a PTC ceramic. The respiratory humidification system may have a temperature sensor. The temperature sensor may be positioned in the gases channel downstream of the gases pre-heater. The temperature sensor may be positioned in the gases channel upstream of the gases pre-heater. A characterization (e.g., resistance) of the gases heating element may be used to determine a temperature of the gases. Control of a power level delivered to the gases heating element may be based on information provided by the temperature sensor positioned in the gases channel downstream of the gases pre-heater. Control of the power level delivered to the gases heating element may be based on information provided by a gases flow sensor and by the temperature sensor positioned in the gases channel upstream of the gases pre-heater. A desired downstream temperature of the gases may be determined based on an evaporation rate of the water from the heating surface. The desired downstream temperature of the gases may be set to ensure that substantially all sensible heat is supplied by the gases pre-heater. The desired downstream temperature of the gases may be set to obtain a desired relative humidity level of the gases at the outlet location. The desired downstream temperature of the gases may be set to be between 0° C. and approximately 5° C. above desired temperature of the gases at the outlet location. The desired downstream temperature of the gases may be set to be a desired dew point temperature at the outlet location. The desired downstream temperature of the gases may be set to approximately 25° C. to approximately 43° C., or approximately 31° C. to approximately 43° C., or approximately 31° C. to approximately 41° C., or approximately 31° C. to approximately 37° C., or approximately 37° C. The heating surface may include a heating element configured to provide heat to the heating surface. The heating element may include a plurality of resistive tracks (tracking or traces). The respiratory humidification system may include a water flow generator configured to generate a flow of water to the heating surface. The water flow generator may include a pump. The pump may be a positive displacement pump. The positive displacement pump may be a piezoelectric diaphragm pump, a peristaltic pump, a micro-pump, or a progressive cavity pump. The respiratory humidification system may include an apparatus for pre-heating the water. The apparatus for pre-heating the water may be incorporated into the heating element by increasing a density of resistive tracks, and therefore the power density delivered to the heating surface, at one or more areas of the heating element corresponding to areas on the heating surface where the water is introduced. The respiratory humidification system may include a water supply line configured to deliver water to the heating surface. The apparatus for pre-heating the water may be incorporated into the water supply line.

The wicking element may include absorptive fabric. The wicking element may include absorptive paper. The wicking element may include micro-channels. The wicking element may include a hydrophilic coated surface. The wicking element may include a plurality of capillary/contact wicks. The wicking element may include a thin, porous media, such as a fibrous, porous, or sintered polymer. The wicking element may include a coupling, or be coupled with a coupling, that performs some of the water distribution to the heating surface. The coupling may be a length of wicking media bonded to or otherwise brought into contact with the wicking element or heating surface. The coupling may be a porous polymer. The coupling may be a fabric. The coupling may be a paper. The coupling may be a hydrophilic coated section. The coupling may be a second surface forming an acute angle with the wicking element. The second surface may be a glass plate. The coupling may be a cavity in contact with the wicking element. The coupling may be performed by a line source. The coupling may be performed by multiple line sources. The coupling may be performed by a point source. The coupling may be performed by multiple point sources. The coupling may be performed by a radial source. The coupling may be performed by multiple radial sources. The coupling may be performed by a combination of line sources, point sources, and/or radial sources. The heating surface may be adapted to maintain a temperature of between approximately 30° C. and approximately 99.9° C. The heating surface may be adapted to maintain a temperature of between approximately 35° C. and approximately 90° C. The heating surface may be adapted to maintain a temperature of between approximately 40° C. and approximately 80° C. The heating surface may be adapted to maintain a temperature of between approximately 45° C. and approximately 70° C. The heating surface may be adapted to maintain a temperature of between approximately 45° C. and approximately 60° C. The heating surface may be adapted to maintain a temperature of between approximately 50° C. and approximately 60° C. The heating surface may be adapted to be maintained at a temperature of approximately 50° C. The respiratory humidification system may be mechanically configured such that the wicking element, the heating surface, and the water flow generator are positioned within, or incorporated as part of, the gases channel. The respiratory humidification system may be mechanically configured such that the water flow generator, the coupling, the wicking element, and the heating surface are positioned within, or incorporated as part of, the gases channel. The respiratory humidification system may include a filter. The filter may be in a water line. The filter may be positioned downstream of the pump. The filter may be positioned at an inlet to the heating surface. The filter may be a biologic filter. The respiratory humidification system may include a plurality of filters. The respiratory humidification system may include a first filter in a water line between the reservoir and the water flow generator and a second filter in a water line between the water flow generator and the heating surface. The respiratory humidification system may include an electromagnetic radiation emitter for sterility. The electromagnetic radiation emitter may be a UV light source. The UV light source may be a lamp or light emitting diode (LED).

According to another aspect of the present disclosure, there is provided a respiratory humidification system comprising a gases channel through which gases may flow, the gases channel extending between an inlet location and an outlet location, the gases channel including a humidification location between the inlet and outlet locations; a water flow metering system configured to meter water at a water flow rate; a heating surface in fluid communication with the gases channel at the humidification location, the heating surface configured to receive the water provided by the water flow metering system and to vaporize the received water; at least one temperature sensor configured to measure a temperature of the heating surface; two or more fluid sensors positioned at, on, adjacent or proximal to two or more regions of the heating surface, the two or more sensors configured to detect if the heating surface is wetted in the two or more regions; a water flow controller configured to control the water flow rate to the heating surface; where in use, the respiratory humidification system deterministically controls a humidity level of the gases at the outlet location by controlling the water flow rate to the heating surface.

The water flow metering system may include a pump. The pump may be a positive displacement pump. The positive displacement pump may be a piezoelectric diaphragm pump, a peristaltic pump, a micro-pump, or a progressive cavity pump. The pump may be a pressure feed, such as a gravity feed, in series with a control valve. The respiratory humidification system may have a conduit in fluid communication with the water flow metering system, the conduit configured to carry water to the water flow metering system. The conduit may have a non-return valve configured to keep the water flow metering system primed. The conduit may have a non-return valve configured to keep the pump primed. The water flow metering system may include a wicking structure that employs capillary action to controllably meter the water to a wicking surface on the heating surface. The conduit may have a safety valve, such as a pressure relief valve, in the conduit leading to the water flow metering system. The respiratory humidification system may have a reservoir configured to hold water. The respiratory humidification system may have a flow restriction device positioned between the reservoir and the water flow metering system to prevent gravity-driven flow from influencing the water flow path. The flow restriction device may be an elastic protrusion that squeezes or otherwise restricts the flow path. The water flow metering system may be a pump in an open-loop configuration. The water flow metering system may be a pump or a flow actuator in series with a flow sensor in a closed-loop configuration. The water flow metering system may provide a continuous flow of water in the range of 0 mL/min to approximately 5 mL/min. The water flow metering system may provide a continuous flow of water in the range of approximately 40 µL/min to approximately 4 mL/min. The water flow metering system may provide a continuous flow of water in the range of approximately 70 µL/min to approximately 2.5 mL/min. The water flow metering system may provide a flow rate of water at an accuracy of approximately ±15%. The water flow metering system may provide a flow rate of water at an accuracy of approximately ±10%. The water flow metering system may provide a flow rate of water at an accuracy of approximately ±6.5%. The water flow metering system may provide a flow rate of water at an accuracy of approximately ±5%.

Control of the water flow rate to the heating surface may be based on a flow rate of the gases in the gases channel. Control of the water flow rate to the heating surface may be based on an evaporation rate of the water from the heating surface. Control of the water flow rate to the heating surface may be based on a temperature of the heating surface wherein the temperature of the heating surface is maintained at a constant temperature. Control of the water flow rate to the heating surface may be based on a temperature of the heating surface wherein the temperature of the heating surface is controlled. Control of the water flow rate to the heating surface may be based on an absolute or barometric pressure of the gases at or near the inlet location. Control of the water flow rate to the heating surface may be based on a dew point temperature of the gases at the inlet location. Control of the water flow rate to the heating surface may be based on an enthalpy provided by the heating surface. Control of the water flow rate to the heating surface may be based on a power level provided by the heating surface. Control of the water flow rate to the heating surface may be based on a temperature of the gases at the inlet location. The dew point temperature of the gases at the inlet location may be derived by processing information provided by a temperature sensor and a humidity sensor. Control of the water flow rate to the heating surface may be based on the dew point temperature of the gases at the inlet location. Control of the water flow rate to the heating surface may be based on a relative humidity level of the gases at the inlet location. Control of the water flow rate to the heating surface may be based on an effective heating area of the heating surface. Control of the water flow rate to the heating surface may be based on a pressure level of the gases in the gases channel. Control of the water flow rate to the heating surface may be based on a velocity of the gases flowing in the gases channel. Control of the water flow rate to the heating surface may be based on a temperature of the water flow.

The respiratory humidification system may include a water temperature sensor. The respiratory humidification system may include a gases flow rate sensor. The respiratory humidification system may determine the water flow rate based on a model. The respiratory humidification system may determine the gases flow rate based on a model. The respiratory humidification system may include an ambient pressure sensor. The pressure sensor may be positioned at or near the heater surface. The respiratory humidification system may include an ambient dew point temperature sensor positioned within the gases channel upstream of the humidification location. The respiratory humidification system may include an ambient humidity sensor positioned within the gases channel upstream of the humidification location. The respiratory humidification system may include a gases pre-heater. The gases pre-heater may be disposed within the gases channel between the inlet and the humidification locations. The ambient dew point temperature sensor may be positioned within the gases channel upstream of the gases pre-heater. The ambient humidity sensor may be positioned within the gases channel upstream of the gases pre-heater. The ambient dew point temperature sensor may be positioned within the gases channel downstream of the gases pre-heater. The ambient humidity sensor may be positioned within the gases channel downstream of the gases pre-heater. The ambient dew point temperature sensor may be positioned within the gases channel downstream of the gases pre-heater in combination with a temperature sensor positioned at the inlet location of the gases channel.

The at least one temperature sensor may be configured to determine a proportion of the heating surface that is saturated with water. The respiratory humidification system may control a gases temperature at the inlet location of the gases channel by controlling a power level to the gases pre-heater in an open loop manner. The respiratory humidification system may include a water pre-heater. The two or more fluid sensors may be used to prevent overflow of liquid from the heating surface. Control of the water flow rate to the heating surface may be based information provided by the two or more fluid sensors. The two or more fluid sensors may be used to control an evaporative area on the heating surface. The two or more fluid sensors may be used exclusively to control the evaporative area on the heating surface. The two or more fluid sensors may be temperature sensors. The two or more fluid sensors may be resistive or capacitive sensors.

According to another aspect of the present disclosure, there is provided a heater plate for a respiratory humidification system, the heater plate having a plurality of resistive tracks, the heater plate being over-molded with a surface that includes micro-channels. The heater plate may comprise a printed circuit board (PCB). The heater plate may comprise an etched foil. The micro-channels may include an arrangement of parallel channels configured to direct water flow in one direction. The over-molded surface may include a set of distribution channels connected to a set of wicking channels, wherein there are fewer distribution channels than there are wicking channels. The micro-channels may be distributed radially from a single point.

According to another aspect of the present disclosure, there is provided a respiratory therapy system comprising a gases channel through which gases may flow, the gases channel extending between an inlet location and an outlet location; a gases pre-heater disposed within the gases channel; a humidification assembly disposed within and in fluid communication with the gases channel, the humidification assembly including: a heating surface in fluid communication with the gases, the heating surface having a wicking element configured to distribute water to the heating surface; a coupling configured to distribute the water to the wicking element; a water flow controller, in fluid communication with the coupling, the water flow controller configured to meter the water to the coupling, the water flow controller comprising a pump and a flow sensor, the water flow controller configured to control a water flow rate, wherein use, the wicking element distributes the metered water to at least a portion of the heating surface, and the heating surface causes the distributed water to be vaporized into the gases. The heating surface may have heat provided to it by a circuit board. The circuit board may be a printed circuit board. The circuit board may have a plurality of resistive tracks. The resistive tracks may be copper. The wicking surface may be provided by an over-molding on the circuit board. The over-molding may have micro-channels in it. The over-molding may be a thermoplastic material. The heating surface may have modular zones. The heating surface may have a first zone configured to pre-heat the water and a second zone configured to vaporize the water.

The water flow controller can include a metering arrangement. The metering arrangement can further include a pump. The pump can be a positive displacement pump, such as, for example, a piezoelectric diaphragm pump, a peristaltic pump, a micro-pump, or a progressive cavity pump. The pump can also be a pressure feed, such as a gravity feed, in series with a control valve. The respiratory humidification system may have a conduit in fluid communication with the metering arrangement, the conduit configured to carry water to the metering arrangement. The conduit can have a non-return valve configured to keep the metering arrangement primed. The conduit can also have a non-return valve configured to keep the pump primed. The metering arrangement can include a wicking structure that employs capillary action to controllably meter the water to the wicking element and/or to the heating surface. The conduit can also have a safety valve, such as a pressure relief valve, in the conduit leading to the metering arrangement. The respiratory humidification system can have a reservoir configured to hold water. The respiratory humidification system can also have a flow restriction device positioned between the reservoir and the metering arrangement to prevent gravity-driven flow from influencing the water flow path. The flow restriction device can be an elastic protrusion that squeezes or otherwise restricts the flow path. The water flow controller may be a pump in an open-loop configuration. The water flow controller may be a pump or a flow actuator in series with a flow sensor in a closed-loop configuration. The water flow controller may provide a continuous flow of water in the range of 0 mL/min to approximately 5 mL/min. The water flow controller may provide a continuous flow of water in the range of approximately 40 µL/min to approximately 4 mL/min. The water flow controller may provide a continuous flow of water in the range of approximately 70 µL/min to approximately 2.5 mL/min. The water flow controller may provide a flow rate of water at an accuracy of approximately ±15%. The water flow controller may provide a flow rate of water at an accuracy of approximately ±10%. The water flow controller may provide a flow rate of water at an accuracy of approximately ±6.5%. The water flow controller may provide a flow rate of water at an accuracy of approximately ±5%.

The heating surface can be configured to be maintained at a temperature range. The temperature range may be between approximately 30° C. and approximately 99.9° C. The temperature range may be between approximately 35° C. and approximately 90° C. The temperature range may be between approximately 40° C. and approximately 80° C. The temperature range may be between approximately 45° C. and approximately 70° C. The temperature range may be between approximately 45° C. and approximately 60° C. The temperature range may be between approximately 50° C. and approximately 60° C. The heating surface may be configured to maintain a temperature of approximately 50° C. The heating surface may include a wicking surface. The heating surface may include a heating element configured to provide heat to the heating surface. The heating element may be a circuit board. The circuit board may be a printed circuit board. The circuit board may be a flexible circuit board. The flexible circuit board may be made of polymer. The polymer may be silicone, polyester, or polyimide. The circuit board may have a plurality of resistive tracks. The resistive tracks may be copper. The heating element may be an etched foil. The heating element may be a heating wire. The heating wire may be nichrome. The heating element may be a positive thermal coefficient of resistance (PTC) ceramic. The PTC ceramic may be barium titanate. The heating element may be a thermoelectric device. The thermoelectric device may be a Peltier device. The wicking surface may be provided by an over-molding on the circuit board, the over-molding having micro-channels. The heating surface temperature may be measured, at least in part, by determining a resistance level or other characteristic of the heating element. The resistance level of the heating element may be used to indicate an average temperature of the heating surface. The heating element may be arranged to deliver a higher power density in a specified region of the heating element as compared to a power density delivered to other regions of the heating element. The specified higher density region of the heating element may be located at an outlet of a water supply to the heating surface. The specified higher density region of the heating element may be located at a water pre-heating area on the heating surface. The respiratory humidification system may include a temperature sensor at the outlet location of the gases channel.

The respiratory humidification system may have a gases flow generator adapted to propel, drive, or otherwise cause gases to move in a general direction from the inlet location to the outlet location of the gases channel. The gases pre-heater may include a gases heating element. The gases heating element may be a printed circuit board. The printed circuit board may have resistive elements. The gases heating element may be an etched foil film. The gases heating element may be a heating coil. The gases heating element may be a PTC ceramic. The respiratory humidification system may have a temperature sensor. The temperature sensor may be positioned in the gases channel downstream of the gases pre-heater. The temperature sensor may be positioned in the gases channel upstream of the gases pre-heater. A characterization (e.g., resistance) of the gases heating element may be used to determine a temperature of the gases. Control of a power level delivered to the gases heating element may be based on information provided by the temperature sensor positioned in the gases channel downstream of the gases pre-heater. Control of the power level delivered to the gases heating element may be based on information provided by a gases flow sensor and by the temperature sensor positioned in the gases channel upstream of the gases pre-heater. A desired downstream temperature of the gases may be determined based on an evaporation rate of the water from the heating surface. The desired downstream temperature of the gases may be set to ensure that all sensible heat is supplied by the gases pre-heater. The desired downstream temperature of the gases may be set to obtain a desired relative humidity level of the gases at the outlet location. The desired downstream temperature of the gases may be set to be between 0° C. and approximately 5° C. above a desired temperature of the gases at the outlet location. The desired downstream temperature of the gases may be set to be a desired dew point temperature at the outlet location. The desired downstream temperature of the gases may be set to approximately 25° C. to approximately 43° C., or approximately 31° C. to approximately 43° C., or approximately 31° C. to approximately 41° C., or approximately 31° C. to approximately 37° C., or approximately 37° C.

The respiratory humidification system may include a filter. The filter may be in a water line. The filter may be positioned downstream of the pump. The filter may be positioned at an inlet to the heating surface. The filter may be a biologic filter. The respiratory humidification system may include a plurality of filters. The respiratory humidification system may include a first filter in a water line between the reservoir and the water flow generator and a second filter in a water line between the water flow generator and the heating surface. The respiratory humidification system may include an electromagnetic radiation emitter for sterility. The electromagnetic radiation emitter may be a UV light source. The UV light source may be a lamp or an LED.

According to another aspect of the present disclosure, there is provided a respiratory humidification system configured to evaporate water, the respiratory humidification system configured to output power, wherein the output power is transferred into heat in the water. The respiratory humidification system may be configured such that between approximately 80% and approximately 99.9% of the power output is transferred into heat in the water. The respiratory humidification system may be configured such that between approximately 85% and approximately 99.9% of the power output is transferred into heat in the water. The respiratory humidification system may be configured such that between approximately 90% and approximately 99.9% of the power output is transferred into heat in the water. The respiratory humidification system may be configured such that approximately 98% of the power output is transferred into heat in the water. The heating surface may be adapted to maintain a temperature of between approximately 30° C. and approximately 99.9° C. The heating surface may be adapted to maintain a temperature of between approximately 35° C. and approximately 90° C. The heating surface may be adapted to maintain a temperature of between approximately 40° C. and approximately 80° C. The heating surface may be adapted to maintain a temperature of between approximately 45° C. and approximately 70° C. The heating surface may be adapted to maintain a temperature of between approximately 45° C. and approximately 60° C. The heating surface may be adapted to maintain a temperature of between approximately 50° C. and approximately 60° C. The heating surface may be adapted to maintain a temperature of approximately 50° C.

According to another aspect of the present disclosure, there is provided a respiratory humidification system comprising a gases channel through which gases may flow, the gases channel extending between an inlet location and an outlet location, the gases channel including a humidification location between the inlet and outlet locations; a gases pre-heater disposed within the gases channel between the inlet and the humidification locations; a heating surface in fluid communication with the gases channel at the humidification location; a water flow generator, in fluid communication with the heating surface, the water flow generator configured to meter water to the heating surface.

The heating surface may be adapted to maintain a temperature of between approximately 30° C. and approximately 99.9° C. The heating surface may be configured to maintain a temperature of between approximately 35° C. and approximately 90° C. The heating surface may be configured to maintain a temperature of between approximately 40° C. and approximately 80° C. The heating surface may be configured to maintain a temperature of between approximately 45° C. and approximately 70° C. The heating surface may be configured to maintain a temperature of between approximately 45° C. and approximately 60° C. The heating surface may be configured to maintain a temperature of between approximately 50° C. and approximately 60° C. The heating surface may be adapted to maintain a temperature of approximately 50° C.

The respiratory humidification system may have a gases flow generator adapted to propel, drive, or otherwise cause gases to move in a general direction from the inlet location to the outlet location of the gases channel. The gases pre-heater may include a gases heating element. The gases heating element may be a printed circuit board. The printed circuit board may have resistive elements. The gases heating element may be an etched foil film. The gases heating element may be a heating coil. The gases heating element may be a PTC ceramic. The respiratory humidification system may have a temperature sensor. The temperature sensor may be positioned in the gases channel downstream of the gases pre-heater. The temperature sensor may be positioned in the gases channel upstream of the gases pre-heater. A characterization (e.g., resistance) of the gases heating element may be used to determine a temperature of the gases. Control of a power level delivered to the gases heating element may be based on information provided by the temperature sensor positioned in the gases channel downstream of the gases pre-heater. Control of the power level delivered to the gases heating element may be based on information provided by a gases flow sensor and by the temperature sensor positioned in the gases channel upstream of the gases pre-heater. A desired downstream temperature of the gases may be determined based on an evaporation rate of the water from the heating surface. The desired downstream temperature of the gases may be set to ensure that all sensible heat is supplied by the gases pre-heater. The desired downstream temperature of the gases may be set to obtain a desired relative humidity level of the gases at the outlet location. The desired downstream temperature of the gases may be set to be between 0° C. and approximately 5° C. above a desired temperature of the gases at the outlet location. The desired downstream temperature of the gases may be set to be a desired dew point temperature at the outlet location. The desired downstream temperature of the gases may be set to approximately 25° C. to 43° C., or approximately 31° C. to 43° C., or approximately 31° C. to 41° C., or approximately 31° C. to 37° C., or approximately 37° C. The heating surface may include a heating element configured to provide heat to the heating surface. The heating element may include a plurality of resistive tracks.

The water flow generator may include a pump. The pump may be a positive displacement pump. The positive displacement pump may be a piezoelectric diaphragm pump, a peristaltic pump, a micro-pump, or a progressive cavity pump. The respiratory humidification system may include an apparatus for pre-heating the water. The apparatus for pre-heating the water may be incorporated into the heating element by increasing a density of resistive tracks (traces or tracking), and therefore the power density delivered to the heating surface, at one or more areas of the heating element corresponding to areas on the heating surface where the water is introduced. The respiratory humidification system may include a water supply line configured to deliver water to the heating surface. The apparatus for pre-heating the water may be incorporated into the water supply line.

According to another aspect of the present disclosure, there is provided a respiratory humidification system comprising a gases channel through which gases may flow, the gases channel extending between an inlet location and an outlet location; a heating surface in fluid communication with the gases channel; and a water flow controller configured to control a water flow rate of water delivered to the heating surface; wherein in use, a humidity level of the gases at the outlet location is deterministically controlled by controlling the water flow rate. The respiratory humidification system may include a water flow sensor. Control of the water flow rate may be based on a flow rate of the gases in the gases channel. Control of the water flow rate may be based on an evaporation rate of the water from the heating surface. Control of the water flow rate may be based on a temperature of the heating surface wherein the temperature of the heating surface is maintained at a constant temperature. Control of the water flow rate may be based on a temperature of the heating surface wherein the temperature of the heating surface is controlled. Control of the water flow rate may be based on an absolute or barometric pressure of the gases at or near the inlet location. Control of the water flow rate may be based on a dew point temperature of the gases at the inlet location. The dew point temperature of the gases at the inlet location may be derived by processing information provided by a temperature sensor and a humidity sensor. Control of the water flow rate may be based on an enthalpy provided by the heating surface. Control of the water flow rate may be based on a power level provided by the heating surface. Control of the water flow rate may be based on a temperature of the gases at the inlet location. Control of the water flow rate may be based on a relative humidity level of the gases at the inlet location. Control of the water flow rate may be based on an effective heating area of the heating surface. Control of the water flow rate may be based on a pressure level of the gases in the gases channel. Control of the water flow rate may be based on a velocity of the gases flowing in the gases channel. Control of the water flow rate may be based on a temperature of the water flow. The respiratory humidification system may include a water temperature sensor. The respiratory humidification system may include a gases flow rate sensor. The respiratory humidification system may determine the water flow rate based on a model. The respiratory humidification system may determine the gases flow rate based on a model. The respiratory humidification system may include a pressure sensor. The respiratory humidification system may include an ambient pressure sensor. The pressure sensor may be positioned at or near the heater surface. The respiratory humidification system may include a temperature sensor configured to measure a temperature of the heating surface. The respiratory humidification system may include an ambient dew point temperature sensor positioned within the gases channel upstream of the humidification location. The respiratory humidification system may include an ambient humidity sensor positioned within the gases channel upstream of the humidification location. The respiratory humidification system may include a gases pre-heater. The gases pre-heater may be disposed within the gases channel near the inlet location. The ambient dew point temperature sensor may be positioned within the gases channel upstream of the gases pre-heater. The ambient humidity sensor may be positioned within the gases channel upstream of the gases pre-heater. The ambient dew point temperature sensor may be positioned within the gases channel downstream of the gases pre-heater. The ambient humidity sensor may be positioned within the gases channel downstream of the gases pre-heater. The ambient dew point temperature sensor may be positioned within the gases channel downstream of the gases pre-heater in combination with a temperature sensor positioned at the inlet location of the gases channel. The respiratory humidification system may include at least one temperature sensor configured to measure at least one temperature of the heating surface. The at least one temperature sensor may be configured to determine a proportion of the heating surface that is saturated with water. The respiratory humidification system may control a gases temperature at or near the inlet location of the gases channel by controlling a power level to the gases pre-heater in an open loop manner. The respiratory humidification system may include a water pre-heater.

According to another aspect of the present disclosure, there is provided a humidification system positioned within an inspiratory tube of a respiratory therapy system.

BRIEF DESCRIPTION OF THE DRAWINGS

Various embodiments of the present disclosure will now be described, by way of illustrative example only, with reference to the accompanying drawings. In the drawings, similar elements have like reference numerals.

DETAILED DESCRIPTION

Figure 1A:
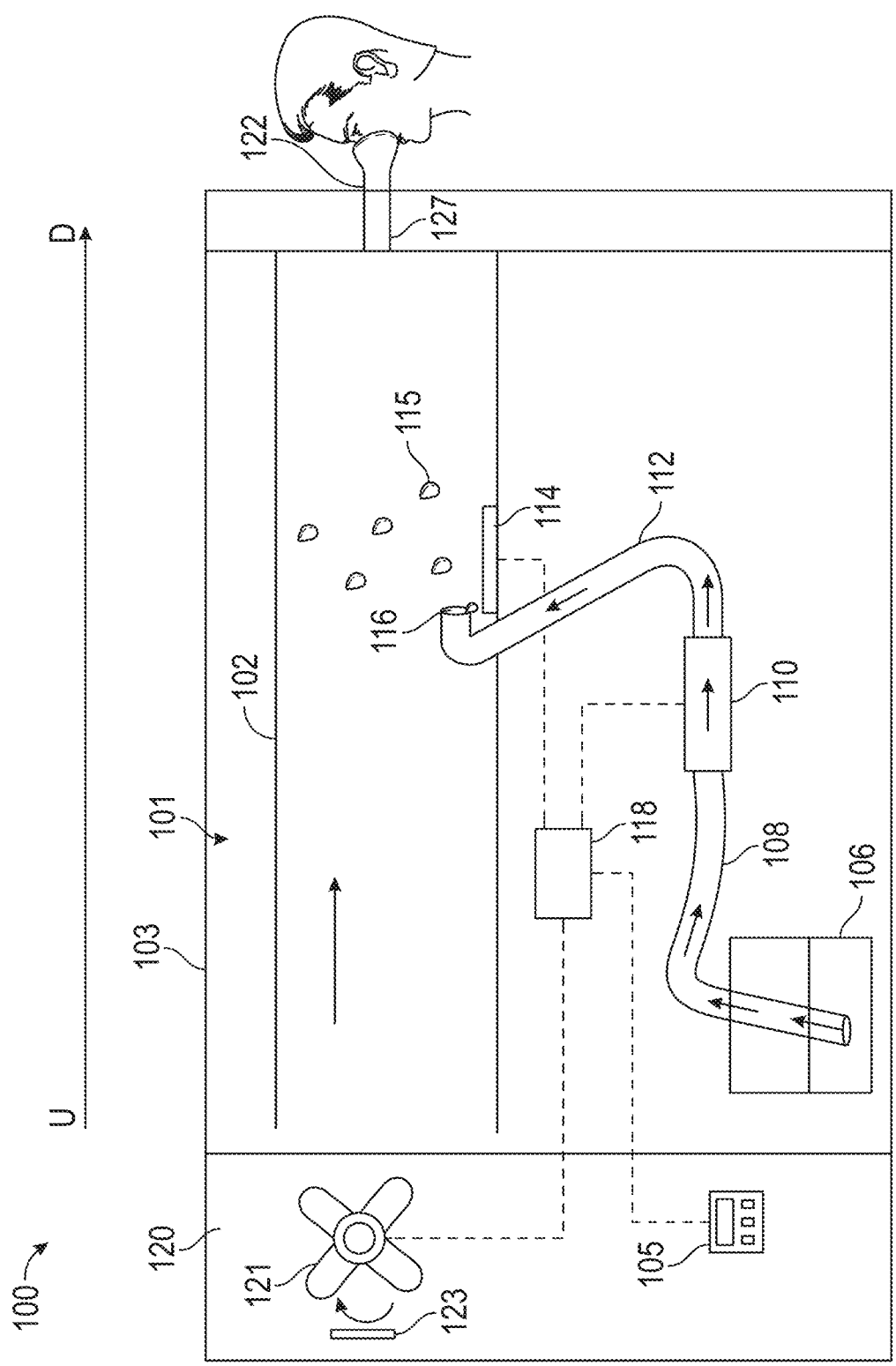
FIGS. 1A-1E are schematic diagrams of various embodiments of respiratory therapy systems.

The following description is merely illustrative in nature and is in no way intended to limit the disclosure, its application, or uses. For purposes of clarity, the same reference numbers will be used in the drawings to identify similar elements. However, for the sake of convenience, certain features present or annotated with reference numerals in some figures of the present disclosure are not shown or annotated with reference numerals in other figures of the present disclosure. Unless the context clearly requires otherwise, these omissions should not be interpreted to mean that features omitted from the drawings of one figure could not be equally incorporated or implemented in the configurations of the disclosed methods, apparatus and systems related to or embodied in other figures. Conversely, unless the context clearly requires otherwise, it should not be assumed that the presence of certain features in some figures of the present disclosure means that the disclosed methods, apparatus and systems related to or embodied in such figures must necessarily include these features.

Certain features, aspects, and advantages of the present disclosure include the realization of an on-demand humidifier, where the requisite amount of water (or other humidification fluid) is metered onto a heated surface, evaporated and mixed with a pre-heated gases source to produce a desired humidity level, in an open-loop and deterministic configuration. Advantageously, by employing the disclosed humidification control systems, devices, and methods, allocated water can be deposited onto a heating element that is in fluid communication with a gases channel on an as-needed basis as opposed to heating an entire fluid supply at once, or heating an otherwise excess volume of liquid, such as a chamber of liquid. Illustratively, by measuring an inlet gases flow rate, an inlet gases dew point temperature, and/or a gases channel pressure level, a fluid flow rate of liquid to a heating surface may be determined and controlled to achieve a desired output humidity and temperature level (or outlet dew point temperature) of gases to be delivered to the patient.

With reference to FIG. 1A, a non-limiting exemplary configuration of a respiratory therapy system 100 is shown. In the illustrated configuration, the respiratory therapy system 100 includes a flow generator 120. The flow generator 120 can have, for example, a blower 121 adapted to propel gases through the respiratory therapy system 100. The gases propelled using the blower 121 may, for example, include air received from the environment outside of the respiratory therapy system 100 (for example, 'ambient air' or 'ambient gases') and/or gases from a gases container in communication with the respiratory therapy system 100 (see for example gases reservoir 137 in FIG. 1E). Gases from the flow generator 120 are directed to and/or through a respiratory humidification system 101 adapted to add moisture to the gases. The respiratory humidification system 101 includes a gases channel 102 (which may also be referred to herein as "a breathing tube," or "an inspiratory tube") adapted to receive gases from the flow generator 120 and/or another gases source and channel the gases to an outlet, such as a patient interface 122. As indicated using the $\overrightarrow{UD}$ (or Upstream-Downstream) vector at the top of FIG. 1A, in use, gases may generally move from the flow generator 120 to the respiratory humidification system 101 (for example, through the gases channel 102), and from the respiratory humidification system 101 to the outlet or patient interface 122 (for example, through the gases channel 102) in a downstream direction.

With further reference to the non-limiting exemplary configuration shown in FIG. 1A, the respiratory humidification system 101 includes a fluid reservoir 106 which in use houses a fluid. "Fluid" in this context may refer to liquids or fluent solids suitable for humidifying respiratory gases and may include, for example, water. The fluid may be a water with additives that are more volatile than water. The fluid reservoir 106 is fluidly or otherwise physically linked to a metering arrangement (also referred to as a liquid flow controller or water flow controller herein) 110. The metering arrangement 110 is configured to meter fluid from the fluid reservoir 106 to a humidification housing 115 located in the gases channel 102 or outside of, but in pneumatic communication with, the gases channel 102. The metering arrangement 110 can further include a pump. The pump can be a positive displacement pump, such as, for example, a piezoelectric diaphragm pump, a peristaltic pump, a micro-pump, or a progressive cavity pump. The pump can also be a pressure feed, such as a gravity feed in series with a control valve (for example, as shown in FIG. 1D and described below). The metering arrangement can include a wicking structure that employs capillary action to controllably meter the water to the wicking element and/or to the heating surface.

As mentioned above, the metering arrangement 110 can be referred to as a water flow controller. The water flow controller may be a pump in an open-loop configuration. The water flow controller may be a pump or a flow actuator in series with a flow sensor in a closed-loop configuration. In some configurations, a water flow controller configured as a pump in an open-loop configuration is preferred because it is simpler and only requires one part (the pump). However, a pump in an open-loop configuration may not be able to deliver water accurately, but may still be useful under conditions where accuracy is not essential. Therefore, in other configurations, a pump or a flow actuator in series with a flow sensor in a closed-loop configuration can be used where greater accuracy is desired. In this configuration, the selection of the pump may be less important as it does not have to be accurate, and a dedicated flow sensor is used to control accuracy. Another advantage to a pump or a flow actuator in series with a flow sensor in a closed-loop configuration is that it provides two independent indications of flow (the pump setting and the sensed flow) which adds a layer of safety to the system (for example, the pump and sensor can be compared against each other to verify they are operating correctly).

The water flow controller may provide a continuous flow of water in the range of 0 mL/min to approximately 10 mL/min. The water flow controller may provide a continuous flow of water in the range of 0 mL/min to approximately 7 mL/min. The water flow controller may provide a continuous flow of water in the range of 0 mL/min to approximately 5 mL/min. The water flow controller may provide a continuous flow of water in the range of approximately 40 μL/min to approximately 4 mL/min. The water flow controller may provide a continuous flow of water in the range of approximately 70 μL/min to approximately 2.5 mL/min. The water flow controller may provide a flow rate of water at an accuracy of approximately ±15%. The water flow controller may provide a flow rate of water at an accuracy of approximately ±10%. The water flow controller may provide a flow rate of water at an accuracy of approximately ±6.5%. The water flow controller may provide a flow rate of water at an accuracy of approximately ±5%.

The water flow controller, including metering system 110, may be configured to ensure that the surface of the heating element 114 is entirely wetted (saturated). A fully wetted surface may allow for improved deterministic control of the humidity. The wetted surface also means that humidity can be increased more quickly as water travels more quickly over a wet surface than it does over a dry surface.

Any positive displacement pump may be used in the water controller or metering arrangement 110. Positive displacement pumps work by displacing a fixed volume of water and generally yield good accuracy. Any of a variety of positive displacement pumps are suitable, for example, peristaltic, diaphragm, vane, plunger, etc., and a majority of these can be scaled to work at the flow rates contemplated herein. However, piezoelectric micro-pumps (miniature diaphragm pumps using piezoelectric elements as the actuators) and peristaltic pumps (which use rollers to squeeze water through a tube at a constant rate) may be particularly advantageous as many are already commercially available at sizes, prices, operating ranges and powers, etc., that are suitable for the systems described herein. Additionally, a pressure feed, such as a gravity feed, in series with a control valve (see FIG. 1D) and/or wicking/capillary action may be used in place of a pump. In some configurations, an electro/magneto-hydrodynamic pump may be used.

When the water flow controller includes a flow sensor, in some configurations, the flow sensor may be a thermal mass meter. These sensors work by heating the liquid and measuring either the power required to do so (for example, a heated flow bead) or the temperature gradient introduced, or some variation on this. Alternatively, the flow sensor may be replaced or supplemented with a drip feed (for example, counting drops as is a common method of measuring flow in an IV drip); differential pressure sensors that measure the pressure drop across a restriction to calculate flow; and/or positive displacement sensors that use the same principle as the positive displacement pump to sense flow. By way of non-limiting example, a suitable pump is the mp6 micro pump available from Bartels Mikrotechnik. An example liquid flow sensor is the LG16 available from Sinsiron, the data sheet of which is incorporated herein by reference.

The fluid reservoir 106 is connected to the metering arrangement 110 via a first fluid conduit 108. The first conduit 108 can have a non-return valve configured to keep the metering arrangement primed. The first conduit 108 can also have a non-return valve configured to keep the pump primed. The first conduit 108 can also have a safety valve, such as a pressure relief valve, in the conduit leading to the metering arrangement to prevent flow of liquid in case of pump or water controller failure. The respiratory humidification system 101 can also have a flow restriction device positioned between the reservoir 106 and the metering arrangement 110 to prevent gravity-driven flow from influencing the water flow path. The flow restriction device can be an elastic protrusion that squeezes or otherwise restricts the flow path. The metering arrangement 110 meters fluid to the humidification housing 115 through a second fluid conduit 112. In particular, the metered fluid can enter the humidification housing 115 through inlets 116 to the humidification housing 115.

A heating device 114 may be present in, at, or near the humidification housing 115. The heating device 114 can have a wicking element configured to distribute the metered fluid to the heating device 114. In some configurations, the wicking element is configured to wick the metered fluid evenly across the surface of the heating device 114. The heating device 114 may be configured to vaporize the metered fluid such that it becomes entrained in the gases flow in use by the respiratory therapy system 100. The heating device 114 can be configured to be maintain a heating surface at a temperature range. The temperature range may be between approximately 30° C. and approximately 99.9° C. The temperature range may be between approximately 35° C. and approximately 90° C. The temperature range may be between approximately 40° C. and approximately 80° C. The temperature range may be between approximately 45° C. and approximately 70° C. The temperature range may be between approximately 45° C. and approximately 60° C. The temperature range may be between approximately 50° C. and approximately 60° C. The heating surface may be configured to maintain a temperature of approximately 50° C. "Approximately" should be understood herein to be within an acceptable tolerance of the specified degree such as, for example, ±3° C. The heating surface may include a wicking surface. The heating surface may include a heating element configured to provide heat to the heating surface. The heating element may be a circuit board. The circuit board may be a printed circuit board (for example, as shown and described in reference to FIGS. 4A-4C below). The circuit board may be a flexible circuit board. The flexible circuit board may be made of aluminum-polyimide. The circuit board may have a plurality of resistive tracks. The resistive tracks may be copper. The heating element may be an etched foil (for example, as shown and described in reference to FIGS. 4D-4E below). The heating element may be a heating wire. The heating wire may be nichrome. The heating element may be a positive thermal coefficient of resistance (PTC) ceramic. The PTC ceramic may be barium titanate. The heating element may be a thermoelectric device. The thermoelectric device may be a Peltier device. The wicking surface may be provided by an over-molding on the circuit board, the over-molding having micro-channels. The heating surface temperature may be measured, at least in part, by determining a resistance level or other characteristic of the heating element. The resistance level of the heating element may be used to indicate an average temperature of the heating surface. The heating element may be arranged to deliver a higher power density in a specified region of the heating element as compared to a power density delivered to other regions of the heating element (for example, as explained in reference to FIG. 4C). The specified higher density region of the heating element may be located at an outlet of a water supply to the heating surface. The specified higher density region of the heating element may be located at a water pre-heating area on the heating surface.

A component of the respiratory therapy system 100 or of the respiratory humidification system 101 can include a controller 118 that can control the operation of components of the respiratory therapy system 100 or of the respiratory humidification system 101, including but not limited to the flow generator 120, the metering arrangement 110, and/or the heating device 114.

The metering arrangement 110 may be configured to meter or allocate fluid to the humidification housing 115 and/or to the heating device 114 at metering rates that raise the moisture content of gases passing through the gases channel 102 such that the gases reach a predetermined, calculated, or estimated humidity level representing a level of gases humidification needed or desired by a patient using the respiratory humidification system 101 while taking care to reduce or eliminate the likelihood of undue moisture accumulation in the gases channel 102. To implement this, in one example, the controller 118 can control the metering rate of the metering arrangement 110 based on (a) a measured flow rate of gases passing through the gases channel 102, (b) a measured moisture value corresponding to the humidity of gases upstream of the humidification housing 115, (c) a measured pressure level corresponding to the pressure level in the gases channel 102, or (d) a combination thereof. The controller 118 can control the metering rate of the metering arrangement 110 based on a combination of one or more of measured inputs (a)-(c), such as based on (a) measure flow rate of gases passing through the gases channel 102 and (b) a measured moisture value corresponding to the humidity of gases upstream of the humidification housing 115, or (a) a measured flow rate of gases passing through the gases channel 102 and (c) a measured pressure level corresponding to the pressure level in the gases channel 102.

In some configurations, the metering rate of the metering arrangement 110 may be directly calculated by the controller 118. Illustratively, by way of non-limiting example, if the flow rate of gases passing through the flow channel 102 is determined to be 20 L/min, and the desired output humidity of gases exiting the respiratory humidification system 101 is determined to be 44 mg/L then, if one were to assume that the humidity of gases entering the system was zero (that is, if the gases were completely dry), 0.88 g/min of fluid (20 L/min*0.044 g/L) would need to be added to the gases in the gases channel 102. A correction factor may then be calculated corresponding to the (assumed, estimated, calculated or measured) humidity of the gases entering the respiratory humidification system 101. Accordingly, particularly if the fluid can be vaporized rapidly, the metering rate of the metering arrangement 110 may be set to 0.88 g/min, adjusted by the correction factor derived from the assumed, estimated, calculated, or measured humidity of gases upstream of the humidification housing 115 or of ambient gases present outside of the respiratory therapy system 100.

The desired output humidity (for example, relative humidity (RH)=100% or absolute humidity (AH)=44 mg/L) and/or desired output temperature (for example, 37° C. or 98.6° F.) of gases may be input by a user of the respiratory humidification device 101 through, for example, a user interface 105 located on a housing 103 of the respiratory therapy system 100 or using a remote control module. The user interface 105 can include, for example, one or more buttons, knobs, dials, keyboards, switches, levers, touch screens, speakers, displays, and/or other input or output modules so that a user might use to view data and/or input commands to control components of the respiratory therapy system 100 or of the respiratory humidification system 101.

The respiratory therapy system 100 or the respiratory humidification system 101 may include deterministic or open loop control. Various control systems will be described in greater detail in reference to FIGS. 2A-2E below. In general, deterministic control may allow for on-demand humidification achieved by controlling certain input variables, for example, by controlling water flow to the heating surface. In some configurations, control of the water flow rate to the heating surface may be based on a flow rate of the gases in the gases channel. Control of the water flow rate to the heating surface may be based on an evaporation rate of the water from the heating surface. Control of the water flow rate to the heating surface may be based on a temperature of the heating surface wherein the temperature of the heating surface is maintained at a constant temperature. Control of the water flow rate to the heating surface may be based on a temperature of the heating surface wherein the temperature of the heating surface is controlled. Control of the water flow rate to the heating surface may be based on an absolute or barometric pressure of the gases at or near the inlet location. Control of the water flow rate to the heating surface may be based on a dew point temperature of the gases at the inlet location. Control of the water flow rate to the heating surface may be based on an enthalpy provided by the heating surface. Control of the water flow rate to the heating surface may be based on a power level provided by the heating surface. Control of the water flow rate to the heating surface may be based on a temperature of the gases at the inlet location. The dew point temperature of the gases at the inlet location may be derived by processing information provided by a temperature sensor and a humidity sensor. Control of the water flow rate to the heating surface may be based on the dew point temperature of the gases at the inlet location. Control of the water flow rate to the heating surface may be based on a relative humidity level of the gases at the inlet location. Control of the water flow rate to the heating surface may be based on an effective heating area of the heating surface. Control of the water flow rate to the heating surface may be based on a pressure level of the gases in the gases channel. Control of the water flow rate to the heating surface may be based on a velocity of the gases flowing in the gases channel. Control of the water flow rate to the heating surface may be based on a temperature of the water flow. As shown and described in reference to FIG. 1E below, the respiratory therapy system 100 and/or the components thereof (including the respiratory humidification system 101) may include a number of sensors to measure these variables.

The illustrated configuration should not be taken to be limiting and many other configurations for the respiratory therapy system 100 and the components thereof (including the respiratory humidification system 101) are contemplated. Additional details for configurations of components of the respiratory therapy system 100 are described below.

The first and second fluid conduits 108, 112 may be configured to communicate fluids to various components of the respiratory humidification system 101. As illustrated in FIG. 1A, the first fluid conduit 108 may be configured to fluidly communicate fluid from the fluid reservoir 106 to the metering arrangement 110, and the second fluid conduit 112 may be configured to fluidly communicate fluid from the metering arrangement 110 to the humidification housing 115. In some configurations, the first and/or second fluid conduits 108, 112 are optional. For example, if the fluid reservoir 106 is in direct fluid communication with the metering arrangement 110, the first fluid conduit 108 need not be present. Likewise, if the metering arrangement 110 is in direct fluid communication with the humidification region 115, the second fluid conduit 112 need not be present.

Figure 1B:
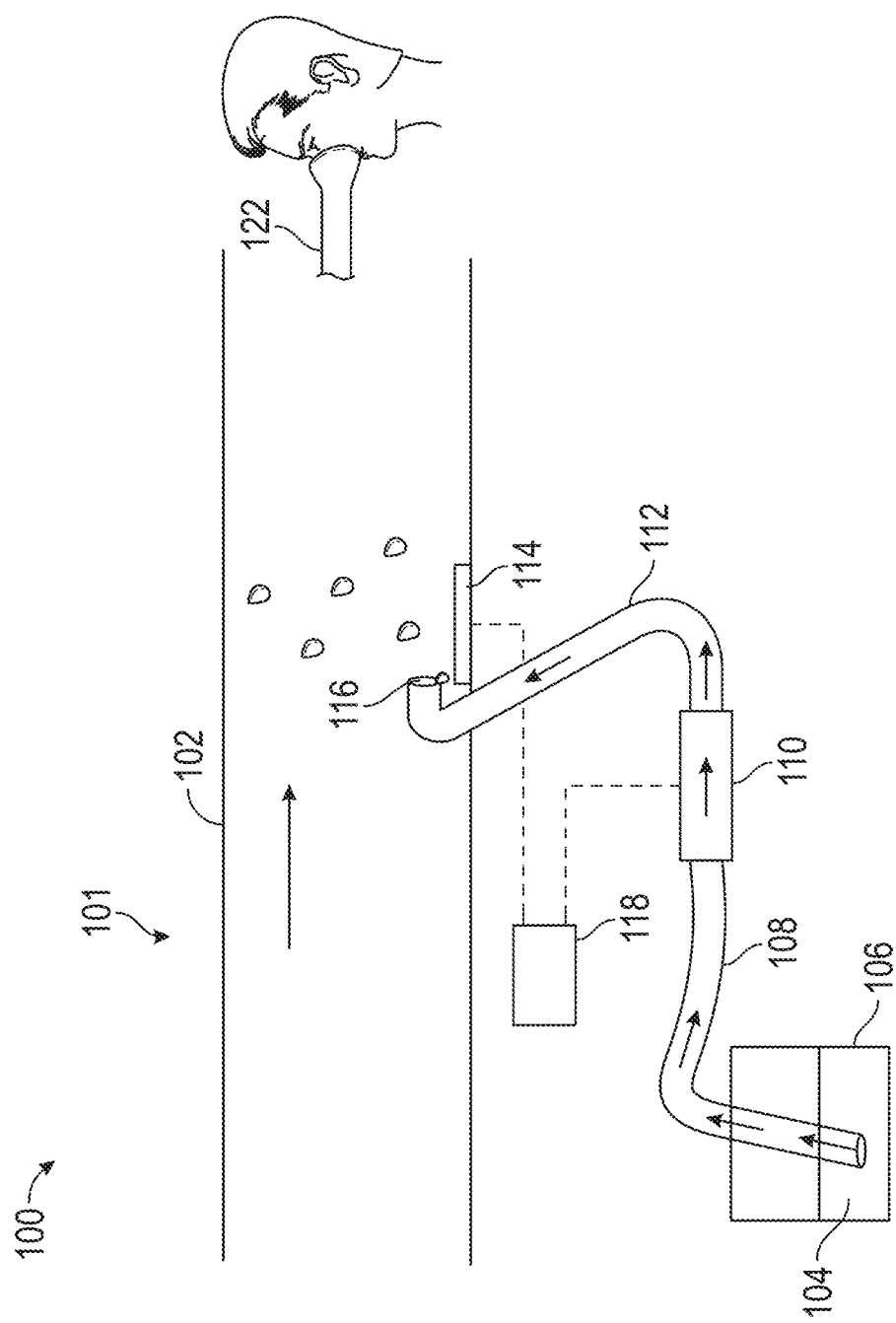
Figure 1C:
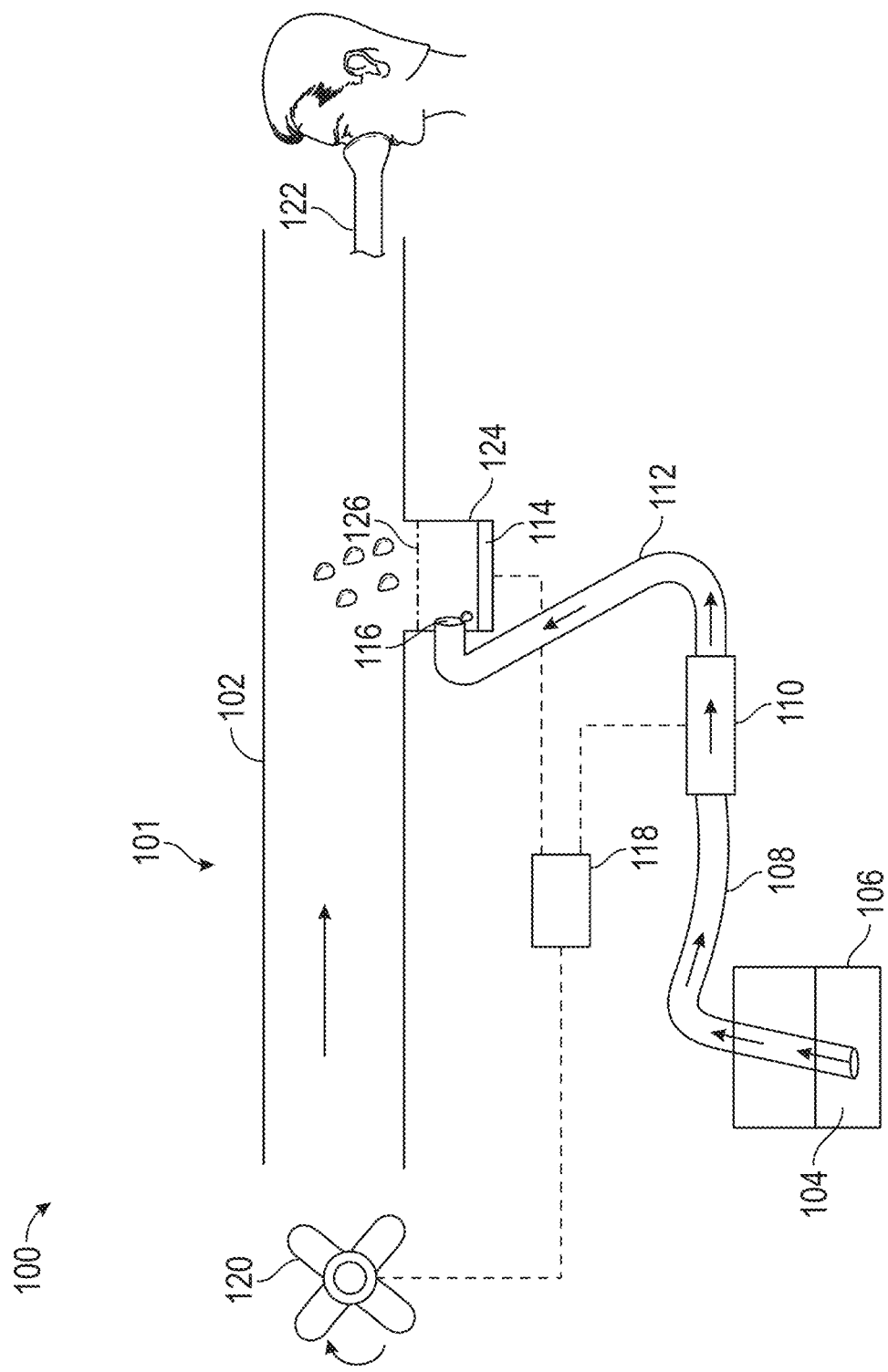
Figure 1D:
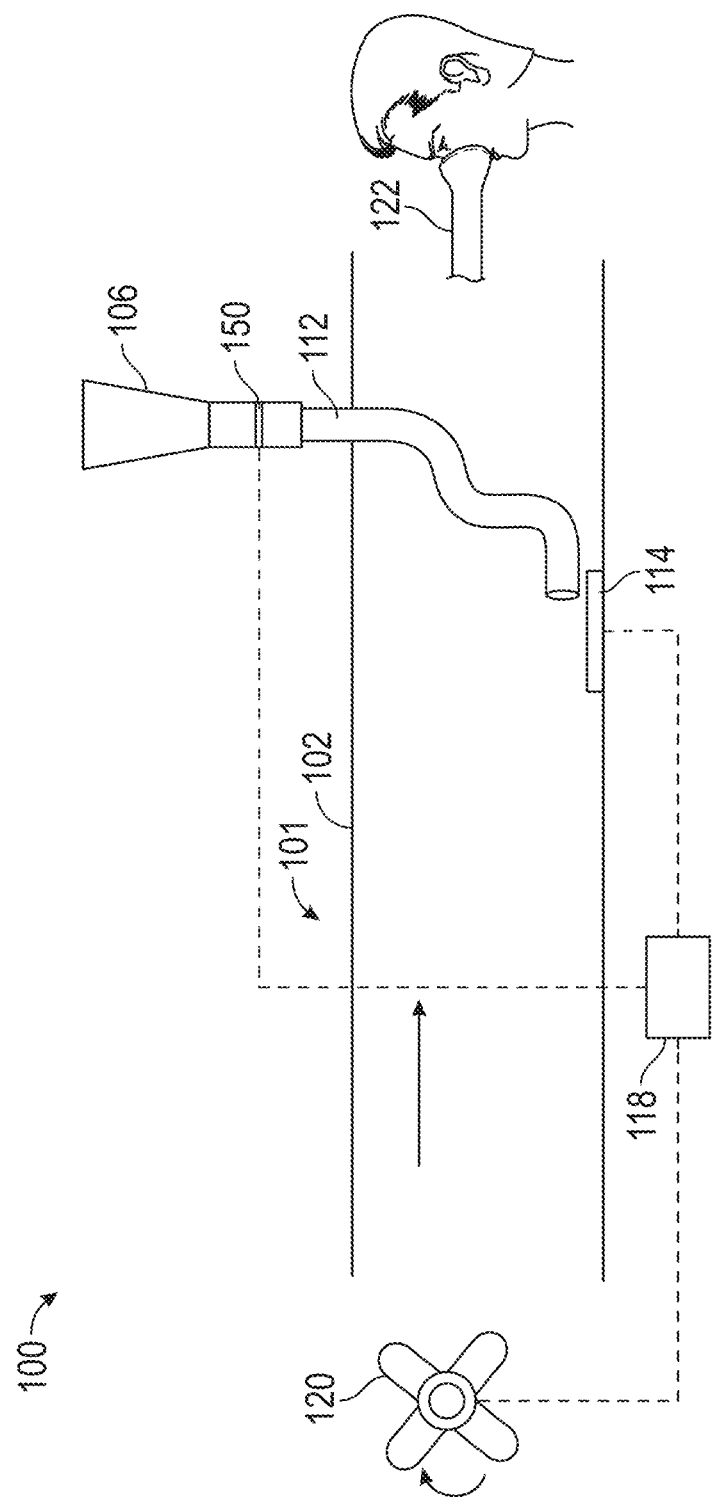
Figure 1E:
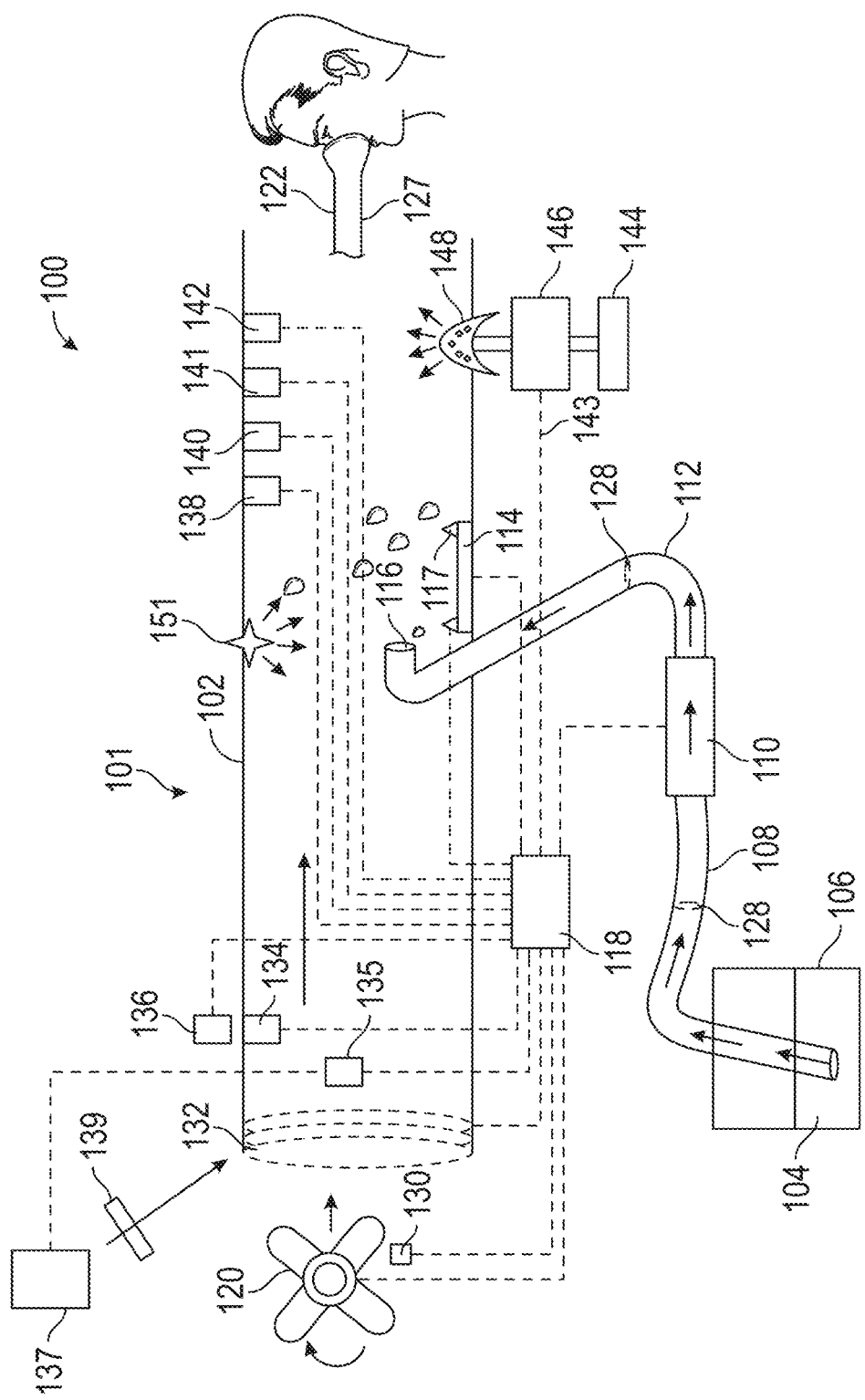

As illustrated in FIG. 1E, the first and/or second fluid conduits 108, 112 may additionally comprise one or more filters 128 configured to remove contaminants, impurities, or other undesired materials from the fluid passing from the fluid reservoir 106. The filters 128 can include any structure configured to do such, including permeable or semipermeable membranes positioned in the fluid flow paths of the first and/or second conduits 108, 112 and/or configured for use in microfiltration, ultrafiltration, or reverse osmosis. The presence of one or more filters 128 in the first and/or second conduits 108, 112 may help to assure a user of the respiratory humidification system 101 that the quality of fluid introduced into the humidification housing 115 is at an acceptable level. If one or more of the filters 128 has been used for too long a period of time, the filters 128 and/or the first and/or second conduits 108, 112 may be replaced. The age of the filters 128 may be indicated to a user through, for example, a chemical color change indicator located in or on the first and/or second conduits 108, 112 or the filters 128 may change in color over time due to prolonged exposure to gases and/or fluids. The filter 218 may serve as a preliminary distributor of the humidification liquid.

As described above, the metering arrangement 110 can serve to meter fluids from the fluid reservoir 106 to the humidification housing 115. The metering arrangement 110 can include, for example, a fluid displacement pump that may actively transfer fluid from the fluid reservoir 106 to the humidification housing 115 along, for example, the first and/or second conduits 108, 112. In certain embodiments, the metering arrangement 110 may run in reverse or act to withdraw fluid from the humidification housing 115. The fluid displacement pump can include, for example, a positive displacement pump, such as a piezoelectric diaphragm pump, a peristaltic pump, a micro-pump, or a progressive cavity pump.

As shown in FIG. 1B, the system can be embodied as an in-line humidifier. In this embodiment, the humidification system 101 can be an add on to a respiratory circuit for use with any flow generation system or it can be a stand-alone humidifier using ambient air and relying on normal patient respiration to generate a flow of gases.

As demonstrated in FIG. 1C, in some configurations, the heating device 114 may be positioned outside of the gas channel 102. For example, the heating device 114 may be present in a separate compartment 124. The compartment 124 may be physically linked to the gas channel 102 but may be fluidly isolated from the gas channel 102. The compartment 124 may be fluidly isolated from the gas channel 102 through the use of a semipermeable membrane 126 positioned between the compartment 124 and the gas channel 102. In some configurations, the semipermeable membrane 126 may not allow fluid to pass through but may allow vaporized fluids to pass through (and thereby allow vaporized fluids to join gases passing through the gas channel 102). Examples of suitable materials for use with the semipermeable membrane include perfluorinated polymers or polymers with fine pores and include materials such as those used in the tubing described in commonly-owned U.S. Pat. No. 6,769,431, filed May 8, 2001 and titled "Expiratory Limit for a Breathing Circuit," and U.S. patent application Ser. No. 13/517,925, filed Dec. 22, 2010 and titled "Components for Medical Circuits," both of which are incorporated by reference herein in their entirety. In use, fluid may be metered through the outlet 116 to the compartment 124, vaporized using the heating device 114 (which may additionally be positioned in the compartment 124), and forced through the semipermeable membrane 126 to join the downstream-moving gases passing through the gas channel 102. Fluidly isolating the outlet 116 from the gas channel 102 may, for example, reduce the likelihood of liquid water being present in the gas channel 102.

It should be understood that the metering arrangement 110 need not necessarily include a pump and may simply include a structure configured to allocate fluid to the humidification housing 115 in predetermined, desired, or regulated amounts. For example, and as demonstrated in FIG. 1D, the fluid reservoir 106 may be suspended vertically above the gases channel 102 and/or humidification housing 115. The fluid reservoir 106 may be in communication with an electromechanical valve 150 that may, in response to signals generated by the controller 118, partially or fully open or close to control the passage of fluid from the fluid reservoir 106 to the humidification housing 115 through the second fluid conduit 112.

In some configurations, the second fluid conduit 112 may not be present and the fluid reservoir 106 may cooperate with the electromechanical valve 150 to transfer fluids directly to the humidification region 115 (and/or to a location at or near the heating device 114). Fluid flow sensors such as, but not limited to, Micro-Electrical-Mechanical Systems or MEMS sensors, may be used to determine the fluid flow through the electromechanical valve 150 or second fluid conduit 112. Signals from the fluid flow sensor or values derived therefrom may be used to, for example, control the operation of the electromechanical valve 150 via closed-loop control. Although in FIG. 1D the fluid reservoir 106 is shown as being vertically above the gases channel 102, in some configurations, the fluid reservoir 106 may be at the same level as the gases channel 102 or lower than the gases channel 102. Other forces may act upon the fluid reservoir 106 to meter fluid in combination with the electromechanical valve 150. For example, the respiratory humidification system 101 may be configured such that fluids are propelled from the reservoir 106 using the force of gases passing through the respiratory therapy system 100 and/or the respiratory humidification system 101. In some configurations, the gases may act on the fluid in the fluid reservoir 106 directly. In some configurations, the fluid reservoir 106 may be pressurized by fluid filled pouches (filled by, for example, gases from the flow generator 120 or from a separate gases source) that force fluid from the fluid reservoir 106. The pressure exerted by the pouches may be controlled using a biasing force generated by, for example, a spring or other mechanical arrangement.

In some embodiments, the heating device 114 may be configured to transfer heat to fluids that are metered on to or near the heating device 114 to encourage fluid vaporization and entrainment into the gases flow passing through the gases channel 102. The particular form of the heating device 114 is not limited and many varieties of heating devices may be envisioned for use with the respiratory humidification system 101. In some configurations, the heating device 114 may include a heating plate or element that may resistively heat upon the application of electrical energy. The resistive heating plate may be constructed from an electrically conductive metallic material but may also be made from conductive plastics.

The controller 118 can include a microprocessor or some other architecture configured to direct the operation of controllable components of the systems 100, 101. In some configurations, one controller 118 may control the operation of every controllable component of the respiratory therapy system 100 and/or respiratory humidification system 101, including but not limited to the metering arrangement 110, the heating device 114, and/or the flow generator 120. The controller 118 may be physically present in, on, or near a component of the respiratory therapy system 100, including but not limited to the flow generator 120, the respiratory humidification system 101, the housing 103, and/or the gas channel 102. In some configurations, the controller 118 may be physically separate from the respiratory therapy system 100. For example, the controller 118 could be located on a remote computer, tablet, mobile phone, smartwatch, or another device, and the controller 118 may remotely direct the operation of the controllable components of the respiratory therapy system 100. In some configurations, multiple controllers may be used to control the controllable components of the respiratory therapy system 100 and/or respiratory humidification system 101. The multiple controllers may each be directed to exclusive control of one or more controllable components of one or both of the systems 100, 101. In some configurations, the control of one or more controllable components of one or both of the systems 100, 101 may be handled by multiple controllers. The multiple controllers may be configured to communicate with one another.

To control the metering rate of the metering arrangement 110 through the controller 118 in accordance with the functions described above or elsewhere in this specification (for example, by using measured flow values, moisture values, and/or pressure values; see, for example, the description of FIGS. 2A-2E below), the assumed, estimated, calculated or measured signals and values can be determined. In some configurations, the signals and/or values can be determined as described below.

A predetermined value may be selected to represent the flow rate of gases passing through the gases channel 102. By way of non-limiting example, the flow rate of gases passing through the gases channel 102 may be assumed to be 40 L/min.

A gases flow rate value, corresponding to the flow rate of gases passing through the gases channel 102, may be estimated or approximated through a variety of means. In some cases, the flow generator 120 includes a mechanical blower 121. The motor speed, motor torque, and/or motor current of a motor of the blower 121 may be determined using a motor sensing module 130 (for example, as illustrated in FIG. 1E) including, for example, one or more relevant transducers. One or more of the signals output by the motor sensing module 130, or values derived therefrom, may be inputs into a lookup table or equation, either of which in turn may return an estimated or approximated gases flow rate value based on, for example, an experimentally-determined set of inputs and outputs.

Flow signals representative of the flow rate of gases passing through the gases channel 102 may be generated by a gases flow sensor 134 (see FIG. 1E) positioned in the gases channel 102. A signal generated by the gases flow sensor 134 may be processed and converted to a gases flow rate value.

A predetermined value may be selected to represent the relative or absolute humidity of gases upstream of the humidification housing 115. Illustratively, by way of non-limiting example, the relative humidity of gases upstream of the humidification housing 115 may be assumed to be 50%, or the absolute humidity of gases upstream of the humidification housing 115 may be assumed to be 15 mg/L.

If the temperature and relative humidity of gases passing through the gases channel 102 can be sensed or otherwise estimated or determined, the dew point temperature of the gases may be derived using, for example, the Clausius-Clapeyron equation. The relative humidity value may be converted into an absolute humidity value if the temperature and pressure of the gases upstream of the humidification housing 115 can be sensed or otherwise estimated or determined.

A moisture signal representative of the relative or absolute humidity of the gases upstream of the humidification housing 115, or of ambient gases outside of the respiratory therapy system 100 may be generated by a humidity sensor 136 (for example, as illustrated in FIG. 1E) positioned upstream of the humidification housing 115 or outside of the respiratory therapy system 100. A signal generated by the humidity sensor 136 may be processed and converted to a moisture value.

Various sensor modules may also be positioned in the gases channel 102 downstream of the humidification housing 115. As demonstrated in FIG. 1E, the sensor modules may include, for example, a flow sensor 138, a humidity sensor 140 (for example, including absolute and/or relative humidity sensors), a temperature sensor 141, and/or a pressure sensor 142. One or more of these sensors may be used by the controller 118 to facilitate control of components of the respiratory therapy system 100 and/or respiratory humidification system 101, including control of the operation of the gases flow generator 120 (including, for example, a motor speed of a blower 121), of the heat output of the heating device 114, of the metering rate of the metering arrangement 110, and/or of some other component.

Also, as demonstrated in FIG. 1E, a gas concentration sensor 135 may be positioned in the gases channel 102. The gas concentration sensor 135 may be configured to sense the concentration of one or more gases in the gases stream. The gas concentration sensor 135 can include an ultrasonic sensor adapted to sense, for example, oxygen. The gas sensed may include, for example, oxygen, nitric oxide, carbon dioxide, and/or heliox introduced to the gases channel 102 from a gases reservoir 137 through a gases concentration adjustment valve 139. The gas concentration sensor 135 may use a gas concentration signal generated by the gas concentration sensor 135 to control the gas concentration adjustment valve 139 (for example, via closed-loop control) based on a predetermined desired gas concentration (for example, entered by a user through the user interface 105).

In some configurations, and as demonstrated in FIG. 1E, a fluid sensor 117 may be in communication with the humidification housing 115 and/or the heating device 114 as a safety measure to help avoid burning the patient with overheated gases. Illustratively, the fluid sensor 117 may be configured to generate a signal upon detection of the presence of fluid in the humidification housing 115 and/or in or on the heating device 114. The controller 118 may use the signal emitted by the fluid sensor 117 to control the operation of the metering arrangement 110 and/or the operation of the heating device 114. For example, the metering rate of the metering arrangement 110 and/or the heat output of the heating device 114 may be set to a function of the signal generated by the fluid sensor 117. The metering rate of the metering arrangement 110 may be increased if the signal does not indicate the presence of fluids in or near the humidification housing 115, or on a modular area of the heating device, since the heating devices is intended to be covered with a film of humidification fluid. Likewise, the heat output of the heating device 114 may be reduced or set to zero if the signal does not indicate the presence of fluids in or near the humidification housing 115, or on a modular area of the heating device, so as to avoid heating the gases to an unsafe temperature. The fluid sensor 117 may be thus used to aid in the control of the metering arrangement 110 and/or the heating device 114 if it is determined that fluids are not present in the humidification region 115 and/or on the heating surface of heating device 114 when they would otherwise be expected to be present in such locations (for example, if the metering arrangement 110 is attempting to meter fluids at a positive rate). In some configurations, the respiratory therapy system 100 or a component thereof (including the respiratory humidification system 101) may be configured to generate an alarm or convey a message to a user (for example, through the user interface 105) upon such a determination to let the user know that the situation should be corrected (for example, by refilling the fluid reservoir 106).

While, in some configurations, a humidification system may include separate sensors to measure the surface temperature and other sensors to measure whether the surface is wetted (e.g. fluid sensors 117, preferably at/near the edge of the heating element 114, which could be temperature sensors but also any other water-detectors such as a resistive or capacitive sensor), in other configurations, it is possible to use a control algorithm to set the surface temperature so as to achieve a desired evaporative (wetted) area. The algorithm may be based on the system measurements (gas flow rate, water flow rate, etc., as described below) and a model (e.g. Dalton's law of evaporation). The fluid sensors 117 may therefore serve as a safety mechanism to prevent overfill and as a means of correcting/adjusting the algorithm (by providing a calibration point where the surface is known to be saturated). The system may therefore be configured to provide a modular arrangement, such that a single zone, or selected zones, could be wet, and that single zone, or those selected zones, could be powered. Again, this modular system could be controlled using a control algorithm based on system measurements. Separate sensors may be used to measure the surface temperature and other sensors to measure whether the surface is wetted. The fluid sensors 117 may be used in closed feedback control to control the metering of the water to the selected zone or zones, or, alternatively, the control algorithm may use a model to control the metering of the water to the selected zone or zones, such that the fluid sensors 117 may serve as a safety mechanism to prevent overfill and as a means of correcting/adjusting the algorithm (by providing a calibration point where the surface is known to be saturated).

In some configurations, the fluid sensor 117 may include a capacitive fluid sensor. If a heating surface of heating device 114 is present, the capacitive fluid sensor may, for example, include a pair of conductive sense electrodes positioned on opposing sides of the heating surface. If the conductive sense electrodes are connected in a circuit and a voltage is applied, the capacitance of the circuit will vary depending on the presence or absence of water. The capacitance of the circuit may be measured using, for example, a standard AC measuring circuit. Many other sensing systems, including ultrasonic or optical level sensing systems, may also be used to determine the presence of fluid.

Various sensor modules may be utilized by the controller 118 to control various components of the respiratory therapy system 100 and/or the respiratory humidification system 101. The sensor modules can include one or more sensors for detecting various characteristics of gases in the gases channel 102 or elsewhere in, around, or near the respiratory therapy system 100 (including in or near the gases inlet 123, the gases outlet 127, the patient interface 122, or at, upstream and/or downstream of the humidification housing 115), including pressure, gases flow rate, temperature, absolute humidity, relative humidity, enthalpy, gas composition, oxygen concentration, carbon dioxide concentration, ambient temperature, and/or ambient humidity. One or more of these sensors and/or sensor modules may be used, for example, to facilitate the control of the flow generator 120 (including control of the pressure and/or flow rate of gases propelled downstream by the flow generator 120), control of the heat output of the heating device 114 (including control of the temperature of the heating device), and/or control of the metering rate of the metering arrangement 110 (including control of power and/or current applied to the metering arrangement 110).

In some configurations, respiratory activity of a patient using the respiratory therapy system 100 and/or respiratory humidification system 101 may be determined, estimated or calculated using one or more of the sensors or sensing modules described above or elsewhere in this disclosure. The controller 118 may control various components of the respiratory therapy system 100 and/or the respiratory humidification system 101 such that the components operate based on a determined respiratory activity or respiratory state. Illustratively, by way of non-limiting example, the heating device 114 may be configured to only be energized or to only vaporize substantial amounts of fluid when the patient is determined to be inspiring. The metering arrangement 110 may be configured to only meter fluids when the patient is determined to be inspiring. The flow generator 120 may be configured to only generate a flow or to increase the flow generated when the patient is determined to be inspiring.

Additionally, the components may be controlled such that they act in a synchronized manner with the determined instantaneous respiratory activity or respiratory state of the patient, rather than being limited to binary states of operation. For example, the heating device 114 may be configured to, at the start of inspiration, have a relatively low heat output, increase in heat output towards a maximum at the peak of inspiration, and then decrease in heat output towards the end of inspiration. The metering arrangement 110 may meter a relatively small quantity of fluid at the start of inspiration, progressively increase the metering rate towards a maximum at the peak of inspiration, and then decrease in rate towards the end of inspiration. The flow generator 120 may be configured to generate or propel gases at a relatively low flow rate at the start of inspiration, progressively increase the flow rate of gases towards a maximum at the peak of inspiration, and then decrease in flow rate towards the end of inspiration. Other components of one or both of the systems 100, 101 may be controlled similarly.

In some configurations, the flow generator 120 may, for example, include a source or container of compressed gas (for example, air, oxygen, etc.). If a container is used, the container may include a valve that can be adjusted to control the flow of gases leaving the container. In some configurations, the flow generator 120 may use such a source of compressed gases and/or another gases source in lieu of the blower 121. In some configurations, the flow generator 120 may use such a source of compressed gases and/or another gases source together with the blower 121. The blower 121 can include a motorized blower or a bellows arrangement or some other structure adapted to generate a gases flow. In some configurations, the flow generator 120 may draw in atmospheric gases through the gases inlet 123. In some configurations, the flow generator 120 may be adapted to both draw in atmospheric gases through the gases inlet 123 and accept other gases (for example, oxygen, nitric oxide, carbon dioxide, etc.) through the same gas inlet 123 or through a different gas inlet (not shown). In some configurations and as demonstrated in FIG. 1B, the flow generator 120 may not be present and the respiratory therapy system 100 may be configured such that only unpressurized ambient air is humidified and channeled to the outlet/patient interface 122.

In some configurations and as demonstrated in FIG. 1E, the respiratory therapy system 100 and/or respiratory humidification system 101 may comprise an electromagnetic radiation emitter 151 (positioned in, for example, the gas channel 102). The emitter 151 may comprise an ultraviolet light source (e.g., UV LED), a microwave emitter, or some other radiation emitter configured to sterilize the gas flow path. Means for sterilizing the passage through which gases pass through the respiratory therapy system 100 and/or respiratory humidification system 101 can reduce concerns of patient infection through the introduction of undesired pathogens.

In some configurations and as demonstrated in FIG. 1E, the respiratory therapy system 100 and/or the respiratory humidification system 101 can include a gases heating region 132. The gases heating region 132 can pre-heat gases passing through the gases channel 102 before the gases reach the humidification housing 115. If the gases are pre-heated before they are humidified, the efficiency of the humidification may be improved. The gases heating region 132 can include, for example, one or more resistive heating wires present in, on, around, or near the inner and/or outer walls of the gases channel 102. The gases heating region 132 may be controlled by and in electrical communication with the controller 118, which may control the heat output of the gas heating region 132 using sensor signals in a manner, for example, similar to the control of the heat output of the heating device 114 as described elsewhere in this disclosure. The controller 118 can control the temperature and/or the heat output of the gases heating region 132 such that gases arrive at the gases outlet 127, the patient interface 122, or at the patient at a temperature of between approximately 31° C. to approximately 43° C. In some cases, if the gases heating region 132 is distal from the gases outlet 127 or the patient interface 122, the gases heating region 132 may heat the gases to a temperature higher than between approximately 37° C. to approximately 43° C. such that the gases arrive at the gases outlet 127, the patient interface 122, or the patient at the desired temperature (due to temperature loss as the gases pass along, for example, the gases channel 102). To find the correct temperature, the temperature loss of gases passing through the respiratory therapy system 100 may be theoretically or experimentally modeled. Gases in the range of approximately 25° C. to approximately 43° C., or approximately 31° C. to approximately 43° C., or approximately 31° C. to approximately 41° C., or approximately 31° C. to approximately 37° C. are generally considered to be comfortable for patient use.

The gases heating region 132 may include a gases pre-heater which may include a gases heating element. The gases heating element may be a printed circuit board. The printed circuit board may have resistive elements. The gases heating element may be an etched foil film (see for example, FIGS. 4D and 4E). The gases heating element may be a heating coil. The gases heating element may be a PTC ceramic. The respiratory humidification system 100 may have a temperature sensor. The temperature sensor may be positioned in the gases channel downstream of the gases pre-heater. A temperature sensor may be positioned in the gases channel upstream of the gases pre-heater, either instead of or in addition to the temperature sensor positioned downstream of the gases pre-heater. A characterization of the gases heating element may be used to determine a temperature of the gases. Control of a power level delivered to the gases heating element may be based on information provided by a temperature sensor positioned in the gases channel downstream of the gases pre-heater. Control of the power level delivered to the gases heating element may be based on information provided by a gases flow sensor and by a temperature sensor positioned in the gases channel upstream of the gases pre-heater. A desired downstream temperature of the gases may be determined based on an evaporation rate of the water from the heating surface. The desired downstream temperature of the gases may be set to ensure that substantially all sensible heat is supplied by the gases pre-heater. The desired downstream temperature of the gases may be set to obtain a desired relative humidity level of the gases at the outlet location. The desired downstream temperature of the gases may be set to be between 0° C. and approximately 5° C. above a desired temperature of the gases at the outlet location. The desired downstream temperature of the gases may be set to be a desired dew point temperature at the outlet location. The desired downstream temperature may be set to approximately 25° C. to approximately 43° C., or approximately 31° C. to approximately 43° C., or approximately 31° C. to approximately 41° C., or approximately 31° C. to approximately 37° C., or approximately 37° C. The heating surface may include a heating element configured to provide heat to the heating surface. The heating element may include a plurality of resistive tracks. The heating element may be a printed circuit board. The printed circuit board may have resistive elements. The gases heating element may be an etched foil film (see for example, FIGS. 4D and 4E).

FIGS. 2A-2E are functional block diagrams illustrating various control features of the present disclosure. In some configurations, the control features described herein allow for deterministic, or open-loop control of the humidification system. That is, it is possible to calculate a required flow rate of water to achieve a certain humidity and dose that amount of water onto a heater. The heater may evaporate the water dosed thereon to obtain the desired dew point temperature. Deterministic control, may preclude the need (that is present in many conventional humidification system) to measure the outgoing humidity or some other indirect variable, and then feed this back through a closed-loop controller to achieve a specific dew point temperature. In some configurations, the control features described herein allow for a humidification system that evaporates only the right of amount of water, or other humidification liquid, at the correct time to accurately produce the correct humidity. The control features described herein may be combined or otherwise modified to be included into any of the respiratory humidification systems described herein. In some configurations, deterministic control of the humidity by controlling the water flow to the heater surface together can allow for heating the heater surface at a relatively low temperature heater.

For deterministic control, the water flow rate to be dosed onto the surface to produce a desired dew point temperature may be calculated from the equations below.

Symbols used in the following equations can be understood with reference to Table 1, which also provides the associated units for each variable. Additionally, a symbol appended with subscript(s) a, b indicates component a at the location b. The subscripts a, i, s, and o refer to ambient, inlet, surface (heater-plate), and outlet respectively; the subscripts w, wv, and air refer to the water, water vapor, and dry air respectively. Thus, for example, $Q_{air,i}$ indicates the mass flow rate of air at the inlet. It should be noted that equations 1-6 are written at steady state (or, equivalently, under the assumption that all the variables respond instantaneously).

TABLE 1

NOMENCLATURE

| Symbol | Meaning | Symbol | Meaning | Symbol | Meaning |
| --- | --- | --- | --- | --- | --- |
| T | Temperature (° C.) | p | Pressure (Pa) | $T_d$ | Dew-point temperature (° C.) |
| Q | Mass flow rate (kg s$^{-1}$) | $h_s$ | Specific humidity (kg kg$^{-1}$) | M | Molecular weight (g mol$^{-1}$) |
| P | Power (W) | $c_p$ | Specific heat capacity (J kg$^{-1}$ K$^{-1}$) | φ | Relative humidity (dimensionless) |
| l | Latent heat of vaporization (J kg$^{-1}$) | ρ | Density (kg m$^{-3}$) | m | Mass (kg) |

For deterministic control, the water flow rate to be dosed onto the surface to produce a desired dew point may be calculated from the following equations:

$$h_s(T_d, p) = \frac{M_{wv}}{M_{air}} \frac{p_{sat}(T_d)}{p - p_{sat}(T_d)} \qquad \text{Eq. 1}$$

$$Q_{air,i} = Q_i \frac{1}{1 + h_s(T_{d,i}, p)} \qquad \text{Eq. 2}$$

$$Q_w = Q_{air,i}[h_s(T_{d,o}, p) - h_s(T_{d,i} p)] \qquad \text{Eq. 3}$$

Where $h_s$ is the specific humidity. The evaporation rate of water from the surface is modelled by the equation:

$$Q_w = kAf(v)[p_{sat}(T_s) - \phi p_{sat}(T_{d,i})] \qquad \text{Eq. 4}$$

Where A is the area of the surface, k is a constant to be determined for any particular surface, and $f(v)$ is an empirically determined function of gas velocity. The powers required for evaporation, $P_l$, and for heating the water, $P_w$, are given by:

$$P_l = l(T_s)Q_w \qquad \text{Eq. 5}$$

$$P_w = c_{p,w} Q_w (T_s - T_a) \qquad \text{Eq. 6}$$

The powers required to air, $P_{air}$, and the water vapor, $P_{wv}$, are given by:

$$P_{air} = c_{p,air} Q_{air,i}(T_o - T_i) \qquad \text{Eq. 7}$$

$$P_{wv} = c_{p,wv}[Q_w(T_o - T_s) + (Q_{in} - Q_{air,i})(T_o - T_i)] \qquad \text{Eq. 8}$$

Equations 1-3 represent the general idea of deterministic or open loop control of the system: the required amount of water to achieve a certain dew-point temperature. In the representation given, provided measurements of $Q_{air,i}$, $Q_w$, $T_{d,i}$, and p, the dew point temperature at the output, $T_{d,o}$, can be fully determined.

It is possible to make substitutions or rearrangements so that different inputs or outputs are used (e.g., absolute or relative humidity at the outlet, or volumetric flow at the inlet or a different location, etc.). It is possible to avoid making measurements of some of the input variables. $T_{d,i}$ and p could be completely unmeasured if appropriate assumptions could be made (e.g., a known altitude to compute p) or if the error introduced were acceptable (e.g., if $T_{d,i} \ll T_{d,o}$, its effect is small. It may not be possible to proceed without measurements of $Q_{air,i}$ or $Q_w$ since they are dominant factors. It is possible that some of the measurements are not made directly. For example, it is not necessary to measure $T_{d,i}$ directly, instead a sensor measurement of $T_i$ and $\phi_i$ (RH at inlet), can be used to compute $T_{d,i}$. The same can be said of the other variables.

Equations 1-6 assume that the pressure is constant throughout the system, although it is possible to revise the equations to avoid this assumption. Although the pressure can vary significantly through the entire system (e.g., the pressure drop across the cannula), the pressure in the vicinity of the evaporation surface and sensors is usually very close to constant, rendering such corrections unnecessary, in some configurations.

Equation 4 can be used to compute the area and temperature requirements for the evaporative surface and to model the system for control response. It is based on Dalton's law of evaporation, and unlike the previous equations it is semi-empirical. Therefore, other equations could be used that are not completely equivalent. Specifically equation 4 can be used to compute $T_s$ for a given A, or vice versa, both for design and control of the system, or to compute an independent check on $Q_w$. In general, equation 4 implies that the temperature of the incoming gas does not significantly impact the evaporation rate. However, there are two mechanisms by which it does, which can be important in some situations. First, the incoming temperature changes the relative humidity, $\phi$. This may be significant if $T_{d,o}$ is close to $T_s$. The second, and more important mechanism, is in the exchange of heat. If $T_i < T_{d,o}$, the water vapor must heat the air, and if there is not enough sensible heat in the water vapor to increase the gas temperature above $T_{d,o}$, some of it must condense to release latent heat. This can be a major complication when considering the net evaporation rate; although the surface can easily drive the evaporation, the cool air rapidly condenses the vapor. This may be avoided by increasing the surface temperature. This problem is further exacerbated by the nature of the evaporation. The water cannot be immediately evaporated into the entire gas, as a boundary layer exists near surface, so the water must evaporate into this and then diffuse across gas (in laminar flow) or be mixed (in turbulent flow). The vapor in the boundary layer can be saturated at the surface temperature, inhibiting further evaporation, so one of the main limiting factors is not the evaporation rate at the surface, but the rate at which the vapor is diffused or advected from the boundary layer. Thus the heat exchange between the vapor and air occurs at a boundary and the vapor must be hotter to prevent condensation (since the bulk of the latent heat is not accessible). These effects interfere both with the physical ability of the system to evaporate the water and the validity of the evaporative model.

Equations 5 and 6 are used to compute the power requirements and to model the system for control response. These equations make the assumption of 100% efficiency, which cannot be exactly true, but testing has indicated that the systems disclosed herein are very efficient. In a system where this is not true, appropriate corrections would have to be made, at the expense of accuracy and simplicity. Equations 5 and 6 can be used to compute an independent check on the power inputs (e.g., to limit enthalpy). They could also be used for control, for example, for open loop control or as a corrective feedback.

Although these equations have been used directly with acceptable results, implementing a robust and stable system may require further consideration as equations 1-6 are only accurate at steady state. For example, considering the water flow rate: a finite volume of water must reside on the evaporative surface, therefore, the evaporation rate of water does not immediately equal the flow rate of water, since this hidden "buffer variable" can cause a temporary difference.

Considering the finite water film thickness as an instructive example, if the mass of water on the surface is $m_w = A\rho_w t_w$, where $t_w$ is the water thickness (assumed constant), then to a first approximation (assuming that the heater-plate only supplies power for evaporation):

$$\rho_w t_w \frac{dA}{dt} = Q_w - kAf(v)[p_{sat}(T_s) - \phi p_{sat}(T_{d,i})] \quad \text{Eq. 9}$$

$$\frac{1}{c_{p,s} m_s} \frac{dT_s}{dt} = P_s - \frac{\ell}{\rho_w} kAf(v)[p_{sat}(T_s) - \phi p_{sat}(T_{d,i})] \quad \text{Eq. 10}$$

Equation 9 is obtained by considering the difference in water arriving at the surface as compared with that which is evaporating, and equation 10 is obtained, similarly, by considering the power delivered to the surface less that consumed by evaporation. Thus, the surface temperature and evaporative area are coupled in a time-varying and non-linear fashion, and a simplistic controller that relies only on the principles of equations 1-3 directly will produce the desired humidity only if and when the above system stabilizes. This highlights the important possibility of instability, even though they are only first order systems when considered individually, when combined, they could oscillate or be unstable.

Given, that for water, $\rho_w = 1000$ kg m$^{-3}$ and l=2.26 MJ kg$^{-1}$, if it is assumed (based on reasonable figures obtained by testing a prototype system) k=1 µL min$^{-1}$ cm$^{-2}$ kPa$^{-1}$, $t_w$=10 µm, $Q_w$=0.9 mL min$^{-1}$, $T_{d,i}$=15° C., $\phi$=75%, $f(v)$=1, $m_s$=0.025, $c_{p,s}$=400 J kg$^{-1}$ K$^{-1}$, and $P_s$=34 W operating at the point A=30 cm$^{-2}$ and $T_s$=70° C., then it is possible to linearize $p_{sat}(T_s)$ to $1.353T_s - 63.28$, from which the system can be represented as:

$$\frac{dA}{dt} = f(A, T_s) = 90 - A[0.1353T_s - 6.456] \quad \text{Eq. 11}$$

$$\frac{dT_s}{dt} = g(A, T_s) = 340 - A[0.5097T_s - 24.32] \quad \text{Eq. 12}$$

The Jacobian of the system is then:

$$J = \begin{bmatrix} f_A(A, T_s) & f_{T_s}(A, T_s) \\ g_A(A, T_s) & g_{T_s}(A, T_s) \end{bmatrix} = \begin{bmatrix} 6.456 - 0.1353T_s & -0.1353A \\ 24.32 - 0.5097T_s & -0.5097A \end{bmatrix} \quad \text{Eq. 13}$$

Or, at the operating point:

$$J_0 = \begin{bmatrix} -3.015 & -4.059 \\ -11.36 & -15.29 \end{bmatrix} \quad \text{Eq. 14}$$

The eigenvalues of $J_0$ are −18.3 and 0.0006, indicating that the system is unstable. The reason for this instability is that the system is driven at constant power—any mismatch will result in an excess or deficit of water, completely saturating or drying the surface respectively. By introducing a proportional feedback on the power term, the expression for the surface temperature becomes:

$$\frac{dT_s}{dt} = g(A, T_s) = 340 - \alpha(T_s - T_0) - A[0.5097T_s - 24.32] \quad \text{Eq. 15}$$

Then:

$$J = \begin{bmatrix} -3.015 & -4.059 \\ -11.36 & -\alpha - 15.29 \end{bmatrix} \quad \text{Eq. 16}$$

The characteristic polynomial is then $\lambda^2 + \Delta(a+18.31) + 3.015(a+15.29) - 46.11 = 0$, leading to the eigenvalues:

$$\lambda = \frac{-(\alpha+18.31) \pm \sqrt{\alpha^2 + 24.56\alpha + 335.3}}{2} \quad \text{Eq. 17}$$

From which it can be shown that for $\lambda < 0$ (stability), a>3 So even a small amount of feedback will stabilize the system, at least at this operating point.

Since the area is difficult to measure directly it is worth examining whether this is an observable state. Since the system is non-linear this is difficult to assess, but the equation for $T_s$ can be re-expressed as:

$$\frac{1}{c_{p,s}m_s}\frac{dT_s}{dt} = P_s - \frac{\ell}{\rho_w}\left(Q_w - \rho_w t_w \frac{dA}{dt}\right) \quad \text{Eq. 18}$$

Then rearrange to obtain:

$$\rho_w t_w \frac{dA}{dt} = Q_w + \frac{\rho_w}{\ell}\left[\frac{1}{c_{p,s}m_s}\frac{dT_s}{dt} - P_s\right] \quad \text{Eq. 19}$$

This, informally, indicates that the area is an observable state, with the other measurements all being known, instead of attempting to sense the area at some limit, the equation can be integrated over time to compute A continuously. Of course, it may still be desirable to design the system with the ability to sense when the surface is saturated, but such a model allows us to control the area smoothly, rather than bouncing off a hard limit.

A number of factors limit the control response time. The first fundamental limit is the dynamics of the evaporation surface during a transient. This is important largely for enthalpic considerations, and also when implementing breath-by-breath humidity control.

If the surface temperature is held constant, the evaporative area may be changed to control humidity. It can grow actively (by pumping water) but only shrink passively (by evaporation), thus limiting the downwards response to the time it takes to evaporate the "reservoir" of water. For example, if the air flow rate is dropped from 20 L min$^{-1}$ to 10 L min$^{-1}$, the initial evaporation rate will be 0.7 mL min$^{-1}$ for nominal conditions (37° C. dew-point temperature, etc.). If the area is initially 20 cm$^2$, and drops to 10 cm$^2$ (to maintain the dew-point temperature), and water film is 10 μm thick, 0.1 mL of extra water must be evaporated to shrink the area. Even if the pump switches off, it will take a minimum of 8.6 s to shrink (0.1 mL at 0.7 mL min$^{-1}$) minimum because as the area shrinks the evaporation rate drops off too, and if the pump switches on during that time it will slow the response further.

If the evaporative area is held constant, the surface temperature must change, and the limitation is again passive cooling. A 40 cm$^2$ plate with a 10 μm film holds 0.4 g of water; the latent power required for evaporation at 10 L min$^{-1}$ could be about 13 W, and 33.5 J is required lower water temperature by 20° C., corresponding to 2.6 s, assuming, similar to the former scenario, that the heater-plate switches off during this time and ignoring the fact that the evaporation rate will decrease as the surface cools.

10 μm can be a difficult water thickness to achieve, even with the micro-channels; for a wicking paper or fabric a more reasonable figure would be in the range of 0.1 mm or more, resulting in proportionately longer response times.

In some configurations, designing a breath-by-breath type humidifier requires a thin film of water; otherwise the surface temperature must be traded off against response time (a higher surface temperature to yield a small evaporation area). In the extreme, such a trade-off results in a very hot surface (>100° C.) which boils the water off and introduces issues of patient safety and materials compatibility.

Another factor that influences the response time is the thermal mass and resistance of the heater-plate. The thermal mass of the heater-plate contributes in the same way as the water, requiring time to cool passively by evaporation. An increased thermal resistance means a higher heater element temperature, which exacerbates the effect of thermal mass (by requiring larger temperature changes).

Equations 1-3 compute the water flow rate assuming all of the water evaporates. In some configurations, the goal of the control system is to ensure that it all does evaporate, to improve the transient response, and to control other aspects of the system. In some configurations, this may require as many independent inputs as there are independent outputs, otherwise the system will not be controllable. In the most basic scenario, in which it is only desired to control the humidity at the outlet, in which case one relevant control input, such as water flow rate, would suffice. However, if it is also desired to control the temperature at the outlet, another control input is required—for example, this could be the power delivered to the heater-plate. However, if it is desired to keep the heater-plate temperature within certain bounds, this would require another control input. The additional input could be to add a secondary heater to pre-heat the incoming air.

In some configurations, the concept of pre-heating the air may be important. Although a goal of the system is to determine the humidity at the outlet, being able to determine the temperature is also desired to prevent condensation. As explained above, the power delivered to the heater-plate would allow us to do this, but using heat from the evaporation surface convolves the two problems (evaporating water and heating air). Pre-heating the air separates these two problems and leads to several advantages, including:

Easier control: since the latent heat and sensible heat are added independently, they can be controlled almost independently. A combined control system would be more complex and less robust.

Improved evaporation: as explained above with reference to the evaporation equation, evaporating water into a warmed gas (i.e., $T_i > T_{d,o}$) is easier to do and model than evaporating into a cool gas (i.e., $T_i < T_{d,o}$).

Lower surface temperatures: following on from the improved evaporation, a warmed gas allows lower surface temperatures, and the surface temperature/area can be controlled independently.

Power: with the air being pre-heated, the burden on the heater-plate will be reduced, which yields the knock-on effects of requiring less temperature to drive the heating and better efficiency since the temperature is lower.

Enthalpy/safety: the bulk of the enthalpy in the system is supplied as latent heat in the water vapor, with the heat being added separately it is easier to ensure that the enthalpy is kept within limits while still being able to ensure that the gas at the exit is not saturated (to prevent condensation). In a system without preheating, the only way to limit the enthalpy is to limit the total power, without any direct control over whether this reduces the sensible rather than latent heat (and thus resulting in condensation).

In a similar vein, the system may also comprise pre-heating the water flow. This could be done by either heating the water source, heating the water feed line, or having a special zone on the heater-plate (e.g., the water wicks over the water pre-heater before reaching the evaporative region, or the initial region has a higher power density).

In some configurations, pre-heating the gas allows the latent heat and sensible heat to be provided to the system separately. The sensible heat may be provided by the pre-heater, while the latent heat may be provided by the water vapor. The result is that the heater plate may be kept at a lower temperature, which has advantages, such as patient safety. More specifically, safety is enhanced by lower temperatures as overshoots in delivered enthalpy are reduced, for example, a surface at 37° C. will not generate vapor at a dew point temperature of greater than 37° C., and hence no harm will ever come to the patient by way of burns.

One ancillary result of separating out the latent and sensible heats is that it becomes desirable to keep the heated portion of the evaporative surface saturated—if an unheated portion of the heating surface is exposed it will contribute to heating the air, which again convolutes the control task. For that reason it may be desirable to include a method of sensing when the water has reached the end of the surface, either by a physical means (temperature drop, shorting a conductor, capacitance), or the models formerly presented. This is also useful as a safety mechanism to prevent the system from flooding.

Figure 2A:
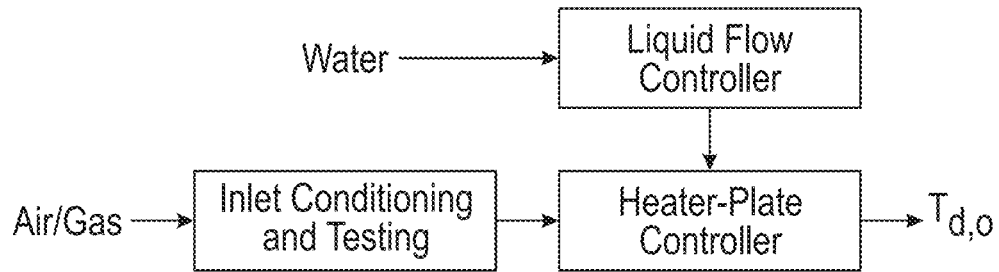
FIG. 2A is a functional block diagram of an overall control system in accordance with an embodiment of the present disclosure.

FIG. 2A illustrates an overall control topology of the respiratory humidification system 101 which illustrates in simplistic form a basic control principle in which a known amount of air plus a known amount of water results in a known humidity. By controlling the water and temperature it is possible to effectively control the evaporative rate of the water from the heating surface into the gas. In some configurations, it is not necessary to measure the evaporation flow rate as it is merely a function of other input variables. For example, it is possible to set the flow rate of water based on the desired evaporation rate. In some configurations, it is possible to calculate the evaporation that is actually occurring based on the surface temperature and power as a check. In the illustrated control topology, water is input into a liquid flow conditioner and routed to a heater-plate controller. Air and/or gas are received at an inlet for conditioning and testing before being routed to a heater-plate controller. The heater plate-controller computes the dew point temperature $T_{d,o}$, from the known (for example, determined either directly or indirectly through sensors) parameters of the incoming water and air and/or gas.

The inlet conditioning and testing represented in FIG. 2A can include an inlet sub-system at or near the gases supply location including one or more inlet sensors configured to measure inlet gases ambient humidity, inlet gases flow, inlet gases temperature, and a pressure level of the gases channel. An inlet gases heater may also be provided at or near the gases supply location to pre-heat the gases to a desired (predetermined) temperature as they enter and pass through the gases channel such that the gases arrive at the humidification location at a desired temperature. By separately pre-heating the gases, the energy delivered to the heating element in the humidification region can be used to vaporize the humidification fluid, thereby separating the functions of heating the gases (by supplying sensible heat from the gases pre-heater) and humidifying the gases (by providing latent heat from the heating element) in the gases channel. Advantageously, such a separation of functions permits the heating element to be operated at lower power levels corresponding to lower temperature levels which results in safer and more efficient operation of the respiratory humidification system. Moreover, the temperature of the heated gases can be altered quickly, such that the system becomes more responsive to changes than a system which heats an entire fluid reservoir, or a significant volume in excess to that required.

The liquid flow controller represented in FIG. 2A can include a humidification fluid flow control sub-system that monitors and controls the rate at which fluid is metered to the humidification region and, more specifically, to the heating element. A fluid flow sensor measures the flow of the humidification fluid and provides the measurement to a fluid flow controller. The controller compares the measured fluid flow rate with the desired fluid flow rate (which may be predefined, estimated, or deterministically derived), and adjusts the power level to the metering arrangement accordingly. In some embodiments, the humidification fluid is pre-heated before being delivered to the heating element for vaporization to reduce the amount of latent heat required by the heating element to vaporize the humidification fluid. Various modes of pre-heating the humidification fluid can be used, including heating the fluid reservoir, heating the fluid feed line, or having a special fluid pre-heating zone on the heating element before reaching an evaporation region. In accordance with certain embodiments, a check valve is disposed within the fluid feed line prior to the metering arrangement to prevent back-flow of the humidification fluid. In some embodiments, a safety valve is disposed within the fluid feed line prior to the metering arrangement to release pressure in the line due to pump failure, along with other possible causes.

The heater-plate controller represented in FIG. 2A can include a heated surface sub-system that monitors and controls the temperature of the heating element. A heating surface includes an area over which humidification fluid is distributed and vaporized by heat energy provided by the heating surface. A wicking element is provided over at least a portion of the heating surface. The wicking element is configured to receive and distribute a layer of the humidification fluid, the layer having a thickness, over the one or more portions of the heating surface that delivers the heat to vaporize the fluid. The wicking element can include paper, fabric, micro fiber, or microstructures, including microfluidic channels. The heating surface can include a heating plate, a resistive heating plate, or a circuit board having resistive tracks, to name a few. In some embodiments, the heating surface is a circuit board that is over-molded with a thermoplastic material. In some embodiments, multiple heating surfaces, or zones, may be used. Each heating surface may be maintained at the same or at different temperature levels. A heating surface temperature sensor is in thermal contact with the heating surface and in communication with a heating surface temperature controller. A surface heater, also in communication with the surface temperature controller, is configured to control the temperature of the heating surface, or multiple heating surfaces or zones, depending on the configuration of the heating surface.

Figure 2B:
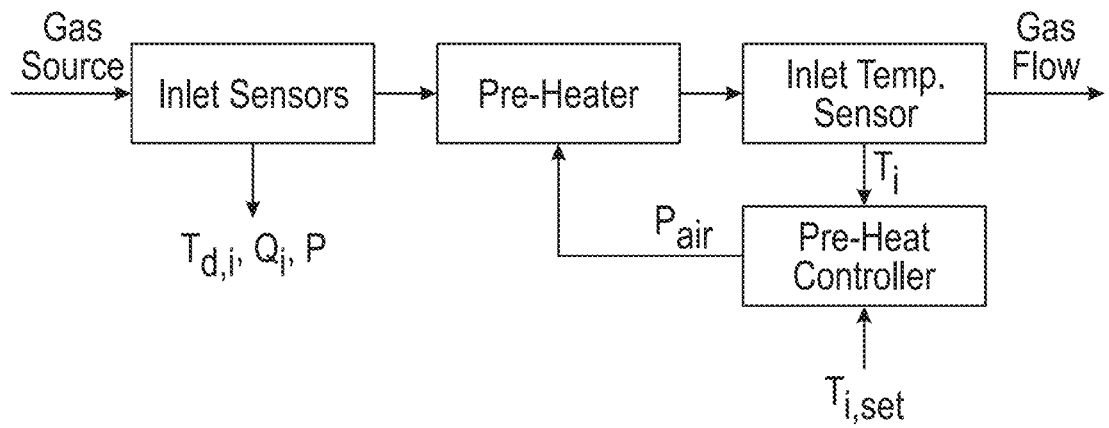
FIG. 2B is a functional block diagram of an inlet and pre-heating control sub-system in accordance with an embodiment of the present disclosure.
Figure 2C:
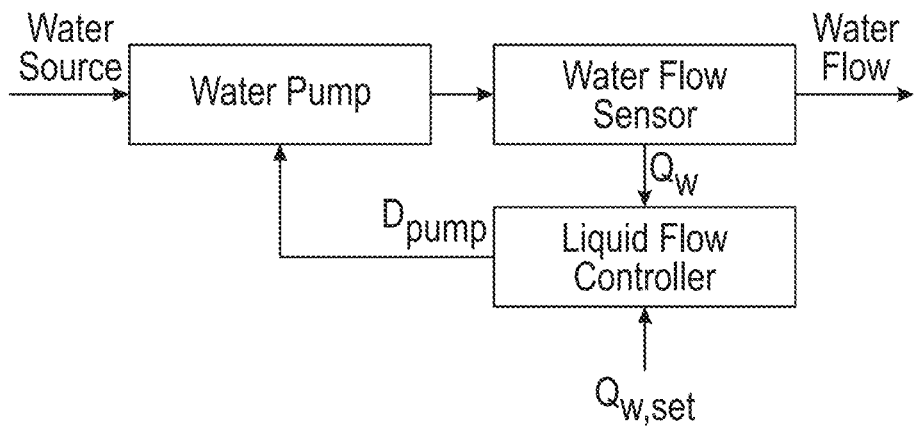
FIG. 2C is a functional block diagram of a water flow control sub-system in accordance with an embodiment of the present disclosure.
Figure 2D:
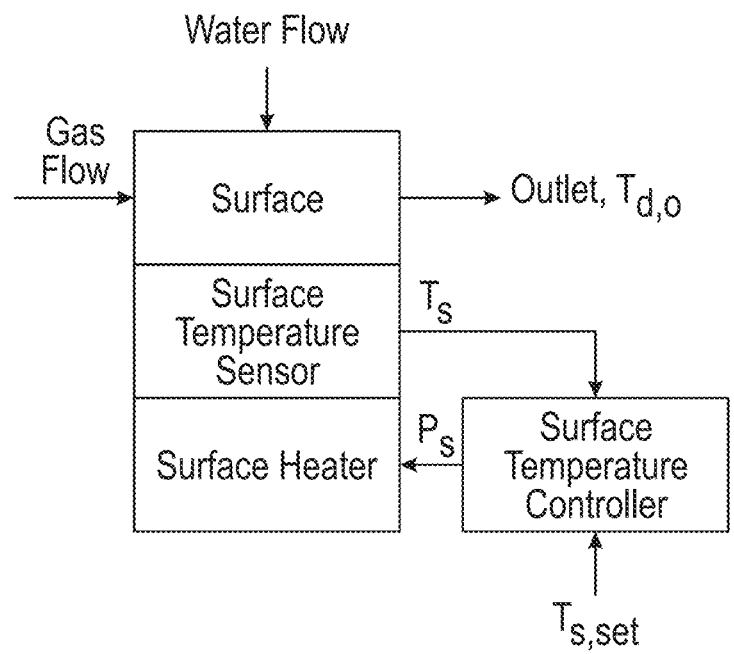
FIG. 2D is a functional block diagram of a heated surface control sub-system in accordance with an embodiment of the present disclosure.
Figure 2E:
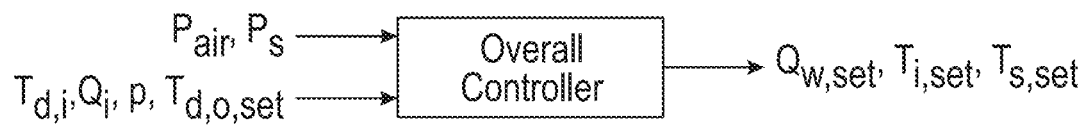
FIG. 2E is a functional block diagram of overall controller in accordance with an embodiment of the present disclosure.

FIGS. 2B-2D illustrate configurations of various control sub-systems that operate together with the configuration of an overall controller of FIG. 2E to deterministically control humidification systems as described herein.

FIG. 2B is a functional block diagram of an inlet and pre-heating control sub-system in accordance with an embodiment of the present disclosure. The pre-heater is not required, but may be included in some configurations. The inlet sensors can be replaced with equivalent measurements or appropriate assumptions and/or calculations as explained above. In some configurations, $T_i$ could also be controlled in an open loop fashion using the power equations. In some configurations, the ambient humidity $T_{d,i}$ can be sensed anywhere prior to humidification, although prior to the pre-heater is preferable. If placed after the pre-heater it could be merged with the inlet sensor $T_i$.

The inlet and pre-heating control sub-system of FIG. 2B can measure the air and/or gas coming into the system using inlet sensors (for example, those sensors described above in reference to FIG. 1E) to determine the ambient humidity $T_{d,i}$, the incoming gas flow rate, $Q_i$, and the incoming gas pressure, P. As described above, the gas can then be heated with a pre-heater, although this is not necessary in all embodiments. An inlet temperature sensor downstream of the pre-heater measures the temperature, $T_i$, of the heated gas and provides the measurement to the pre-heat controller. The pre-heat controller may compare $T_i$ with a calculated temperature, $T_{i,set}$, determined by the overall controller of FIG. 2E below and send signals to the pre-heater to adjust the temperature accordingly.

FIG. 2C is a functional block diagram of a water flow control sub-system in accordance with an embodiment of the present disclosure. In some configurations, the flow sensor and feedback (the liquid flow controller) can be omitted if a sufficiently well characterized and stable pump is used. The sub-system may also include a water pre-heater, as described elsewhere herein. A check valve may also be used prior to the pump to prevent back-flow of water. A safety valve may also be used prior to the pump if the pump is prone to failure. The system could also comprise a passive water meter and a flow sensor, for example, a pressure feed, such as a gravity feed, and a proportional valve instead of the pump.

In the configuration of FIG. 2C, water enters a water pump from a water source. The water pump may pump the water into the system. The water pump may be any of the pumps described above. A water flow sensor is positioned downstream from the pump and measures the flow rate of the water, $Q_w$, which is output to a liquid flow controller. The liquid flow controller provides a feedback loop whereby the water pump is adjusted based on a comparison of $Q_w$, and a calculated water flow rate, $Q_{w,set}$. The calculated water flow rate, $Q_{w,set}$ is determined by the overall system controller of FIG. 2E as described below.

FIG. 2D is a functional block diagram of a heated surface control sub-system in accordance with an embodiment of the present disclosure. Although only one surface is shown, multiple surfaces could be used. There could be multiple surface heating zones and multiple temperature sensors. In some configuration there are two heating zones and temperature sensors. An outlet temperature sensor could also be included to assist in control. The surface temperature sensor could be replaced or supplemented by using the resistance or other characterization of the surface heater. For example, in the current implementation the resistance of the copper tracking indicates the average heater temperature. In some configurations, it may be preferred that the surface temperature sensor give as close as possible measurement of the true surface temperature, which would benefit the evaporation models described above.

In the illustrated configuration of FIG. 2D, water flow and gas flow, for example, the outputs of the subsystems of FIGS. 2B and 2C, are routed over a surface. The surface may be a heating source as described throughout this application. The surface includes one or more surface temperature sensors which provide measurements of the surface temperature, $T_s$, to a surface temperature controller. The surface temperature controller provides a feedback and control mechanism whereby a surface heater, in thermal communication with the surface is adjusted. The surface temperature controller may compare $T_s$ to a calculated surface temperature, $T_{s,set}$. The calculated surface temperature, $T_{s,set}$ is determined by the overall system controller of FIG. 2E below.

FIG. 2E is a functional block diagram of overall controller in accordance with an embodiment of the present disclosure. FIG. 2E shows an example of an overall controller that ties the above three controllers of FIGS. 2B-2D together. As shown in FIG. 2E, in some configurations, there is no closed loop feedback on the outlet dew-point temperature, as the figure indicates that the control is simply an open-loop set-point based on the inputs. The input variables are split into two groups to signify that one group, $T_{d,i}$, $Q_i$, p, and $T_{d,o,set}$, is fundamental to the controller, while the other group can be omitted in simpler controllers. In the most basic controller, the three output variables may be set according to the fundamental system equations, in other words, $Q_{w,set}$ can be determined by equations 1-3, $T_{i,set}$ can be set to the desired output to the desired gas inlet temperature, and $T_{s,set}$ can be determined by equation 4. In some configurations, $P_{air}$, $P_s$, and any other extra variables are not used or only used as system checks.

Figure 3A:
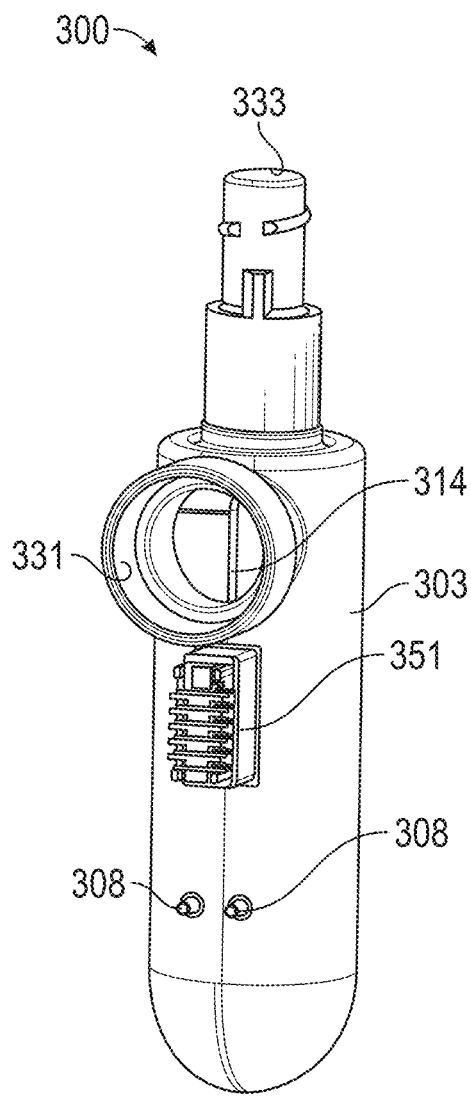
FIG. 3A is a schematic perspective view of an example integrated humidification system in accordance with one embodiment of the present disclosure.
Figure 3B:
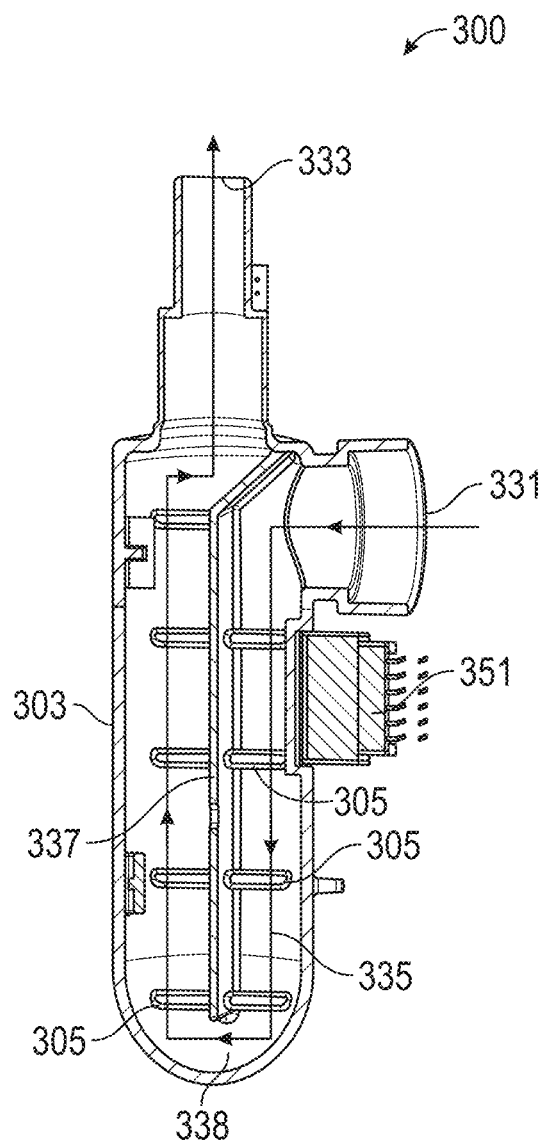
FIG. 3B is a schematic vertical cross-section view showing an air flow of the humidification system of FIG. 3A.
Figure 3C:
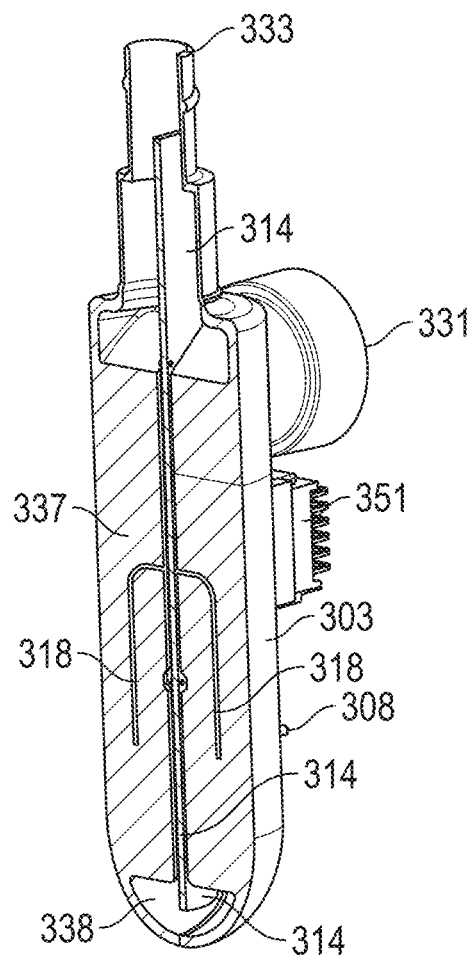
FIG. 3C is a schematic vertical cross-section view showing a water flow of the humidification system of FIG. 3A.
Figure 3D:
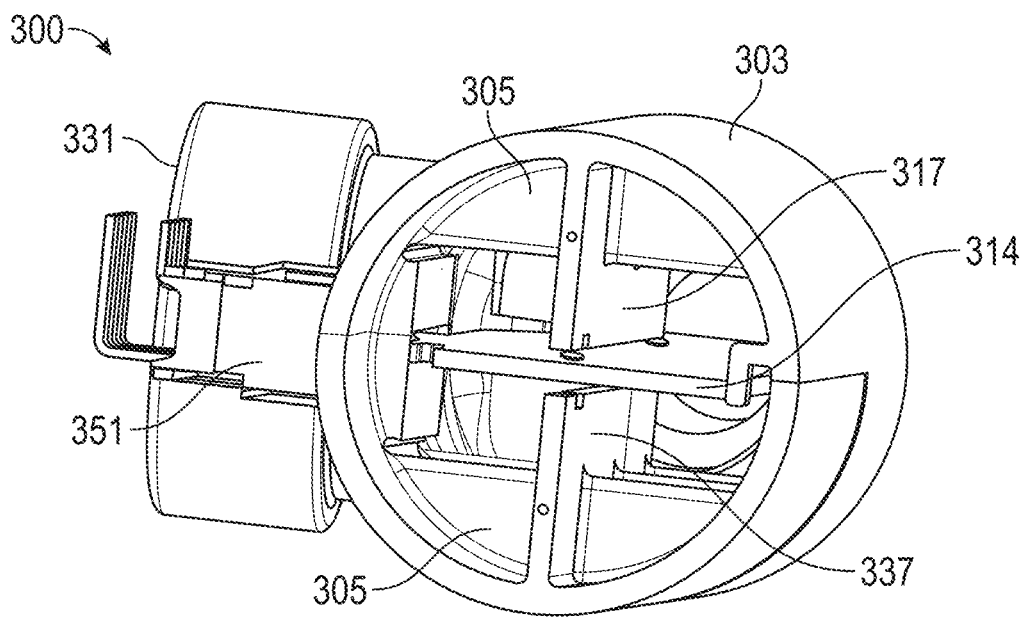
FIG. 3D is a schematic horizontal cross-section view of the humidification system of FIG. 3A.
Figure 3E:
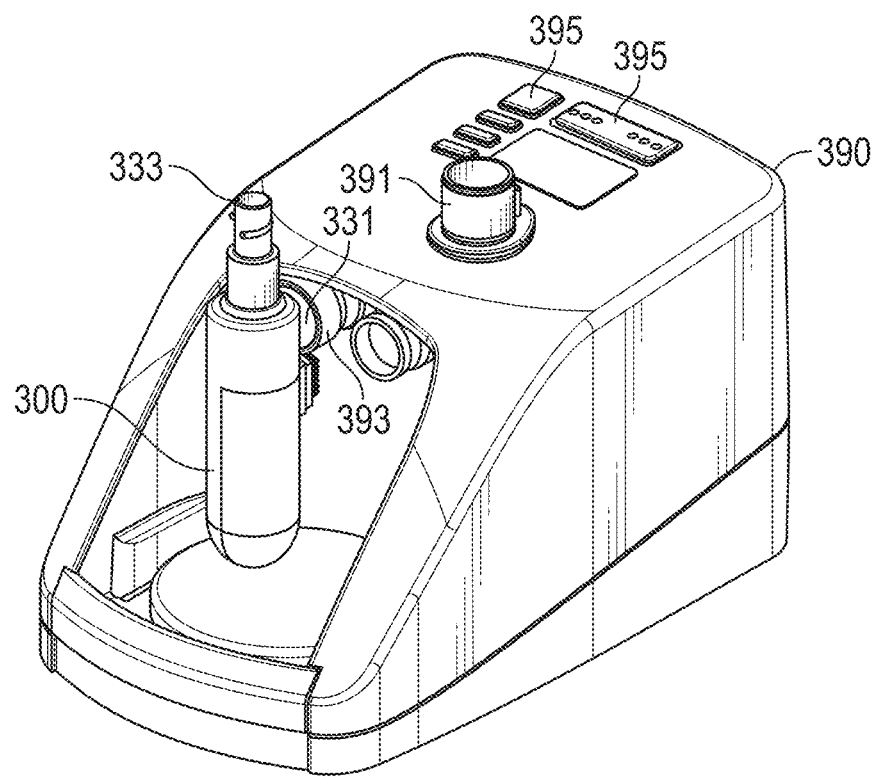
FIGS. 3E-3F show the humidification system 300 installed for use with a flow generation system.
Figure 3F:
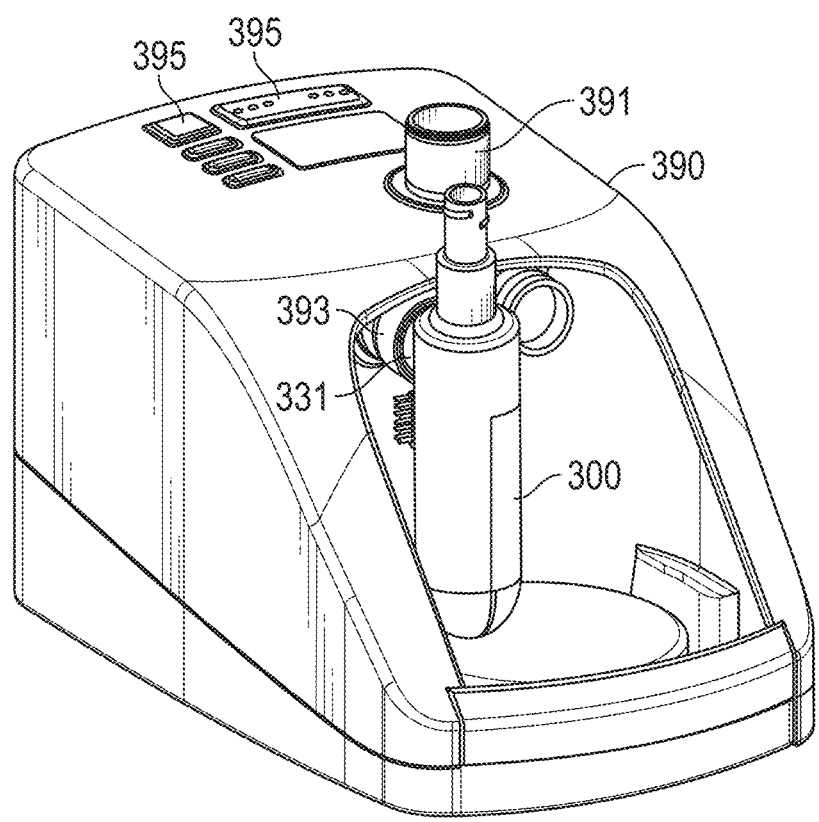

FIG. 3A is a schematic perspective view of an example integrated humidification system 300 in accordance with one embodiment of the present disclosure. FIG. 3B is a schematic vertical cross-section view showing an air flow of the humidification system 300. FIG. 3C is a schematic vertical cross-section view showing a water flow of the humidification system 300. FIG. 3D is a schematic horizontal cross-section view of the humidification system 300. In some configurations, the humidification system 300 can be a stand-alone humidifier using ambient air and relying on normal patient respiration to generate a flow of gases. In some configurations, the humidification system 300 can be an add on to a respiratory circuit for use with any flow generation system, for instance with a ventilator. FIGS. 3E-3F show the humidification system 300 installed for use with a flow generation system in an integrated system.

As shown in FIG. 3A, the humidification system 300 includes a housing 303, a gases inlet 331, a gases outlet 333. The gases inlet 331 is configured to receive gases into the humidification system 300. In some configurations, the gases inlet 331 is adapted to connect with a gases inlet tube, flow generation system, or other gases sources. The gases outlet 333 is configured to deliver humidified gases out of the humidification system 300 and to a patient. In some configurations, the gases outlet 333 is adapted to connect to a gases outlet tube, for example, a respiratory tube connected to a patient interface (for example, a cannula). The humidification system 300 also includes, one or more water inlets 308 configured to allow water received from a water flow controller into the humidification system 300. In some embodiments, the humidification system 300 includes an inlet and an outlet for water. In some embodiments, the humidification system 300 only includes inlets, as all water input into the system is evaporated to humidify the gas. The humidification system 300 also includes an electrical connector 351 for supplying power to the system and for communicating with various components thereof. The humidification system may also serve to provide power to the heated breathing tube and in-built sensors, such that the design acts as a conduit for downstream system components that require power or communications.

FIG. 3B is a schematic vertical cross-section view showing an air flow of the humidification housing of FIG. 3A. As shown in FIG. 3B the housing 303 defines a gases flow path 338. In this configuration, the gases enter the humidification system 300 at the gases inlet 331 and are directed downward by an interior wall 337. An opening 338 at the bottom of the interior wall 337 allows the gases to pass to the other side of the interior wall 337 where the gases are directed upwards and out of the humidification system 300 at the gases outlet 333. The housing 303 may include internal baffles 305. Along the flow path 335 the gases are humidified by vaporized water evaporating off of the heating element 314. The heating element 314 can be partially seen through the gases inlet 331 in FIG. 3A and a cross-sectional view of the heating element 314 is visible in FIGS. 3C and 3D. An example configuration of the heating element 314 is described as heating element 400 in reference to FIGS. 4A-4C below.

FIG. 3C is a schematic vertical cross-section view showing a water flow of the humidification housing of FIG. 3A. In the illustrated configuration, water entering at the inlets 308 is distributed through channels 318 so as to contact the heating element 314. In the illustrated configuration, the channels 318 are partially located within the interior wall 337.

FIG. 3D is a schematic horizontal cross-section view of the humidification housing of FIG. 3A. As shown in FIG. 3D, the heating element 314 divides the housing 303 in a first direction and the internal wall 337 divides the housing 303 in a second direction, orthogonal to the first direction. Thus, the heating element 314 is immersed in the flow path. In some configurations this is preferred as it to effectively doubles the surface area, provides a dramatic increase in power efficiency, makes the surface temperature reading more accurate, and allows the housing 303 to be kept relatively cool (and therefore, safe). In the embodiment of FIG. 3D, baffles 305 are included in the air flow path.

FIGS. 3E-3F show the humidification system 300 installed for use with an embodiment of flow generation system 390. The flow generation system 390 can include a gases inlet 391 for connecting to an external gases source and a gases outlet 393 that can be adapted to connect to the gases inlet 331 of the humidification system 300. In the illustrated configuration, the flow generation system 390 includes a plurality of input controls 395. In some configurations, the flow generation system 390 can be an Airvo available from Fisher & Paykel Healthcare of Auckland, NZ.

Figure 4A:
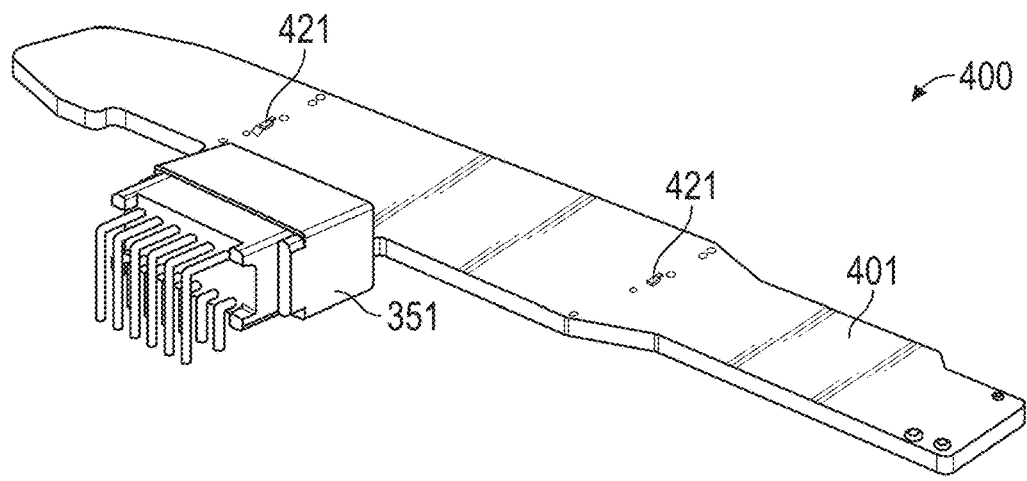
FIG. 4A is a schematic perspective view of a printed circuit board heating element in accordance with an embodiment of the present disclosure.
Figure 4B:
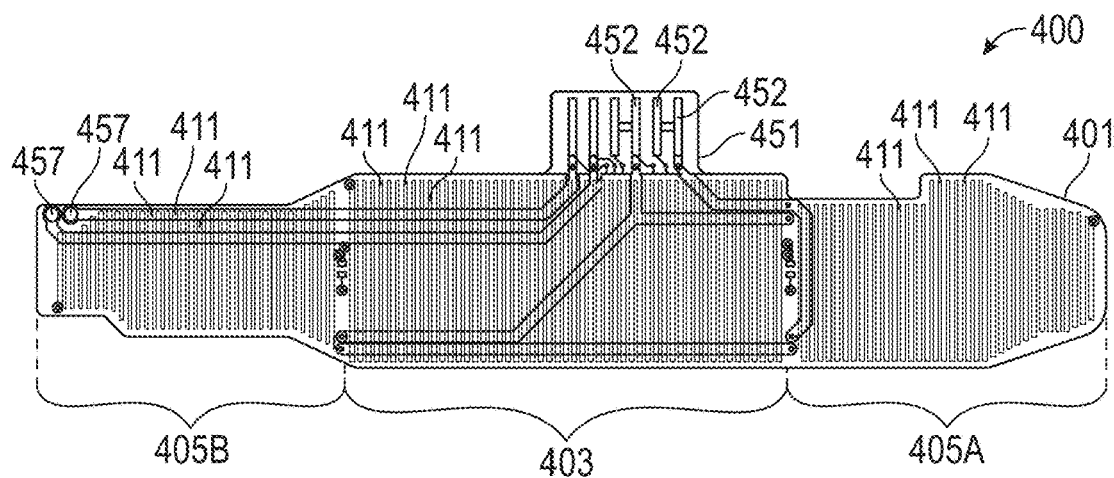
FIG. 4B is a schematic top view of a printed circuit board heating element in accordance with an embodiment of the present disclosure.
Figure 4C:
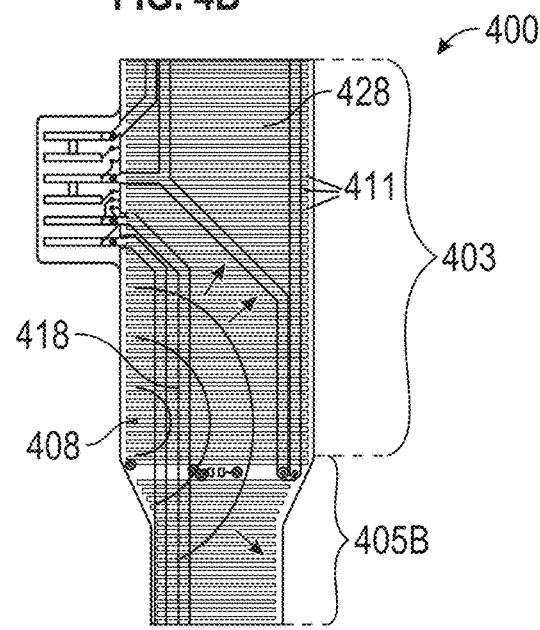
FIG. 4C is a partial schematic top view of a printed circuit board heating element in accordance with an embodiment of the present disclosure.

FIG. 4A is a schematic perspective view of a heating element 400 in accordance with an embodiment of the present disclosure. FIG. 4B is a schematic top view of the heating element 400. FIG. 4C is a partial schematic top view of the heating element 400. In some configurations, the printed circuit board heating element 400 may be used as the heating device 314 of the humidification system 300 described above in reference to FIGS. 3A-3F, or as any other heating device described herein (for example, the heating device 114 of FIGS. 1A-1E).

The heating element 400 may include a printed circuit board 401 for providing heating. The printed circuit board 401 may have a plurality of resistive tracks 411. The resistive tracks 411 may be copper. An outer surface of the heating element 400 may include a wicking surface. The wicking surface may be provided by an over-molding on the printed circuit board 401. The over-molding may have micro-channels in it (the micro-channels are described in greater detail below). The over-molding may be a thermoplastic material. The heating element 400 may have modular zones. For example, in the illustrated embodiment, the resistive tracks 411 are divided into three modular zones, 403, 405A, 405B. In some configurations, the modular zones 405A and 405B are connected in series. In some configurations, the heating element 400 may have a first zone configured to pre-heat the water and a second zone configured to vaporize the water as will be described in reference to FIG. 4C. A single zone could be wet, and that single zone could be powered. This gives flexibility in the Controller. Alternatively, the entire heater surface can be powered, and the entire heater surface can be kept wet rather than operating the isolated zones.

As shown in FIG. 4B, the heating element 400 may include electrical contacts 457 (for either power transfer or communication) that can used to power additional components of a respiratory humidification system. For example, electrical contacts 457 may provide power to a heated breathing tube (HBT). As another example, the electrical contacts 457 may be used to power or communicate with additional sensors (e.g., temperature sensors, pressure sensors, or other sensors as described herein).

The micro-channels may provide a wicking surface. The wicking surface may work synergistically with the pre-heating of the gas to allow the heating surface to be maintained at a relatively low temperature. This is because lower temperatures require larger surface areas to generate the requisite vapor flux, and larger areas require more efficient mechanisms for spreading the liquid so as to recruit more of the heated surface for evaporation.

Figure 5A:
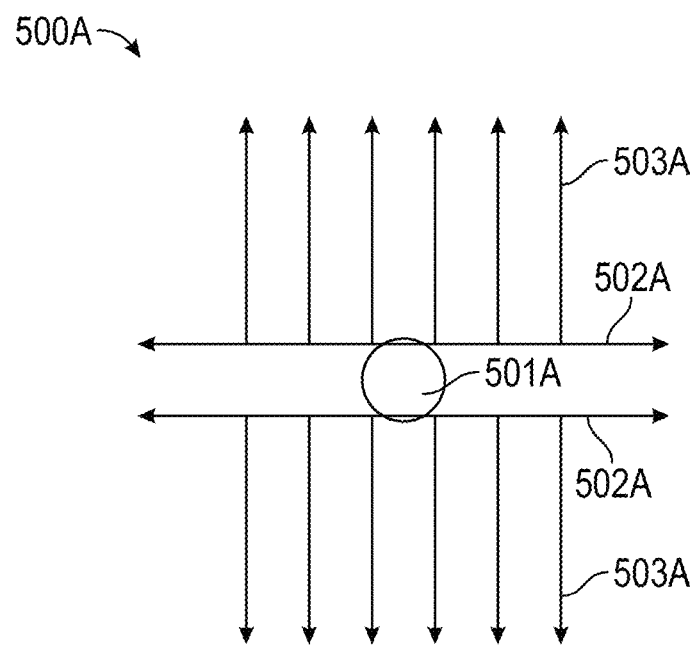
FIG. 5A is a schematic diagram illustrating a grid-structured micro-channel water distribution pattern in accordance with an embodiment of the present disclosure.
Figure 5B:
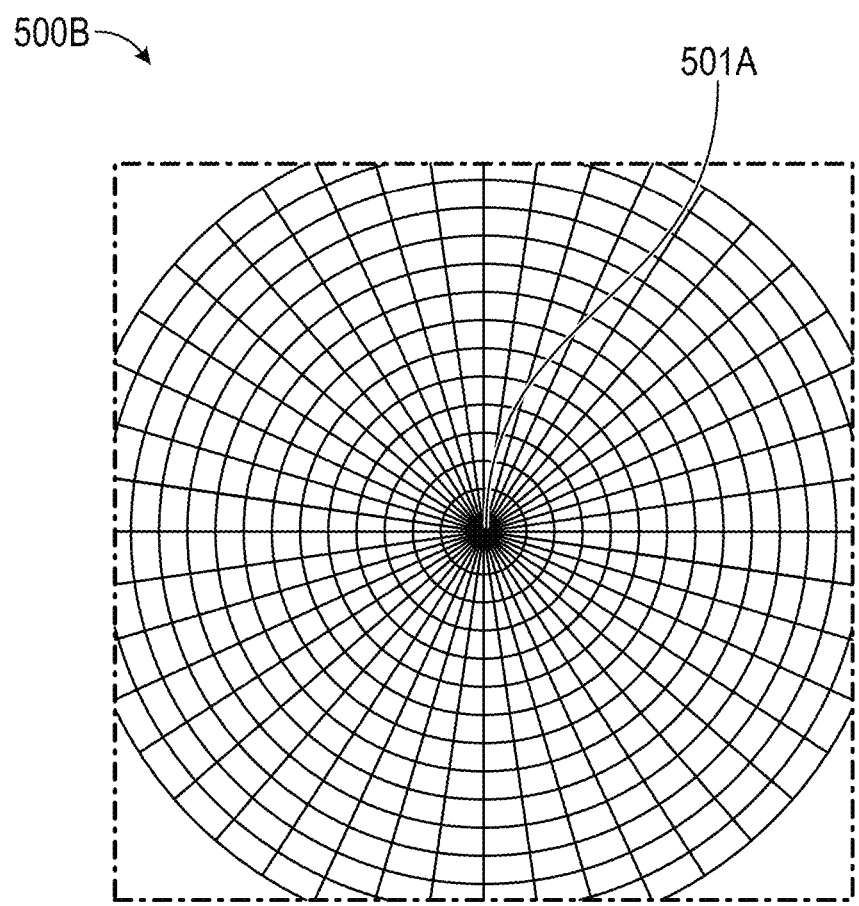
FIG. 5B is a schematic diagram illustrating a radial micro-channel water distribution pattern in accordance with an embodiment of the present disclosure.

In some configurations, micro-channels may be small scale (for example, micro-scale) grooves formed on a surface. The surface may be either flat or curved. In some configurations, the micro-channels may be highly ordered. In some configurations, the micro-channels are arranged in a pattern (see, for example, FIG. 5A, showing one example of a grid structured pattern, and FIG. 5B, showing one example of a radial pattern; these examples are non-limiting and other patterns are possible). In some configurations, the purpose of the micro-channels is to spread a liquid across a surface thereby increasing its surface area for a given volume. In some configurations, the micro-channels have a substantially uniform cross-sectional profile along their length. For example, the micro-channels may have a circular or semi-circular, elliptic or semi-elliptic, rectangular, triangular (V-shaped), or trapezoidal cross-sections. In some configurations, the micro-channels may include rounded edges and/or corners. In some configurations, the micro-channels may have a variable cross-sectional profile that changes over the length of the micro-channel. For example, a micro-channel can become deeper and/or wider along its length. The micro-channels may be "open" micro-channels, which include at least one side open to the environment. For example, a micro-channel may be a V-shaped groove formed into a surface, and liquid in or on the micro-channel may be open to the environment at least the open side of the V. Such micro-channels may facilitate evaporation of the liquid as the open side of the micro-channel provides a place for the evaporated liquid to go. For example, an open side of an open micro-channel may open into a gas passageway. Liquid on or in the micro-channel may evaporate, and the evaporated liquid may be entrained in the gases flowing through the gas passage way. In some configurations, the micro-channels may have a depth (which can also be considered a height) that ranges from between 1-1000 μm. In some configurations, the depth of a micro-channel is between 20-200 μm. In some configurations, the width of a micro-channel can be between 1-1000 μm. In some configurations, the width of a micro-channel is between 20-200 μm. In some configurations, the tilt of the side walls of a micro-channel can range from 0-45 degrees. As used herein, the tilt of the sidewalls is measured between the wall and vertical (in other words, between the wall and an axis extending normal to the surface in which the micro-channel is formed). That is, a wall tilt of 0 degrees represents a totally vertical wall. For example, if the side walls of a micro-channel include a 0 degree wall tilt, the micro-channel may be substantially square shaped, and the top of the square may be open. As another example, if the side walls of a micro-groove include a 45 degree wall tilt, the micro-channel may be substantially V-shaped if the tilted side wall directly intersect, or substantially trapezoidally shaped if the side walls intersect a horizontal flat bottom surface of the micro-channel, and the top of the micro-channel may be open. In some configurations, the tilt of the side walls of a micro-channel can range from 5-20 degrees. The micro-channels can spread the liquid by wicking (capillary action) or, in some situations, by gravitational flow of the liquid through the channels. In some configurations, the micro-channels may be defined by protrusions extending above a surface, where the micro-channel is formed by the space between the protrusions.

In some configurations, the heating element 400 includes one or more sensors for measuring the temperature of the surface of the heating element 400. The one or more sensors may be thermistors 421. In some configurations, the heating surface temperature may be calculated at least in part, by determining a resistance level or other characteristic of the heating element 400. The resistance level of the heating element may be used to indicate an average temperature of the heating surface. The heating element may be arranged to deliver a higher power density in a specified region of the heating element as compared to a power density delivered to other regions of the heating element. The specified higher density region of the heating element may be located at an outlet of a water supply to the heating surface. The specified higher density region of the heating element may be located at a water pre-heating area on the heating surface. The respiratory humidification system may include a temperature sensor at the outlet location of the gases channel, which may act as a safety check.

The resistive tracks 411 and/or sensors, for example, the thermistors 421 may be electrically connected to electrical contacts 452 positioned on a contact region 451 of the printed circuit board 401. The contact region 451 can be positioned so as to mate with the electrical connector 351 of the humidification system 300.

In some configurations, the heating element 400 is configured to provide some "pre-heating" to the water. This can be accomplished, in some configurations, simply by increasing the track (and therefore power) density at the area(s) where the water is introduced. This zone would have the power density increased by the extra amount required to heat the water within a small area. For example, as shown in FIG. 4C, if water is introduced to the heating element 400 at location 408 and the surface of the heating element is configured to wick the water across the heating element 400 in the direction of the arrows, the heating element 400 can include a greater density of resistive tracking 411 at locations at and around location 418 (in other words, near location 408 where the water is introduced) and a lower density of resistive tracking 411 at locations around location 428 (in other words, distanced from location 418).

The power required for latent and sensible heating are, approximately, $P_L = L\dot{m}$ and $P_s = c_p \dot{m}(T_s - T_w)$ (where L is the latent heat of vaporization, $c_p$ is the specific heat capacity of water, $\dot{m}$ is the water flow rate, $T_s$ is the surface temperature, and $T_w$ is the water temperature). The ratio of sensible to latent heat is then $$\frac{P_s}{P_L} = \frac{c_p \dot{m}(T_s - T_w)}{L\dot{m}} = \frac{c_p(T_s - T_w)}{L}.$$

Because the water flow rate cancels out, this is constant enough for us to design a zone of power density some fixed ratio higher than the rest of the plate and achieve the desired effect. This is not always precise because $T_s - T_w$ can change by a significant amount, but, in some configurations, there is no need for it to be overly precise.

Pre-heating of the water is generally a less of important aspect of the system than pre-heating the air, because it is a smaller component of the total heat required (about half compared to the air) and has less impact on the evaporation and little impact on the outgoing gas conditions. Still, in some configurations the heating the water consumes up to 9% of the power in the system, so it is not insignificant. Without pre-heating, the impact this has is that there will be a temperature gradient across the surface as the water heats, which reduces the evaporation rate in those areas and makes the evaporation models more complex.

Another option for providing pre-heating for the water is to include a heater in the water supply line (i.e., between the pump/flow sensor and coupling to the surface), this could be a PTC (positive temperature coefficient) element, or a heating coil, or any other heater, in thermal contact with the water flow, which heats the water to the same temperature as the surface of the heating element 400.

While the heating element 400 has been described above in reference to heating water, a similar heating element 400 may also be used to heat gas, for example, as a gas pre-heater.

Figure 4D:
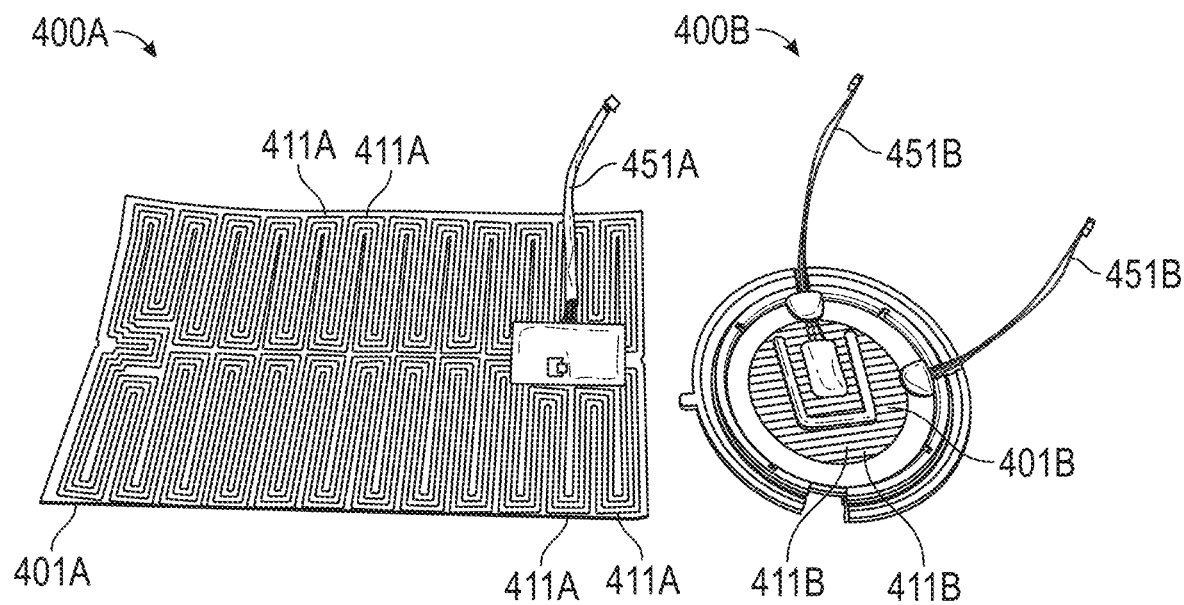
FIG. 4D illustrates a top schematic view of two embodiments of an etched foil heating element in accordance with an embodiment of the present disclosure.

FIG. 4D illustrate a top schematic view of two alternative embodiments of heating element 400A, 400B in accordance with an embodiment of the present disclosure. The heating elements 400A, 400B may include an etched foil film 401A, 401B. The etched foil film 401A, 401B may include a plurality of resistive tracking 411A, 411B. The heating elements 400A, 400B may each also include electrical connections 451A, 451B.

Figure 4E:
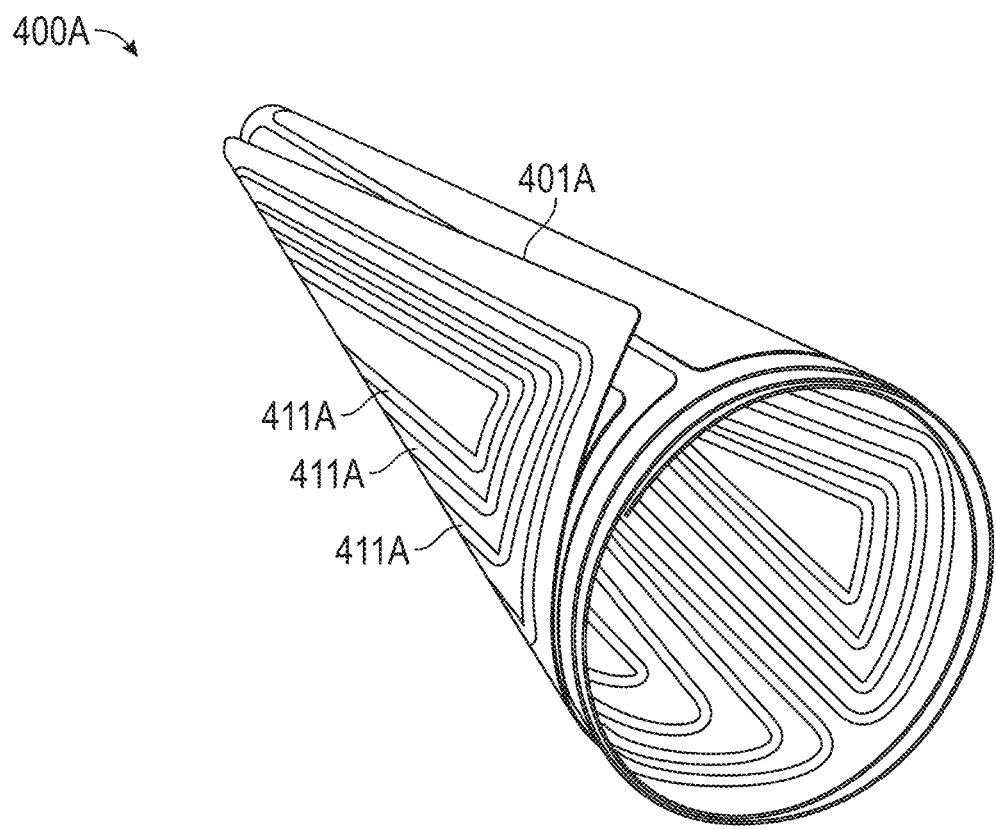
FIG. 4E illustrates an embodiment of an etched foil heating element in a rolled configuration.

FIG. 4E illustrates an embodiment of the heating element 400A in a rolled configuration.

In some configurations, a humidification system includes various components, for example, a distribution and/or wicking system, to deliver the humidification fluid to the heating element. In some configurations, it is preferred to deliver water to the heating element surface across the entire surface, in other words, to saturate it. It is important to realize that the distribution/wicking system needs to be able to sustain a flow rate. In some configurations, it is not enough to have water distribution over the surface, if that distributor cannot wick the water fast enough to keep the heating element saturated. In some configurations it is preferred to sustain a liquid flow rate of up to 5 mL min$^{-1}$.

A distribution and/or wicking system may include two parts: the wicking surface, which distributes the water across the surface, and the coupling, which connects the water supply to the surface at one or more points. The coupling can also do some of the water distribution (e.g., by coupling the water over a region or line rather than at a point). The technologies that can be used for both coupling and wicking include, but are not limited to: fabrics/papers (for example, Kimberly-Clark Hydroknit); micro-channels; hydrophilic coatings (for example, Lotus Leaf Coatings HydroPhil); capillary/contact wicks (custom designs) and/or porous polymers (for example, Porex fibres)

The requirements for the coupling depend heavily on the nature of the surface. If the surface is isotropic (wicks the same in all directions) then the coupling only needs to couple the water to the surface at a single point. If the surface is anisotropic (depends on direction) some additional features will be required to account for this, i.e., it will need to actually direct the water over some region to ensure that the wicking is even. It also depends on the hydrophobicity of the surface—a hydrophilic surface readily absorbs the water so the coupling only needs to bring the water into loose contact with the surface, but a hydrophobic surface requires a coupling which needs to "force" the water against the surface to prevent it from merely "rolling" off, or provide an intermediate mechanism with a greater affinity to the humidification fluid, at the interface with the surface.

For example, the fabric of the wicking surface may be very close to isotropic and essentially hydrophilic so that a point source is sufficient. Bringing a tube that delivers the liquid into contact with the surface may be sufficient to generate flow (up to a certain surface size and depending on orientation). In some configurations, and on some substrates such as silicone, the wicking surface comprises micro-channels that may only wick in the direction of the channels, and that possess poor hydrophilicity. When using surfaces that wick in one direction and/or are not very hydrophilic it may be beneficial to have a distributor that holds the water in place until it is drawn away by the micro-channels, and that also may direct it along the other (e.g., perpendicular) direction.

In some configurations, a wicking surface can be a micro-channeled surface, which can include parallel channels in only one direction; a small set of distribution channels connected to a larger number of main channels; and/or channels distributed radially from a single point, among other possible configurations. A wicking surface may also be an absorptive fabric or paper, a super-hydrophilic coated surface, or, a thin porous media.

In some configurations, a coupling can be a length of wicking media bonded to the surface, which could include a porous or fibrous polymer; a fabric/paper, and/or a hydrophilic section. A coupling could also be a second surface forming an acute angle with the wicking surface, which draws the water by capillary action, which could include a flat slide, such as a glass slide, against the surface, at low angle, or alternatively a circular bar against the surface, forming a low contact angle at the point of contact. A wicking surface could also include a cavity in contact with the surface, which could include a flat face with a water-supplied cavity facing directly, and pressed against, the surface a C-shaped tube connected along an edge of the surface. In some configurations, any of these coupling methods can be a line source (useful if the surface is anisotropic, e.g., the micro-channels, in which case it is perpendicular to the surface's main wicking direction; for example, a thin section of porous polymer laid across the channels); a point source (useful if the surface is isotropic or contains built-in water distribution); a radial source; or multiple line/point/radial sources (which may be useful if there are two separate wicking surfaces (e.g., sides of the heater plate) or the wicking speed of the surface is insufficient to saturate the surface from a single source).

Specific examples of wicking surfaces and/or couplings will now be described by way of example and not limitation.

FIG. 5A is a schematic diagram illustrating a grid-structured micro-channel water distribution pattern 500a in accordance with an embodiment of the present disclosure. The distribution patter 500a includes a water input area 501a, first micro-channels 502a, and second micro-channels 503a. The first micro-channels 502a can serve as distribution channels which distribute the water to the second micro-channels 503a. The second micro-channels 503a distribute the water across the surface. The grid-structured micro-channel water distribution pattern 500a can be applied to the surface of the heating element 400. The grid-structured micro-channel water distribution patter 500a is one example of a wicking element as described herein. In some configurations, the first micro-channels 502a move the water in a first direction and the second micro-channels 503a move the water in a second direction orthogonal to the first direction. However, the grid-structured micro-channel water distribution pattern 500a can be modified to include first micro-channels 502a oriented at other positions relative the second micro-channels 503a. In some configurations, the grid-structured micro-channel water distribution pattern 500a includes only first micro-channels 502a or only second micro-channels 503a. In general, grid-structured micro-channel water distribution pattern 500a is a system where the micro-channels distribute the water: the water is supplied to several distribution channels, which splits off onto many channels that wick across the bulk of the surface.

FIG. 5B illustrates a radial micro-channel water distribution pattern 500b in accordance with an embodiment of the present disclosure. FIG. 5B is a still image taken from a video showing the radial micro-channels wicking a fluorescent dye. The fluorescent dye was dropped onto the center point 501b and wicked outwards by the channels. The radial micro-channel water distribution pattern 500b includes micro-channels that spread radially from a center point 501b where the water is introduced. In some configurations, to keep the channel density the same the micro-channels may split as they radiate from the center point 501b. The radial micro-channel water distribution pattern 500b may also include circumferentially extending micro-channels.

Figure 6A:
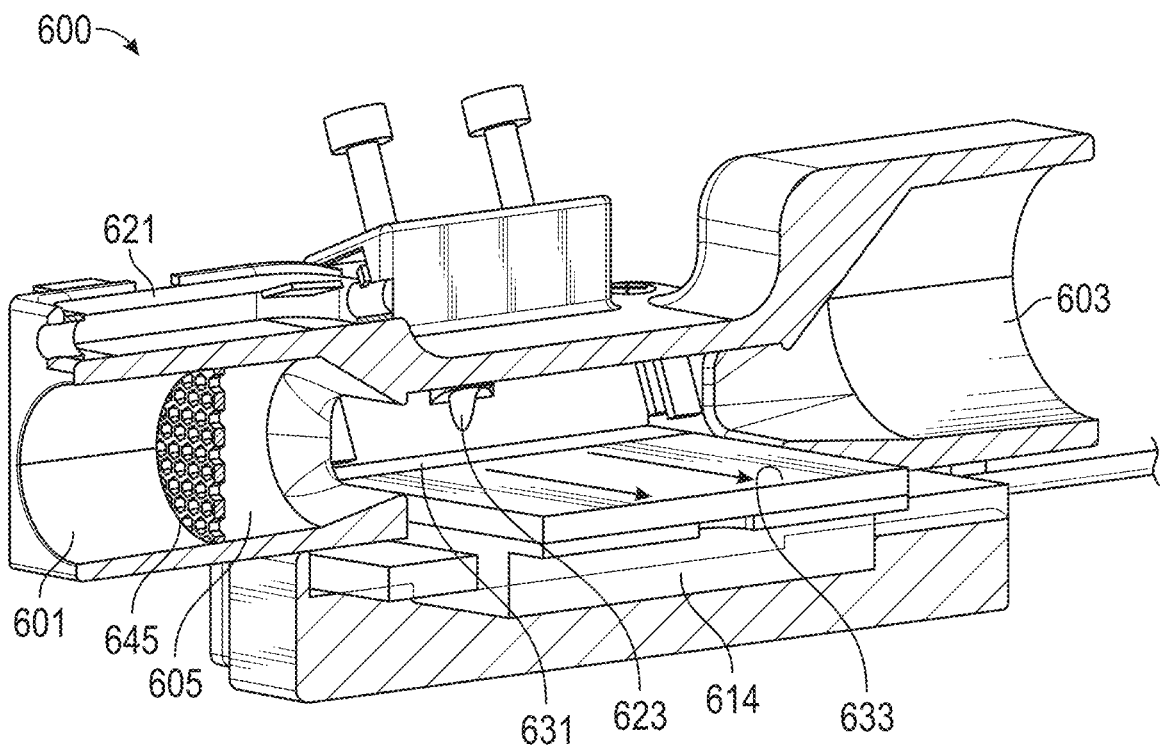
FIG. 6A is a schematic perspective axially sectioned view of a portion respiratory humidification system including an example of a coupling in accordance with an embodiment of the present disclosure.
Figure 6B:
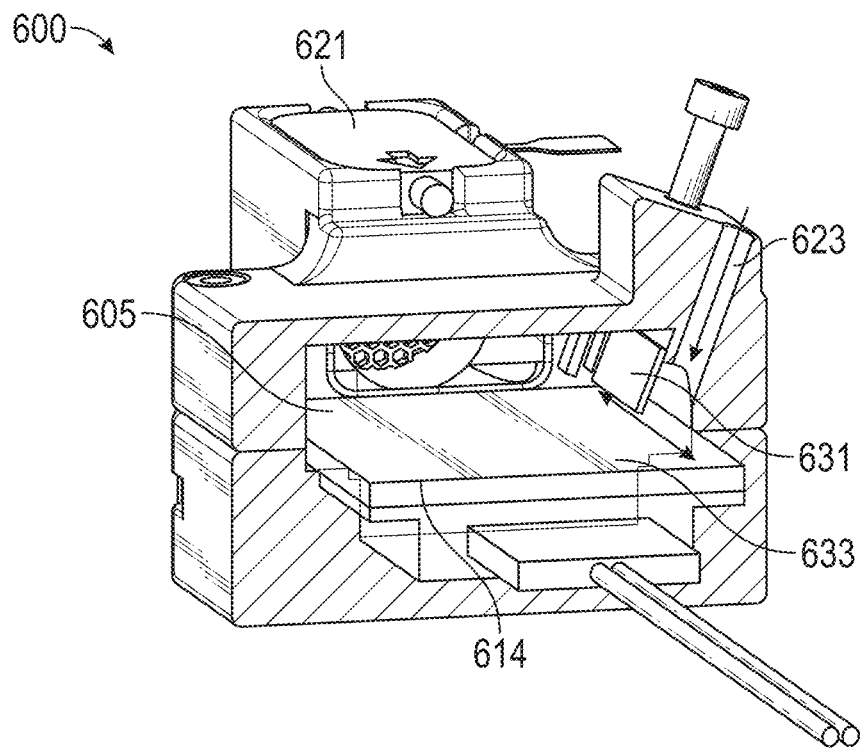
FIG. 6B is a schematic perspective sectioned side view of the respiratory humidification system of FIG. 6A including the example coupling.
Figure 6C:
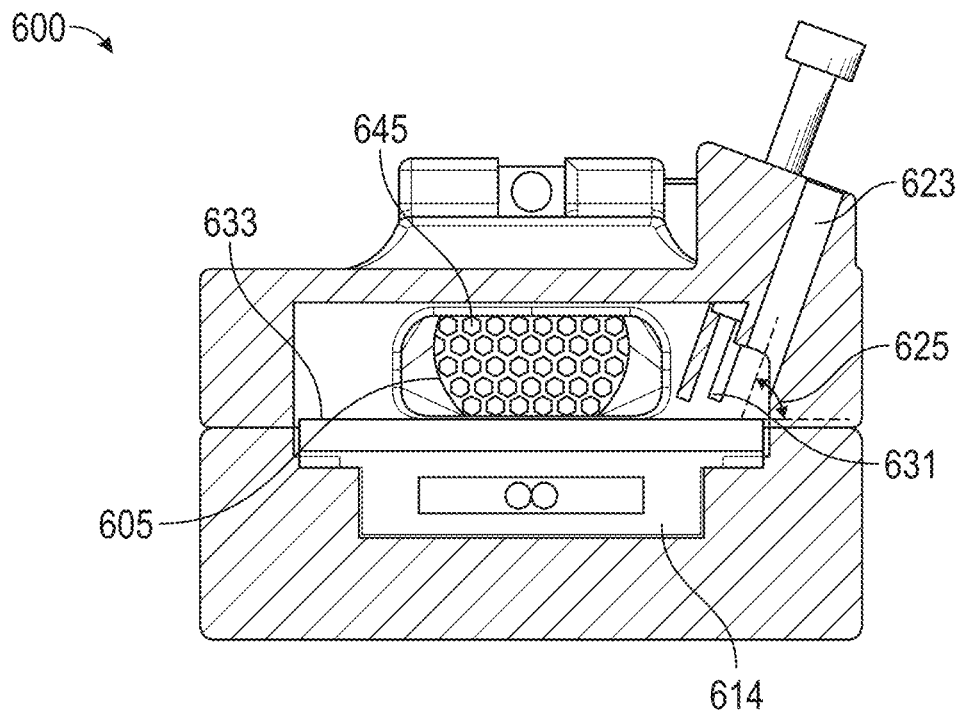
FIG. 6C is a schematic side view of the humidification system of FIG. 6A including the example coupling.
Figure 6D:
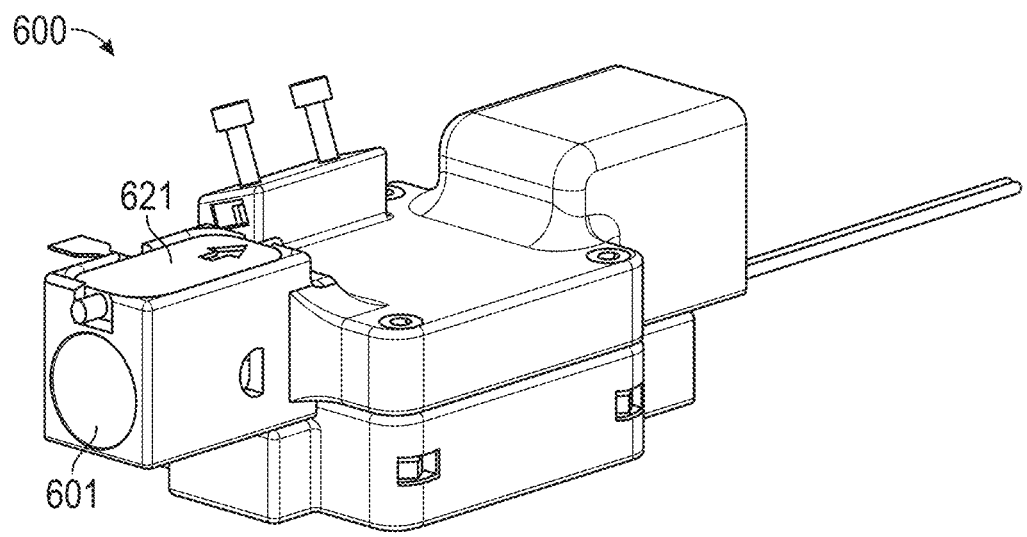
FIG. 6D is a schematic perspective assembled axial view of the humidification system of FIG. 6A.

FIG. 6A is a schematic perspective axially sectioned view of a respiratory humidification system 600 including a glass slide coupling 631 in accordance with an embodiment of the present disclosure. FIG. 6B is a schematic perspective sectioned side view of the respiratory humidification system 600 of FIG. 6A. FIG. 6C is a schematic side view of the respiratory humidification system 600 of FIG. 6A. FIG. 6D is a schematic perspective assembled axial view of the respiratory humidification system 600 of FIG. 6A. The glass slide coupling 631 may be considered a contact-angle/capillary line distributor.

In the illustrated embodiment, the respiratory humidification system 600 includes a gas inlet 601 and a gas outlet 603 with a gas flow channel 605 extending there between. As gases move from the inlet 601 to the outlet 603 they are humidified in the flow channel 605. The respiratory humidification system 600 also includes a micro pump 621 adapted to supply water from a water source into the system. The water is delivered from the micro pump 621 into the flow channel 605 via water pipe inlet 621. The respiratory humidification system further includes a glass slide coupling 631, which is held at an acute angle 625 (see FIG. 6C) against the surface 633 of the heating element 614. The surface 633 includes micro-channels extending in the direction of the arrows and perpendicular to the glass slide 631. The water supply tube 623 is placed at the intersection of the glass slide coupling 631 and surface 633. Because of the acute angle 625 (see FIG. 6C) between the glass slide coupling 631 and surface 633, the water is wicked along the intersection, and then wicked across the surface 633 by the micro-channels. Notably, the couple 600 only exposes the heater element 614 on one side; however, in some configurations the design could be modified to expose the heater element 614 on both sides. The respiratory humidification system 600 may also include a honey-comb gas diffuser 645 in the gas flow path 605.

Figure 7:
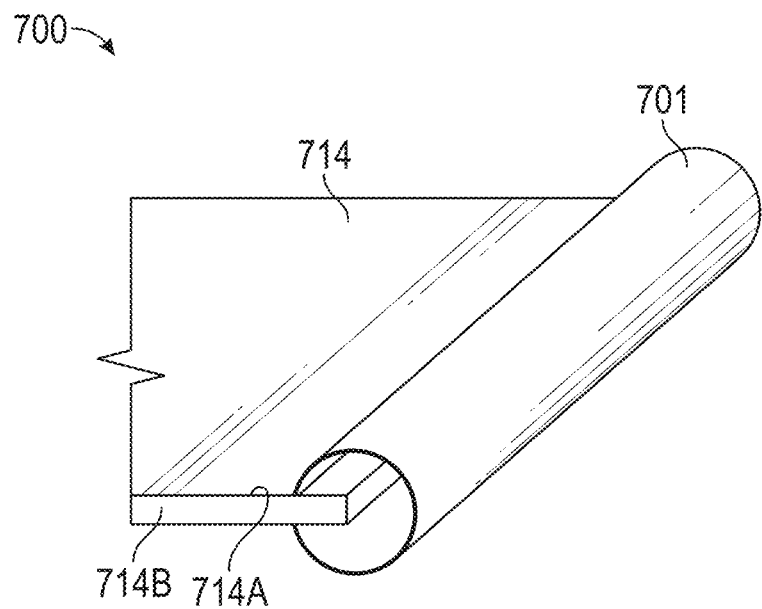
FIG. 7 is a schematic perspective diagram of a distribution tube coupling wrapped over an edge of a heating surface in accordance with an embodiment of the present disclosure.

FIG. 7 is a schematic perspective diagram of a distribution tube coupling 700 wrapped over an edge of a heating element 714 in accordance with an embodiment of the present disclosure. This drawing shows a tube 701 being used as a coupling or distributor. The tube 701 clips over the heating element 714, and then water is pumped into the tube 701. As the tube 714 fills, water is drawn across the heating element 714. Notably, the tube coupling 700 can distribute water onto both the top surface 714*a* and the bottom surface 714*b* of a heating element 714.

Figure 8:
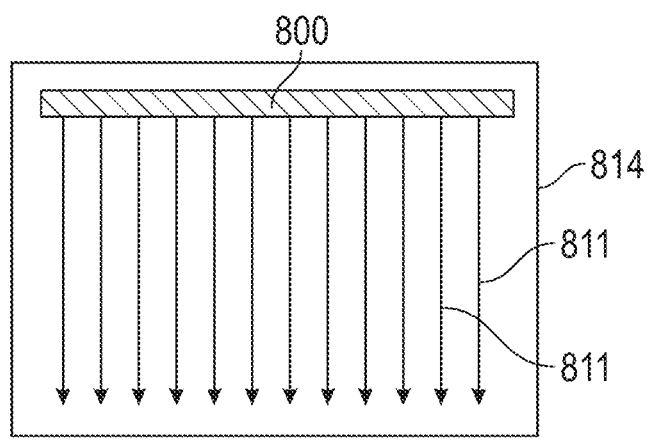
FIG. 8 is a schematic diagram of a porous media coupling in accordance with an embodiment of the present disclosure.

FIG. 8 is a schematic diagram of a porous media coupling 800 in accordance with an embodiment of the present disclosure. The coupling 800 is shown as a hashed strip extending along the surface of a heating element 814. The coupling may be, for instance, a piece of fabric. The water is dosed onto the fabric to allow the water to be distributed along the μ-channels. In some configurations, the coupling 800 may be a thin, porous media, such as a porous or sintered polymer.

Figure 9A:
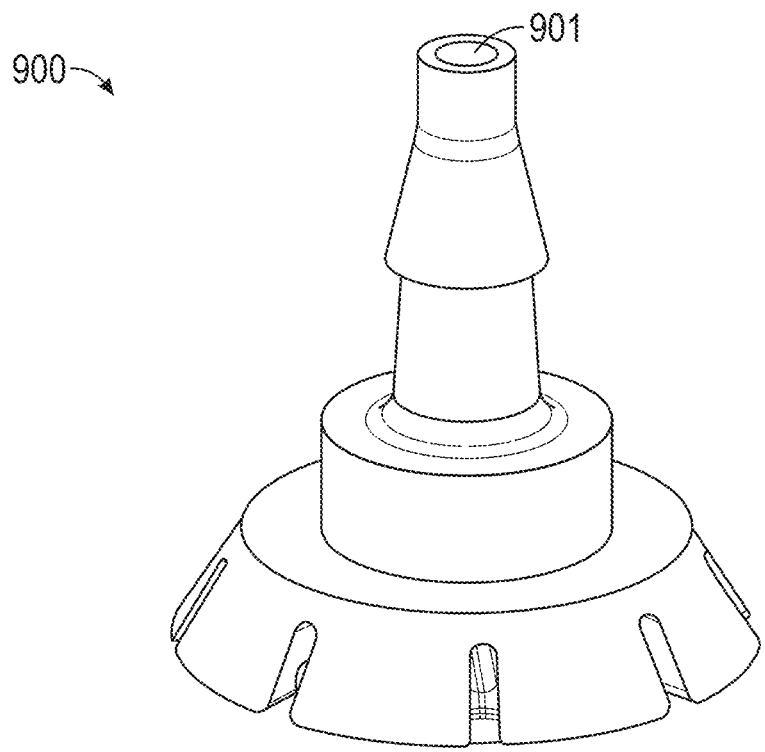
FIG. 9A is a schematic perspective view of a radial coupling in accordance with an embodiment of the present disclosure.
Figure 9B:
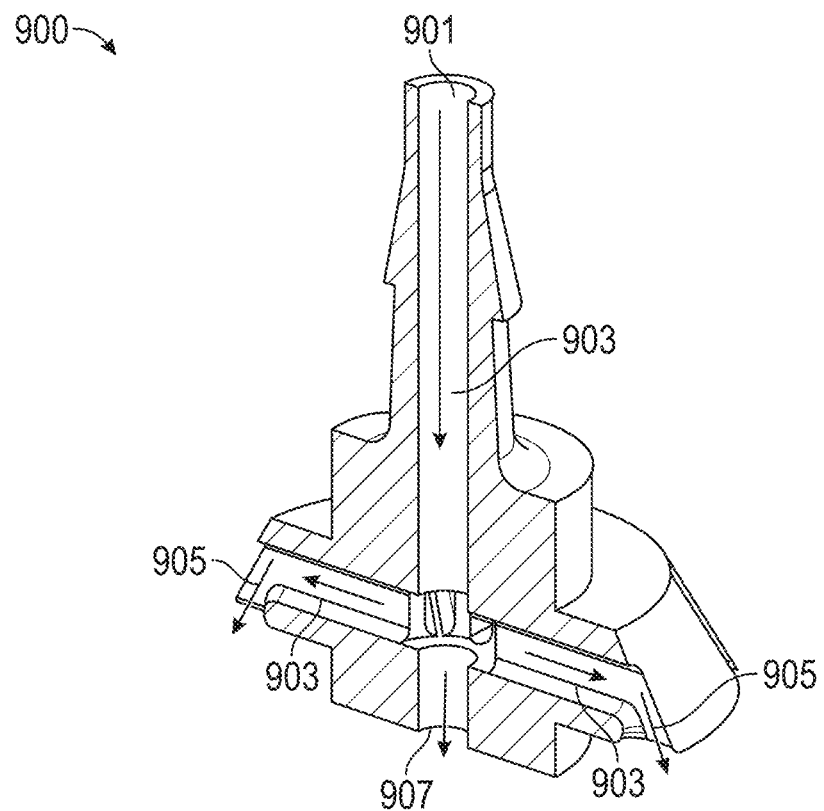
FIG. 9B is a schematic perspective sectional view of the radial coupling of FIG. 9A.

FIG. 9A is a schematic perspective view of a radial coupling 900 in accordance with an embodiment of the present disclosure. FIG. 9B is a schematic perspective sectional view of the radial coupling 900 of FIG. 9A. The radial coupling 900 may be considered a cavity/face coupling. In general, the coupling 900 pushes water against the surface of a heating element. In some configurations, the coupling 900 is configured to work with surfaces that are sufficiently hydrophilic or absorptive. In some configurations, the coupling 900 is adapted so that, when there are multiple outlets, the outlets are balanced, e.g., that the water doesn't simply favor one path and flow entirely in that direction.

The coupling 900 receives a supply of water at an inlet 901 and supplies it radially at the center of a heating element and to both sides. As shown in FIG. 9B, water flows down from the inlet 901 through a series of channels 903 to the heating element (not shown). The coupling 900 can include multiple outlets 905. In some configurations, the coupling 900 also delivers water through a central channel 907 that extends through a hole in the heating element to a similar system on the other side. In FIG. 9B arrows are added to illustrate the flow of water.

Figure 10A:
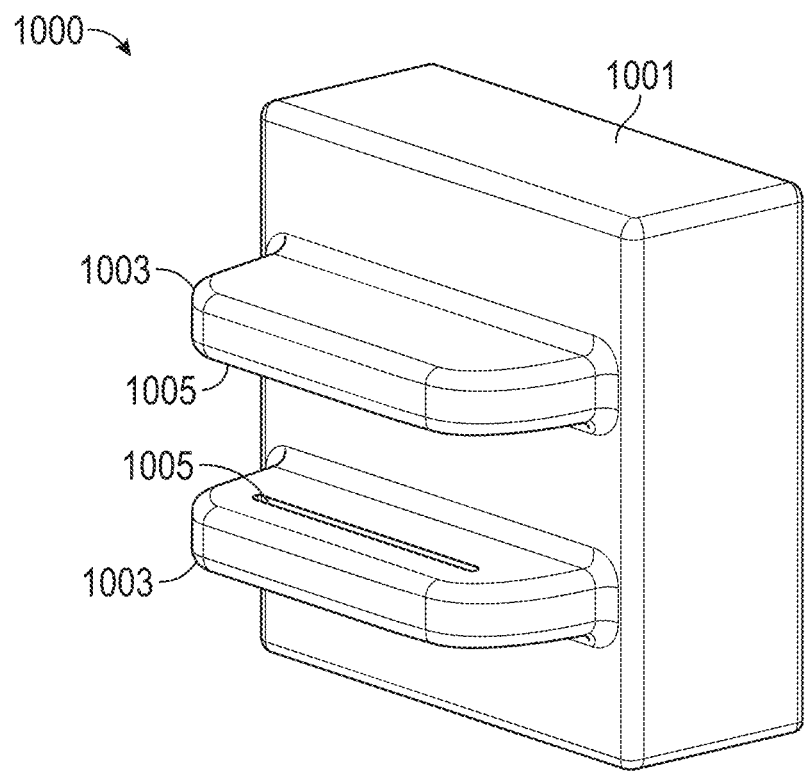
FIG. 10A is a schematic perspective view of a sandwich coupling in accordance with an embodiment of the present disclosure.
Figure 10B:
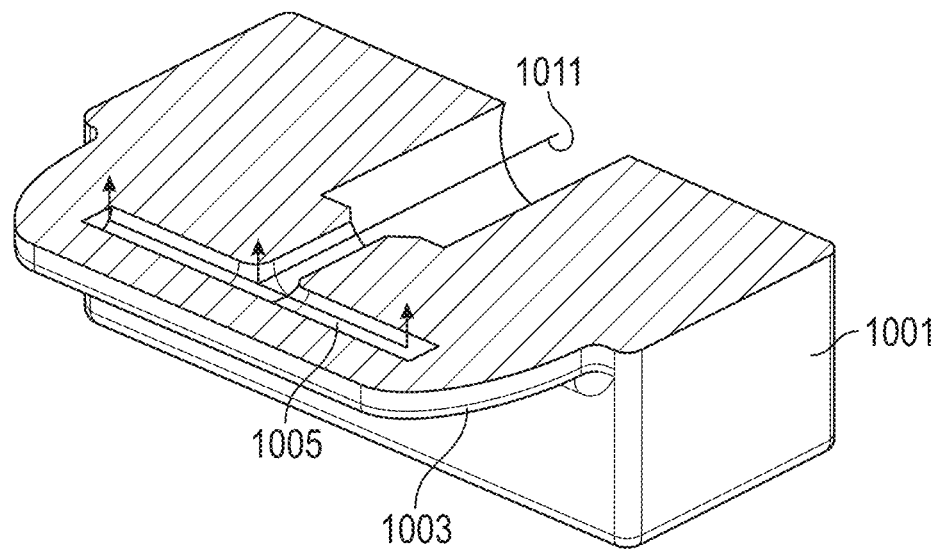
FIG. 10B is a schematic perspective sectioned view of the sandwich coupling of FIG. 10A.

FIG. 10A is a schematic perspective view of a sandwich coupling 1000 in accordance with an embodiment of the present disclosure. FIG. 10B is a schematic perspective sectioned view of the sandwich coupling 1000 of FIG. 10A. The coupling 1000 includes a body 1001 with one or more protruding sections 1003. A water outlet 1005 may be positioned on one of or each inward facing surface of the protruding sections 1003. As shown in FIG. 10B, the coupling 1000 includes a water inlet 1011 and internal channels that deliver water to the water outlet 1005. Arrows have been added to FIG. 10B to show the flow of water. A heating element (as shown in FIGS. 10C and 10D) may be positioned between the protruding sections 1003 and receive water from the outlets 1005.

Figure 10C:
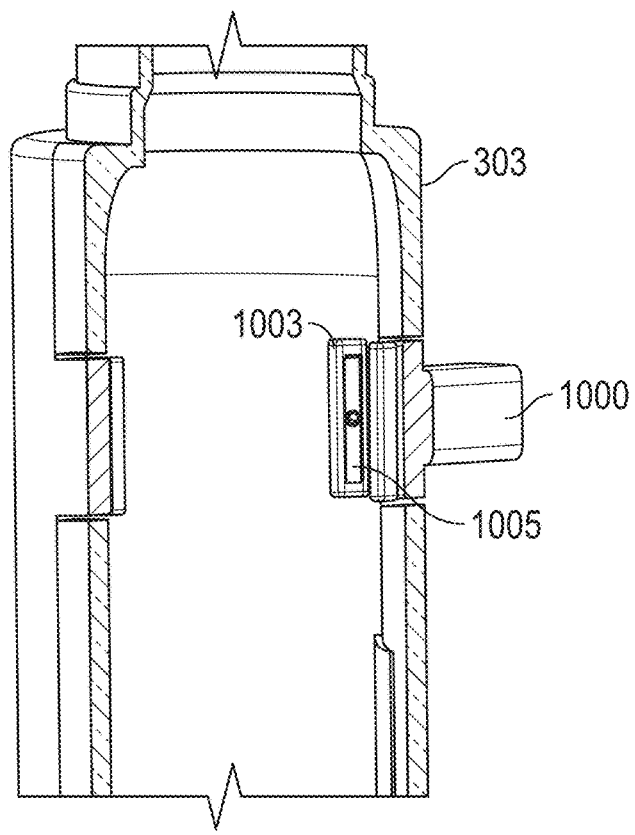
FIG. 10C is a schematic sectioned view of the sandwich coupling of FIG. 10A attached to a humidification housing in accordance with an embodiment of the present disclosure.
Figure 10D:
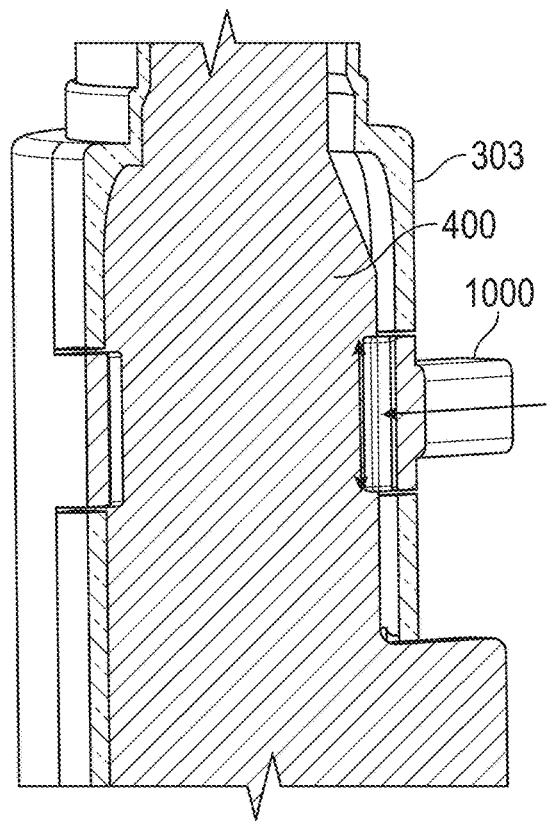
FIG. 10D is a schematic sectioned view of the sandwich coupling of FIG. 10A attached to a humidification housing that includes a printed circuit board heating element, in accordance with an embodiment of the present disclosure.

FIG. 10C is a schematic sectioned view of the sandwich coupling 1000 of FIG. 10A attached to a humidification housing 303 in accordance with an embodiment of the present disclosure. FIG. 10D is a schematic sectioned view of the sandwich coupling 1000 of FIG. 10A attached to a humidification housing 303 that includes a printed circuit board heating element 400, in accordance with an embodiment of the present disclosure. The housing 303 may be similar to the housing 303 of the humidification system 300 described in reference to FIGS. 3A-3D and the heating element 400 may be similar to the heating element 400 described in reference to FIGS. 4A-4C.

Embodiments of humidification systems as described herein have been tested and yield satisfactory results in terms of attainable dew-point temperature and control accuracy. For example, a dew point temperature, $T_d = 37°$ C. can be achieved for gas flows up to approximately 45 L min$^{-1}$ and at sea-level, dropping to approximately $T_d = 35°$ C. at a flow of 60 L min$^{-1}$. This is consistent with the maximum power attainable with the specific PCB design utilized.

Figure 11A:
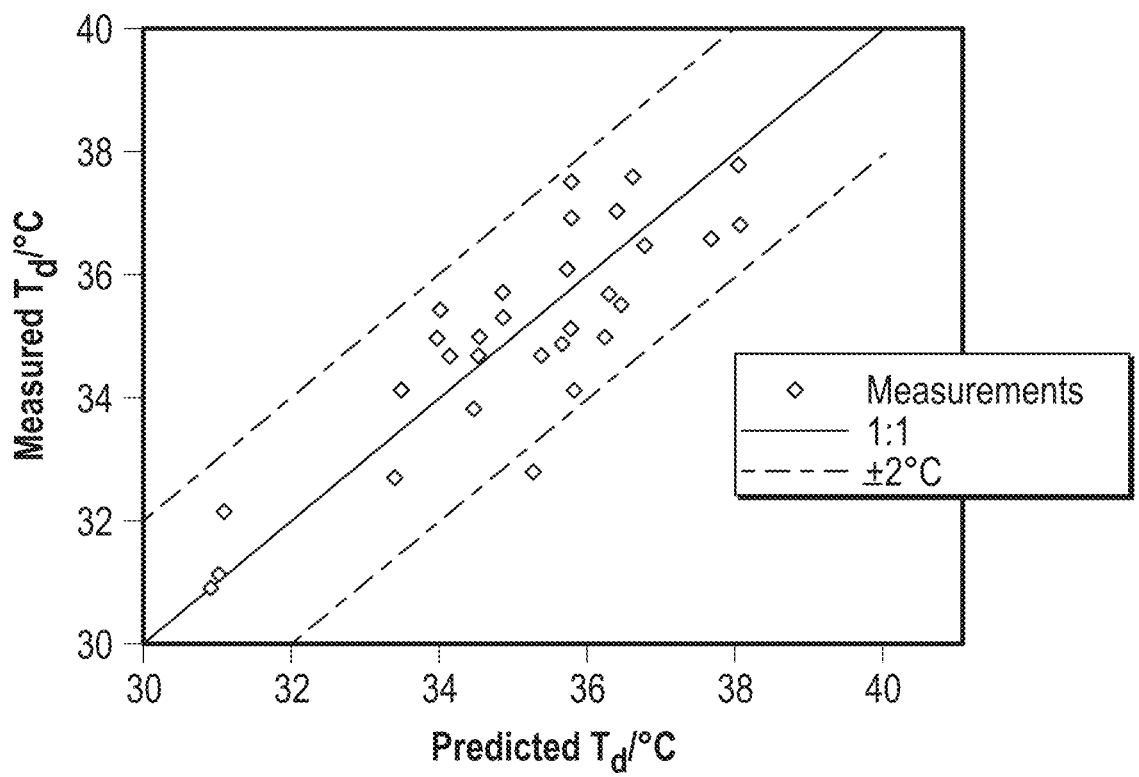
FIG. 11A is a plot of a dew point temperature accuracy of a respiratory humidification system in accordance with an embodiment of the present disclosure.
Figure 11B:
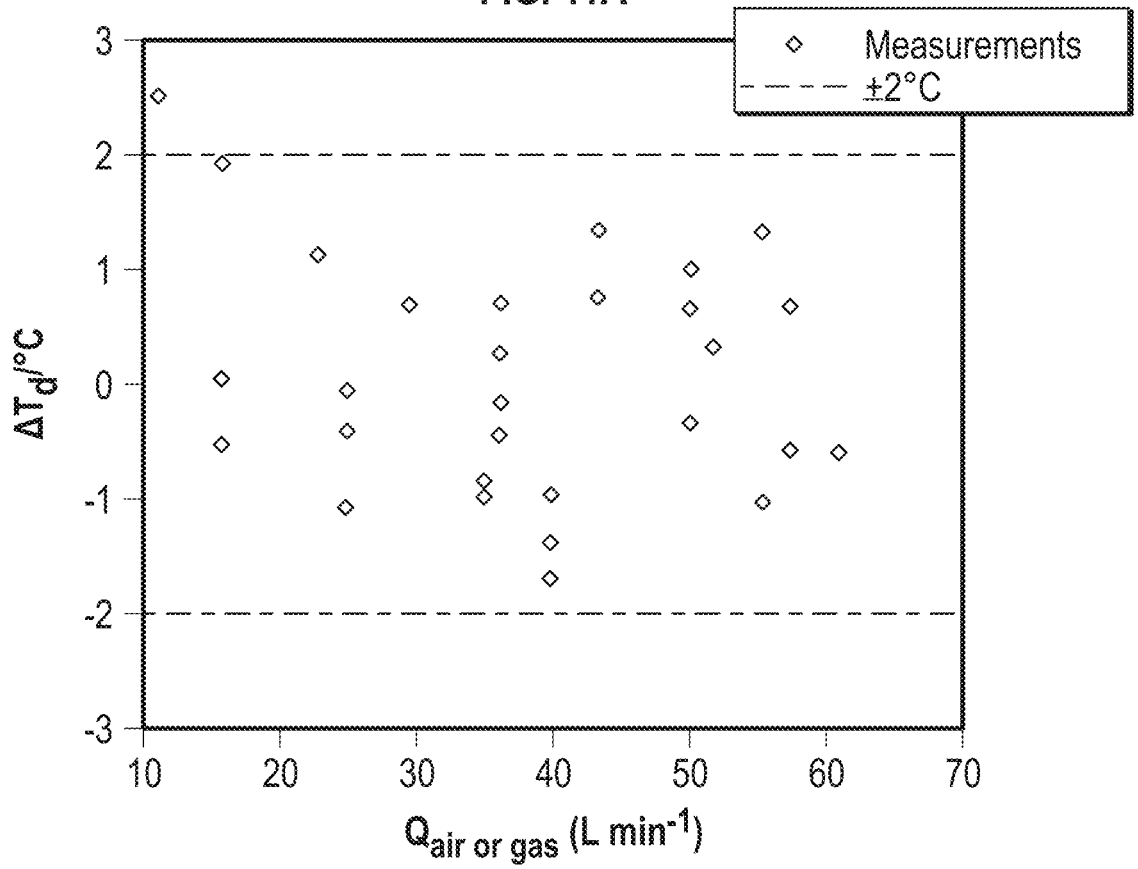
FIG. 11B is a plot of a dew point temperature error across air flow rate of a respiratory humidification system in accordance with an embodiment of the present disclosure.

FIGS. 11A and 11B show the accuracy performance of a respiratory humidification system in accordance with an embodiment of the present disclosure. The system was operated under open-loop control mode as described above across a range of flows and dew-points, with the dew-point temperature being measured independently at the outlet, and the dew-point temperature predicted by the system being calculated by inverting Eq. 3:

$$T_{d,0} = h_s^{-1}\left(\frac{Q_w}{Q_{air,i}} + h_s(T_{d,i}p), p\right) \qquad \text{Eq. 20}$$

FIG. 11A is a plot of a dew point temperature accuracy of the tested respiratory humidification and shows the measured dew point temperature plotted against the predicted dew point temperature. Two points where the heater-plate saturated due to under-power are not visible on the plot, but can be ignored since this condition is detectable. Most of the points are within ±2° C. of measured dew-point temperature. FIG. 11B is a plot of a dew point temperature error across gas flow rate of the tested respiratory humidification system.

Figure 12A:
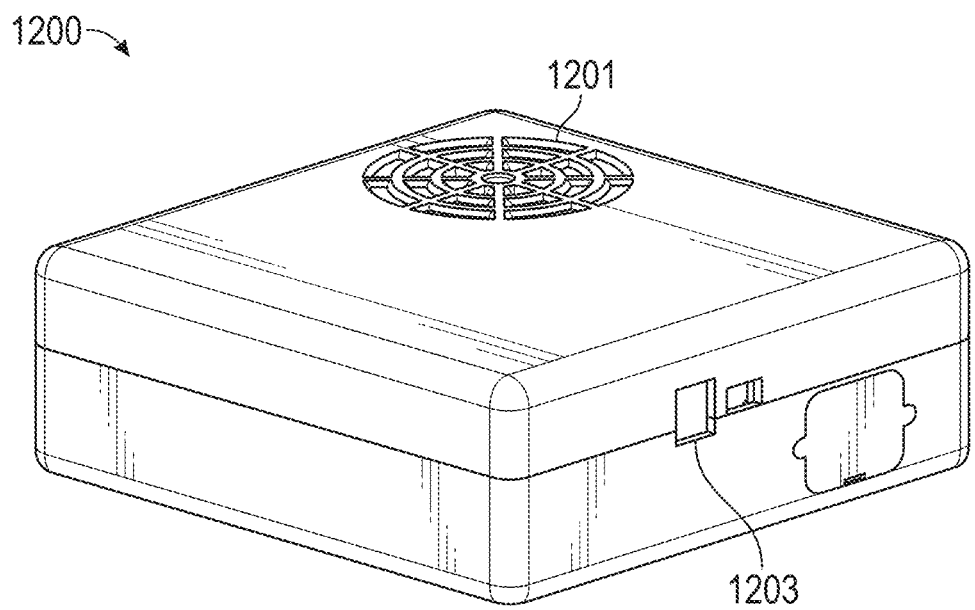
FIG. 12A is a schematic perspective view of an alternative embodiment of a humidification system in accordance with an embodiment of the present disclosure.
Figure 12B:
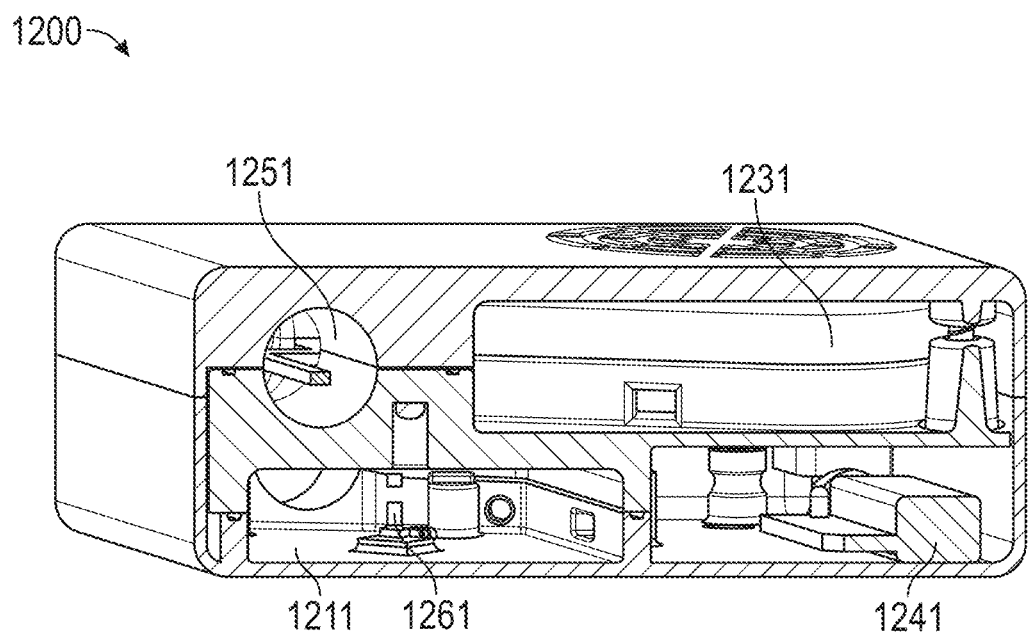
FIG. 12B is a schematic cross-section view of the humidification system of FIG. 12A.
Figure 12C:
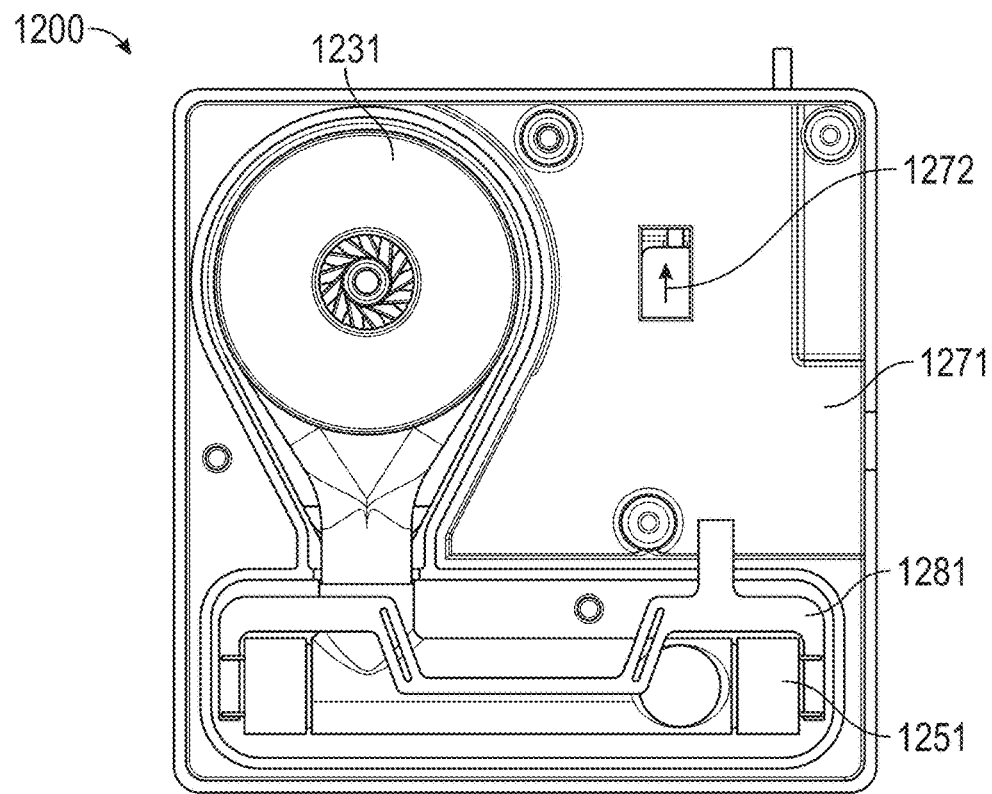
FIG. 12C is a schematic cross-section view showing the top layer of the humidification system of FIG. 12A.
Figure 12D:
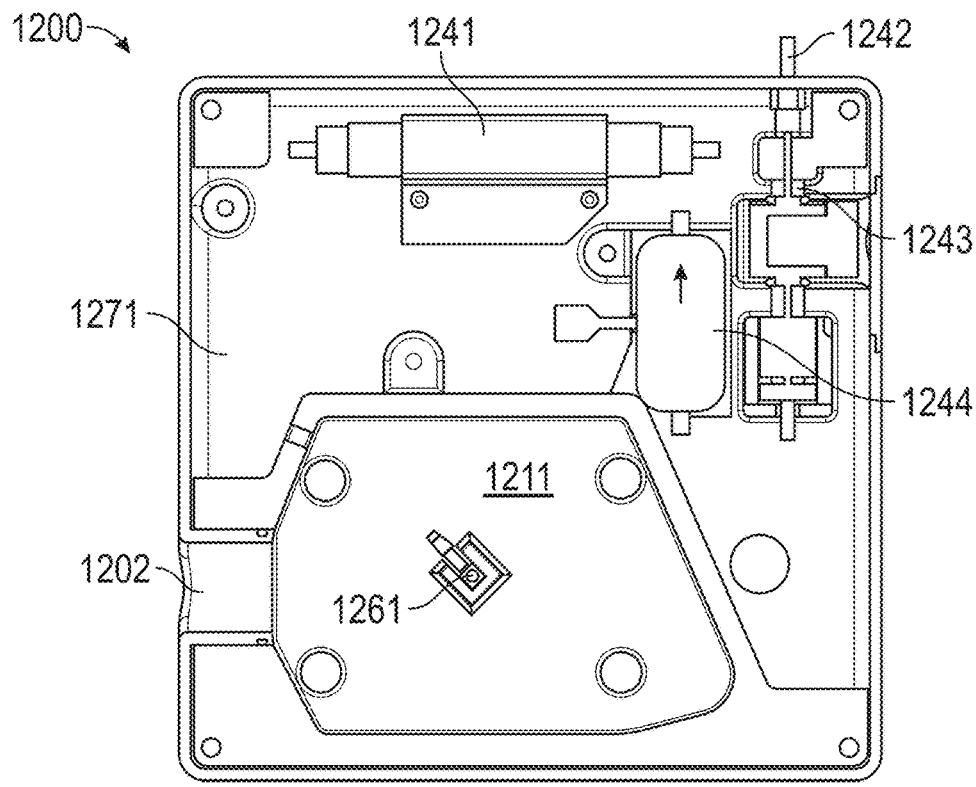
FIG. 12D is a schematic cross-section view showing the bottom layer of the humidification system of FIG. 12A.

FIG. 12A is a schematic perspective view of an alternative embodiment of a humidification system 1200 in accordance with an embodiment of the present disclosure. FIG. 12B is a schematic cross-section view of the humidification system 1200 of FIG. 12A. As shown in FIG. 12B, the humidification system 1200 includes a top layer and a bottom layer. FIG. 12C is a schematic cross-section view showing the top layer of the humidification system 1200 of FIG. 12A. FIG. 12D is a schematic cross-section view showing the bottom layer 1200 of the humidification system of FIG. 12A.

The humidification system 1200 includes a gas inlet 1201 and a gas outlet 1202. The humidification system can include a blower 1231 configured to move gas from the gas inlet 1201 to the gas outlet 1202. The inlet 1201 and outlet 1202 may be connected by a channel. A flow sensing device 1251 and a gas sensing device 1281 may be located within the channel. The humidification system 1200 includes power/communication connectors 1203.

The humidification system 1200 can include a heater surface cavity 1211 configured to receive a heating element as described elsewhere herein. The heating surface cavity also includes a water dosing section 1261 which may be configured with a coupling to apply water to the heating element. The water dosing section 1261 may be in fluid communication with a liquid flow module 1241, a water inlet 1242, a check valve 1243, and micro pump 1244. The humidification system 1200 may also include an electronics cavity 1271 accessible via a port 1272.

Figure 13:
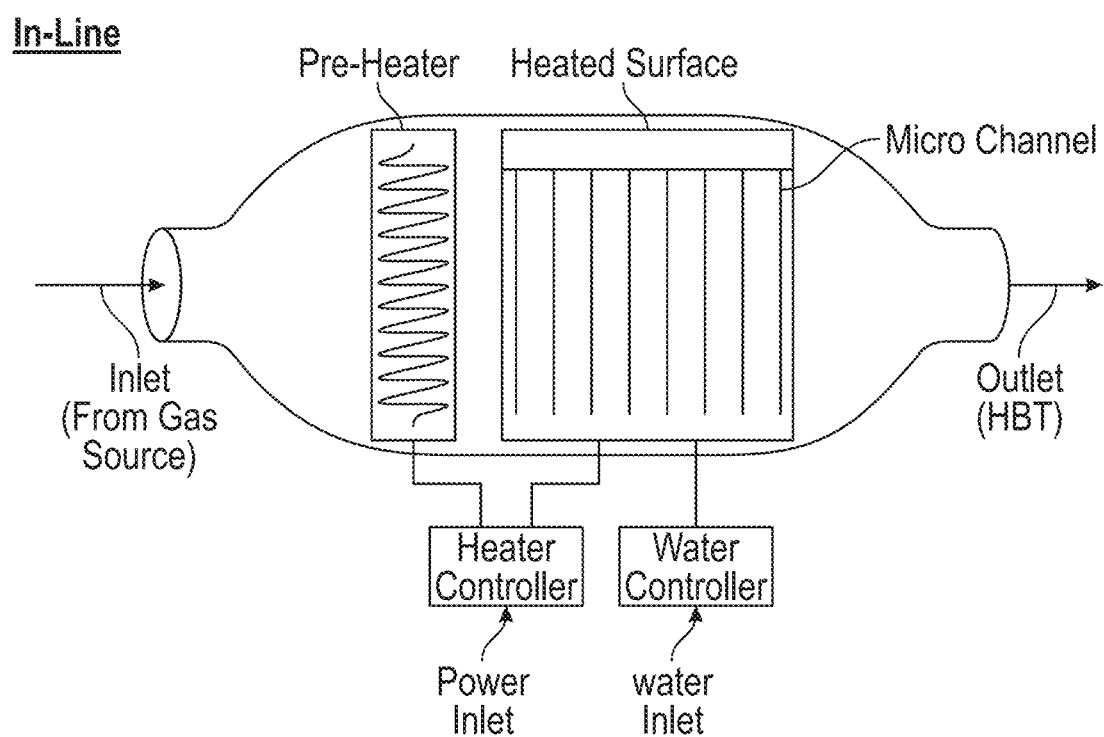
FIG. 13 is a schematic view of an inline humidification system in accordance with one an embodiment of the present disclosure.

FIG. 13 is a schematic view of an inline humidification system in accordance with one an embodiment of the present disclosure. The inline humidification system of FIG. 13 includes a pre-heater and a heater (the heater represented by the heated surface) in a gas passageway between an inlet and an outlet. A heater controller is connected to both the pre-heater and the heater. The pre-heater heats the gas before the gas reaches the heater. The heater is also connected to a water controller which dispenses water onto the heater surface. The amount of water applied by the water controller and the amount of heat applied by the heater controller may be deterministically controlled according to the principles described herein to vaporize the water and humidify the gas. The outlet of the system may be connected to a heated breathing tube (HBT), i.e. an inspiratory or delivery tube. The necessary power and sensing systems for the HBT may be provided integrally by the humidification system, or provided separately or externally. The advantages of including the humidification system as part of the delivery tube is simplicity, reduction in cost, and quality control by ensuring that it is replaced as necessary.

The foregoing description details certain embodiments of the systems, devices, and methods disclosed herein. It will be appreciated, however, that no matter how detailed the foregoing appears in text, the systems, devices, and methods may be practiced in many ways. As is also stated above, it should be noted that the use of particular terminology when describing certain features or aspects of the invention should not be taken to imply that the terminology is being redefined herein to be restricted to including any specific characteristics of the features or aspects of the technology with which that terminology is associated. "Approximately," or similar terms used herein, should be understood to mean within an acceptable tolerance of the specified item, for example, in reference to ° C., approximately can mean within an acceptable tolerance, such as, for example, within ±3° C.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment may be included with other depicted embodiments in any combination. For example, any of the various components described herein and/or depicted in the Figures may be combined, interchanged or excluded from other embodiments.

What is claimed is:

1. A respiratory humidification system for providing humidification to gases that pass through a gases passage way before being provided to an airway of a patient, the respiratory humidification system comprising:

a liquid flow controller for providing a controlled flow of liquid;

a heating system including a heating surface configured to be located in a gases passage way and provide humidification to gases passing through the gases passage way, wherein the heating system receives the controlled flow of liquid at the heating surface within the gases passage way to cause at least a portion of the controlled flow of liquid to evaporate within the gases passage way, the heating system configured to maintain the heating surface at a temperature of between approximately 30° C. and approximately 99.9° C.; and one or more hardware processors providing deterministic control of a humidity level of gases passing through the gases passage way by instructing the liquid flow controller to adjust the controlled flow of liquid received at the heating system based on a flow rate of gases through the gases passage way, and an evaporation rate of said controlled flow of liquid from the heating surface.

2. The respiratory humidification system of claim 1, wherein the liquid flow controller comprises a metering system.

3. The respiratory humidification system of claim 1, wherein the liquid flow controller comprises a pump, wherein the pump is a positive displacement pump or a gravity feed and a control valve.

4. The respiratory humidification system of claim 1, wherein the liquid flow controller comprises a non-return valve.

5. The respiratory humidification system of claim 1, further comprising a liquid reservoir.

6. The respiratory humidification system of claim 1, wherein the liquid flow controller is a pump in an open loop configuration.

7. The respiratory humidification system of claim 1, further comprising a flow sensor, wherein the sensor is configured to measure the controlled flow of liquid.

8. The respiratory humidification system of claim 7, wherein the liquid flow controller is a pump or flow actuator in series with the flow sensor in a closed loop configuration.

9. The respiratory humidification system of claim 1, wherein the one or more hardware processors provides deterministic control of the humidity level based on one or more of the following:

the flow rate of the gases;

a humidity level based on the dew point temperature of the gases at the inlet;

a humidity level based on enthalpy provided by the heating surface;

a pressure of the gases;

a function of gas velocity; and/or a temperature of the liquid in the controlled flow of liquid.

10. The respiratory humidification system of claim 1, further comprising one or more of the following: a water temperature sensor, a gas flow rate sensor at an outlet of the gases passage way, and a gas flow rate sensor at an inlet of the gases passage way.

11. The respiratory humidification system of claim 1, further comprising a gases pre-heater.

12. The respiratory humidification system of claim 1, further comprising one or more of the following:

an ambient pressure sensor;

a pressure sensor positioned at or near the heating surface;

a heating surface temperature sensor;

a first ambient dew point temperature sensor or an ambient humidity sensor positioned upstream of a humidification region;

a second ambient dew point temperature sensor positioned upstream from a gases pre-heater;

a third ambient dew point temperature sensor positioned downstream from a gases pre-heater; and/or a fourth ambient dew point temperature sensor positioned downstream from the gases pre-heater and combined with a second temperature sensor at a gases passage way inlet.

13. The respiratory humidification system of any of claim 1, further comprising at least one temperature sensor forming part of the heating system, wherein said at least one temperature sensor is in thermal contact with the heating surface.

14. The respiratory humidification system of claim 13, wherein the at least one temperature sensor is utilized to determine a proportion of the heater that is saturated with a liquid.

15. The respiratory humidification system of claim 1, further comprising a liquid pre-heater.

16. The respiratory humidification system of claim 1, wherein the heating surface comprises a wicking surface.

17. The respiratory humidification system of claim 1, wherein the evaporation rate is controlled by one or more of:
control of a temperature of the heating surface;
control of an evaporative area of the heating surface; and
the controlled flow of liquid received at the heating system.

18. The respiratory humidification system of claim 1, wherein the controlled flow of liquid is configured to be provided to the heating surface so as to cover the heating surface as a thin film.

19. The respiratory humidification system of claim 1, wherein the one or more hardware processors provides deterministic control of the humidity level based on one or more of:
a relative humidity level of the gases prior to interaction with the heating system;
a temperature of the gases prior to interaction with the heating system; and
an absolute or barometric pressure of gases at the inlet.

20. The respiratory humidification system of claim 11, wherein the gases pre-heater is controlled to heat the gases to a desired downstream temperature after the pre-heater, the desired downstream temperature set to be between 0° C. and approximately 5° C. above a gases output temperature.

* * * * *